(12) United States Patent
Craggs et al.

(10) Patent No.: US 9,908,939 B2
(45) Date of Patent: Mar. 6, 2018

(54) ANTIBODIES

(71) Applicant: UCB BIOPHARMA SPRL, Brussels (BE)

(72) Inventors: Graham Craggs, Slough (GB); Karine Jeannine Madeleine Hervé, Slough (GB); Diane Marshall, Slough (GB)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

(21) Appl. No.: 14/914,676

(22) PCT Filed: Aug. 26, 2014

(86) PCT No.: PCT/EP2014/068050
§ 371 (c)(1),
(2) Date: Feb. 26, 2016

(87) PCT Pub. No.: WO2015/028455
PCT Pub. Date: Mar. 5, 2015

(65) Prior Publication Data
US 2016/0200821 A1    Jul. 14, 2016

(30) Foreign Application Priority Data
Aug. 30, 2013 (GB) .................................. 1315487.7

(51) Int. Cl.
C07K 16/28 (2006.01)
C07K 16/00 (2006.01)
C12P 21/08 (2006.01)
A61K 39/00 (2006.01)

(52) U.S. Cl.
CPC .... C07K 16/2866 (2013.01); *A61K 2039/505* (2013.01); *C07K 2317/24* (2013.01); *C07K 2317/33* (2013.01); *C07K 2317/565* (2013.01); *C07K 2317/76* (2013.01); *C07K 2317/92* (2013.01); *C07K 2317/94* (2013.01)

(58) Field of Classification Search
None
See application file for complete search history.

(56) References Cited

FOREIGN PATENT DOCUMENTS

| WO | WO 2009/026303 | 2/2009 |
|---|---|---|
| WO | WO 2011/070024 | 6/2011 |
| WO | WO 2011/140249 | 11/2011 |
| WO | WO 2012/110360 | 8/2012 |
| WO | WO 2013/087699 | 6/2013 |
| WO | WO 2015/028454 | 3/2015 |

OTHER PUBLICATIONS

Rudikoff et al., Proc Natl Acad Sci USA 79: 1979-1983, 1982.*
Colman, Research in Immunology 145: 33-36, 1994.*
Kussie et al., J. Immunol. 152: 146-152, 1994.*
Chen et al., EMBO J., 14: 2784-2794, 1995.*
Lim, A.K.H., et al., "Antibody blockade of *c-fms* suppresses the progression of inflammation and injury in early diabetic nephropathy in obese *db/db* mice," *Diabetologia: Clinical and Experimental Diabetes and Metabolism*, May 23, 2009, vol. 52, No. 8, pp. 1669-1679.
MacDonald, K.P.A., et al., "An antibody against the colony-stimulating factor 1 receptor depletes the resident subset of monocytes and tissue- and tumor-associated macrophages but does not inhibit inflammation," *Blood*, Nov. 11, 2010, vol. 116, No. 19, pp. 3955-3963.
Paulus, P., et al., "Colony-Stimulating Factor-1 Antibody Reverses Chemoresistance in Human MCF-7 Breast Cancer Xenografts," *Cancer Research*, Apr. 15, 2006, vol. 66, No. 8, pp. 4349-4356.
Written Opinion in International Application No. PCT/EP2014/068050, dated Nov. 6, 2014, pp. 1-7.
Pedroza, M. et al. "Interleukin-6 Contributes to Inflammation and Remodeling in a Model of Adenosine Mediated Lung Injury" *PLoS ONE*, Jul. 2011, pp. 1-13, vol. 6, No. 7.

* cited by examiner

*Primary Examiner* — Christine J Saoud
*Assistant Examiner* — Jegatheesan Seharaseyon
(74) *Attorney, Agent, or Firm* — Saliwanchik, Lloyd & Eisenschenk

(57) ABSTRACT

The present invention relates to an anti-CSF-1R antibody and binding fragments thereof, DNA encoding the same, host cells comprising said DNA and methods of expressing the antibody or binding fragment in a host cell. The present invention also extends to pharmaceutical compositions comprising the antibody or a binding fragment thereof and use of the antibody, binding fragment and compositions comprising the same in treatment.

13 Claims, 35 Drawing Sheets

FIGURE 1A

CA019_969 Ab sequences

CDR-L1

LASEDIYDNLA    SEQ ID NO:1

CDRL2

YASSLQD        SEQ ID NO:2

CDR-L3

LQDSEYPWT      SEQ ID NO:3

CDR-H1

GFSLTTYGMGVG   SEQ ID NO:4

CDR-H2

NIWWDDDKYYNPSLKN    SEQ ID NO:5

CDR-H3

IGPIKYPTAPYRYFDF    SEQ ID NO:6

FIGURE 1B

Rat Ab 969 VL region       SEQ ID NO:7

DIQMTQSPAS LSASLGETVS IECLASEDIY DNLAWYQKKP GKSPHLLIYY
ASSLQDGVPS RFSGSGSGTQ YSLKINSLES EDAATYFCLQ DSEYPWTFGG
GTKLELK

Rat Ab 969 VL region       SEQ ID NO:8 gacatccaga tgacacagtc tccagcttcc ctgtctgcat ctctgggaga
aactgtctcc atcgaatgtc tagcaagtga ggacatttac gataatttag
cgtggtacca gaagaagcca ggaaaatctc ctcacctcct catctattat
gcaagtagct tgcaagatgg ggtcccatca cggttcagtg gcagtggatc
tggcacacag tattctctca aaatcaacag cctggaatct gaagatgctg
cgacttattt ctgtctacag gattctgagt atccgtggac gttcggtgga
ggcaccaagc tggaattgaa a Rat Ab 969 VL region with signal sequence underlined and italicised SEQ ID NO:9

*MGVPTQLLVL LLLWITDAIC* DIQMTQSPAS LSASLGETVS IECLASEDIY
DNLAWYQKKP GKSPHLLIYY ASSLQDGVPS RFSGSGSGTQ YSLKINSLES
EDAATYFCLQ DSEYPWTFGG GTKLELK

Rat Ab 969 VL region with signal sequence underlined and italicised SEQ ID NO:10

*atgggtgtcc ccactcagct cttggtgttg ttgctgctgt ggattacaga
tgccatatgt* gacatccaga tgacacagtc tccagcttcc ctgtctgcat
ctctgggaga aactgtctcc atcgaatgtc tagcaagtga ggacatttac
gataatttag cgtggtacca gaagaagcca ggaaaatctc ctcacctcct
catctattat gcaagtagct tgcaagatgg ggtcccatca cggttcagtg
gcagtggatc tggcacacag tattctctca aaatcaacag cctggaatct
gaagatgctg cgacttattt ctgtctacag gattctgagt atccgtggac
gttcggtgga ggcaccaagc tggaattgaa a Rat Ab 969 VH region SEQ ID NO:11

QVTLKESGPG ILQPSQTLSL TCTFSGFSLT TYGMGVGWIR QPSGKGLEWL
ANIWWDDDKY YNPSLKNRLT ISKDTSNNQA FLKLTNVHTS DSATYYCARI
GPIKYPTAPY RYFDFWGPGT MVTVS

FIGURE 1B (continued)

Rat Ab 969 VH region SEQ ID NO:12

```
caggttactc tgaaagagtc tggccctggg atattgcagc cctcccagac
cctcagtctg acttgcactt tctctggktt ttcactgacc acttatggta
tgggtgtggg ctggattcgt cagccttcag ggaagggtct ggagtggctg
gcaaacattt ggtgggatga tgataagtat tacaatccat ctctgaaaaa
ccggctcaca atctccaagg acacctccaa caaccaagca ttcctcaagc
tcaccaatgt acacacttca gattctgcca catactactg tgctcggata
gggccgatta aatacccgac ggcccctac cggtactttg acttctgggg
cccaggaacc atggtcaccg tctcg
```

Rat Ab 969 VH region with signal sequence underlined and italicised SEQ ID NO:13

*MDRLTSSFLL* *LIVPAYVLSQ* VTLKESGPGI LQPSQTLSLT CTFSGFSLTT
YGMGVGWIRQ PSGKGLEWLA NIWWDDDKYY NPSLKNRLTI SKDTSNNQAF
LKLTNVHTSD SATYYCARIG PIKYPTAPYR YFDFWGPGTM VTVS

Rat Ab 969 VH region with signal sequence underlined and italicised SEQ ID NO:14

```
atggacaggc ttacttcctc attcctactg ctgattgtcc ctgcatatgt
cctgtctcag gttactctga aagagtctgg ccctggata ttgcagccct
cccagaccct cagtctgact tgcactttct ctggttttc actgaccact
tatggtatgg gtgtggctg gattcgtcag ccttcaggga agggtctgga
gtggctggca aacatttggt gggatgatga taagtattac aatccatctc
tgaaaaaccg gctcacaatc tccaaggaca cctccaacaa ccaagcattc
ctcaagctca ccaatgtaca cacttcagat tctgccacat actactgtgc
tcggataggg ccgattaaat acccgacggc ccctaccgg tactttgact
tctggggccc aggaaccatg gtcaccgtct cg
```

FIGURE 1C 969 gL7 V-region     SEQ ID NO:15

DIQMTQSPSS LSASVGDRVT ITCLASEDIY DNLAWYQQKP GKAPKLLIYY
ASSLQDGVPS RFSGSGSGTD YTLTISSLQP EDFATYYCLQ DSEYPWTFGG
GTKVEIK 969 gL7 V-region     SEQ ID NO:16 gacatacaga tgactcagtc accctcaagc ctgagtgcca gtgtgggaga
cagggtgaca atcacctgtc tggcctccga ggatatctac gataacctgg
catggtatca gcagaaacct ggaaaggctc caagctcct gatttattat
gcctcctctc tccaagacgg cgttccatct cggttcagcg gaagcggctc
cgggacggat tacacactga caattagctc tctgcaaccg gaggattttg
ctacttacta ctgcctgcaa gactccgaat acccatggac cttcggtggt
ggcaccaaag tggaaatcaa g 969 gL7 V-region with signal sequence underlined and italicized     SEQ ID NO:17

*MSVPTQVLGL LLLWLTDARC* DIQMTQSPSS LSASVGDRVT ITCLASEDIY
DNLAWYQQKP GKAPKLLIYY ASSLQDGVPS RFSGSGSGTD YTLTISSLQP
EDFATYYCLQ DSEYPWTFGG GTKVEIK 969 gL7 V-region with signal sequence underlined and italicized     SEQ ID NO:18

*atgagcgtgc ctactcaagt cttggggctg ctcttgcttt ggcttaccga*
*cgcaagatgc* gacatacaga tgactcagtc accctcaagc ctgagtgcca
gtgtgggaga cagggtgaca atcacctgtc tggcctccga ggatatctac
gataacctgg catggtatca gcagaaacct ggaaaggctc caagctcct
gatttattat gcctcctctc tccaagacgg cgttccatct cggttcagcg
gaagcggctc cgggacggat tacacactga caattagctc tctgcaaccg
gaggattttg ctacttacta ctgcctgcaa gactccgaat acccatggac
cttcggtggt ggcaccaaag tggaaatcaa g 969 gL7 light chain (V + constant)     SEQ ID NO:19

DIQMTQSPSS LSASVGDRVT ITCLASEDIY DNLAWYQQKP GKAPKLLIYY
ASSLQDGVPS RFSGSGSGTD YTLTISSLQP EDFATYYCLQ DSEYPWTFGG
GTKVEIKRTV AAPSVFIFPP SDEQLKSGTA SVVCLLNNFY PREAKVQWKV
DNALQSGNSQ ESVTEQDSKD STYSLSSTLT LSKADYEKHK VYACEVTHQG
LSSPVTKSFN RGEC

FIGURE 1C (continued)

969 gL7 light chain (V + constant) SEQ ID NO:20

```
gacatacaga tgactcagtc accctcaagc ctgagtgcca gtgtgggaga
cagggtgaca atcacctgtc tggcctccga ggatatctac gataacctgg
catggtatca gcagaaacct ggaaaggctc ccaagctcct gatttattat
gcctcctctc tccaagacgg cgttccatct cggttcagcg aagcggctc
cgggacggat tacacactga caattagctc tctgcaaccg gaggattttg
ctacttacta ctgcctgcaa gactccgaat acccatggac cttcggtggt
ggcaccaaag tggaaatcaa gcgtacggta gcggcccat ctgtcttcat
cttcccgcca tctgatgagc agttgaaatc tggaactgcc tctgttgtgt
gcctgctgaa taacttctat cccagagagg ccaaagtaca gtggaaggtg
gataacgccc tccaatcggg taactcccag gagagtgtca cagagcagga
cagcaaggac agcacctaca gcctcagcag caccctgacg ctgagcaaag
cagactacga gaaacacaaa gtctacgcct gcgaagtcac ccatcaggc
ctgagctcgc ccgtcacaaa gagcttcaac aggggagagt gt
```

969 gL7 light chain (V + constant) with signal sequence underlined and italicized SEQ ID NO:21

*MSVPTQVLGL LLLWLTDARC* DIQMTQSPSS LSASVGDRVT ITCLASEDIY
DNLAWYQQKP GKAPKLLIYY ASSLQDGVPS RFSGSGSGTD YTLTISSLQP
EDFATYYCLQ DSEYPWTFGG GTKVEIKRTV AAPSVFIFPP SDEQLKSGTA
SVVCLLNNFY PREAKVQWKV DNALQSGNSQ ESVTEQDSKD STYSLSSTLT
LSKADYEKHK VYACEVTHQG LSSPVTKSFN RGEC 969 gL7 light chain (V + constant) with signal sequence underlined and italicized SEQ ID NO:22

```
atgagcgtgc ctactcaagt cttggggctg ctcttgcttt ggcttaccga
cgcaagatgc gacatacaga tgactcagtc accctcaagc ctgagtgcca
gtgtgggaga cagggtgaca atcacctgtc tggcctccga ggatatctac
gataacctgg catggtatca gcagaaacct ggaaaggctc ccaagctcct
gatttattat gcctcctctc tccaagacgg cgttccatct cggttcagcg
aagcggctc cgggacggat tacacactga caattagctc tctgcaaccg
gaggattttg ctacttacta ctgcctgcaa gactccgaat acccatggac
cttcggtggt ggcaccaaag tggaaatcaa gcgtacggta gcggcccat
ctgtcttcat cttcccgcca tctgatgagc agttgaaatc tggaactgcc
tctgttgtgt gcctgctgaa taacttctat cccagagagg ccaaagtaca
gtggaaggtg gataacgccc tccaatcggg taactcccag gagagtgtca
cagagcagga cagcaaggac agcacctaca gcctcagcag caccctgacg
ctgagcaaag cagactacga gaaacacaaa gtctacgcct gcgaagtcac
ccatcaggc ctgagctcgc ccgtcacaaa gagcttcaac aggggagagt
gt
```

FIGURE 1D 969 gH2 V-region     SEQ ID NO:23

EVTLKESGPA LVKPTQTLTL TCTFSGFSLT TYGMGVGWIR QPPGKALEWL
ANIWWDDDKY YNPSLKNRLT ISKDTSKNQV VLTMTNMDPV DTATYYCARI
GPIKYPTAPY RYFDFWGQGT MVTVS 969 gH2 V-region     SEQ ID NO:24 gaagtgacac tcaaggagtc tggacccgct ctggtgaaac caacccaaac
actcactttg acatgtactt ttagtggctt ctcattgact acctatggaa
tgggcgtggg atggatcaga cagccacctg gcaaggctct ggaatggctg
gccaacatct ggtgggatga cgacaagtac tataacccgt ccctgaaaaa
ccggctgacc attagcaagg atacttctaa aaatcaagtg gtgctgacca
tgacaaatat ggatccgtt gacaccgcaa cctactactg cgcccgcatt
ggtcccataa agtaccctac ggcaccttac cgatatttcg acttttgggg
ccaagggaca atggttactg tctcg 969 gH2 V-region with signal sequence underlined and italicized SEQ ID NO:25

*MEWSWVFLFF LSVTTGVHSE* VTLKESGPAL VKPTQTLTLT CTFSGFSLTT
YGMGVGWIRQ PPGKALEWLA NIWWDDDKYY NPSLKNRLTI SKDTSKNQVV
LTMTNMDPVD TATYYCARIG PIKYPTAPYR YFDFWGQGTM VTVS 969 gH2 V-region with signal sequence underlined and italicized SEQ ID NO:26

<u>*atggagtggt cctgggtgtt tctgttcttc ctgagtgtga ccaccggggt*</u>
<u>*ccactcc*</u>gaa gtgacactca aggagtctgg acccgctctg gtgaaaccaa
cccaaacact cactttgaca tgtacttta gtggcttctc attgactacc
tatggaatgg gcgtgggatg gatcagacag ccacctggca aggctctgga
atggctggcc aacatctggt gggatgacga caagtactat aacccgtccc
tgaaaaaccg gctgaccatt agcaaggata cttctaaaaa tcaagtggtg
ctgaccatga caaatatgga tccgttgac accgcaacct actactgcgc
ccgcattggt cccataaagt accctacggc accttaccga tatttcgact
tttggggcca aggacaatg gttactgtct cg

FIGURE 1D (continued)

969 gH2 heavy chain (V + constant – hu IgG4P)    SEQ ID NO:27

```
EVTLKESGPA  LVKPTQTLTL  TCTFSGFSLT  TYGMGVGWIR  QPPGKALEWL
ANIWWDDDKY  YNPSLKNRLT  ISKDTSKNQV  VLTMTNMDPV  DTATYYCARI
GPIKYPTAPY  RYFDFWGQGT  MVTVSSASTK  GPSVFPLAPC  SRSTSESTAA
LGCLVKDYFP  EPVTVSWNSG  ALTSGVHTFP  AVLQSSGLYS  LSSVVTVPSS
SLGTKTYTCN  VDHKPSNTKV  DKRVESKYGP  PCPPCPAPEF  LGGPSVFLFP
PKPKDTLMIS  RTPEVTCVVV  DVSQEDPEVQ  FNWYVDGVEV  HNAKTKPREE
QFNSTYRVVS  VLTVLHQDWL  NGKEYKCKVS  NKGLPSSIEK  TISKAKGQPR
EPQVYTLPPS  QEEMTKNQVS  LTCLVKGFYP  SDIAVEWESN  GQPENNYKTT
PPVLDSDGSF  FLYSRLTVDK  SRWQEGNVFS  CSVMHEALHN  HYTQKSLSLS
LGK
```

969 gH2 heavy chain (V + constant – hu IgG4P, exons underlined) SEQ ID NO:28

```
gaagtgacac  tcaaggagtc  tggacccgct  ctggtgaaac  caacccaaac
actcactttg  acatgtactt  ttagtggctt  ctcattgact  acctatggaa
tgggcgtggg  atggatcaga  cagccacctg  caaggctct   ggaatggctg
gccaacatct  ggtgggatga  cgacaagtac  tataacccgt  ccctgaaaaa
ccggctgacc  attagcaagg  atacttctaa  aaatcaagtg  gtgctgacca
tgacaaatat  ggatcccgtt  gacaccgcaa  cctactactg  cgcccgcatt
ggtcccataa  agtaccctac  ggcacttac   cgatatttcg  acttttgggg
ccaagggaca  atggttactg  tctcgagcgc  ttctacaaag  ggcccatccg
tcttccccct  ggcgcctgc   tccaggagca  cctccgagag  cacagccgcc
ctgggctgcc  tggtcaagga  ctacttcccc  gaaccggtga  cggtgtcgtg
gaactcaggc  gccctgacca  gcggcgtgca  caccttcccg  gctgtcctac
agtcctcagg  actctactcc  ctcagcagcg  tggtgaccgt  gccctccagc
agcttgggca  cgaagaccta  cacctgcaac  gtagatcaca  agcccagcaa
caccaaggtg  gacaagagag  ttggtgagag  gccagcacag  ggagggaggg
tgtctgctgg  aagccaggct  cagccctcct  gcctggacgc  accccggctg
tgcagcccca  gcccagggca  gcaaggcatg  ccccatctgt  ctcctcaccc
ggaggcctct  gaccacccca  ctcatgccca  gggagagggt  cttctggatt
tttccaccag  gctccgggca  gccacaggct  ggatgcccct  accccaggcc
ctgcgcatac  agggcaggt   gctgcgctca  gacctgccaa  gagccatatc
cgggaggacc  ctgccctga   cctaagccca  ccccaaaggc  caaactctcc
actccctcag  ctcagacacc  ttctctcctc  ccagatctga  gtaactccca
atcttctctc  tgcagagtcc  aaatatggtc  cccatgccc   accatgccca
ggtaagccaa  cccaggcctc  gccctccagc  tcaaggcggg  acaggtgccc
tagagtagcc  tgcatccagg  gacaggcccc  agccggtgc   tgacgcatcc
acctccatct  cttcctcagc  acctgagttc  ctgggggac   catcagtctt
cctgttcccc  ccaaaaccca  aggacactct  catgatctcc  cggacccctg
aggtcacgtg  cgtggtggtg  gacgtgagcc  aggaagaccc  cgaggtccag
ttcaactggt  acgtggatgg  cgtggaggtg  cataatgcca  agacaaagcc
```

FIGURE 1D (continued)

```
gcgggaggag cagttcaaca gcacgtaccg tgtggtcagc gtcctcaccg
tcctgcacca ggactggctg aacggcaagg agtacaagtg caaggtctcc
aacaaaggcc tcccgtcctc catcgagaaa accatctcca agccaaagg
tgggaccac ggggtgcgag ggccacatgg acagaggtca gctcggccca
ccctctgccc tgggagtgac cgctgtgcca acctctgtcc ctacagggca
gccccgagag ccacaggtgt acacctgcc cccatccag gaggagatga
ccaagaacca ggtcagcctg acctgcctgg tcaaaggctt ctacccagc
gacatcgccg tggagtggga gagcaatggg cagccggaga caactacaa
gaccacgcct cccgtgctgg actccgacgg ctccttcttc ctctacagca
ggctaaccgt ggacaagagc aggtggcagg aggggaatgt cttctcatgc
tccgtgatgc atgaggctct gcacaaccac tacacacaga agagcctctc
cctgtctctg ggtaaa
```

969 gH2 heavy chain (V + constant – hu IgG4P) with signal sequence underlined and italicised
SEQ ID NO:29

*MEWSWVFLFF LSVTTGVHSE* VTLKESGPAL VKPTQTLTLT CTFSGFSLTT
YGMGVGWIRQ PPGKALEWLA NIWWDDDKYY NPSLKNRLTI SKDTSKNQVV
LTMTNMDPVD TATYYCARIG PIKYPTAPYR YFDFWGQGTM VTVSSASTKG
PSVFPLAPCS RSTSESTAAL GCLVKDYFPE PVTVSWNSGA LTSGVHTFPA
VLQSSGLYSL SSVVTVPSSS LGTKTYTCNV DHKPSNTKVD KRVESKYGPP
CPPCPAPEFL GGPSVFLFPP KPKDTLMISR TPEVTCVVVD VSQEDPEVQF
NWYVDGVEVH NAKTKPREEQ FNSTYRVVSV LTVLHQDWLN GKEYKCKVSN
KGLPSSIEKT ISKAKGQPRE PQVYTLPPSQ EEMTKNQVSL TCLVKGFYPS
DIAVEWESNG QPENNYKTTP PVLDSDGSFF LYSRLTVDKS RWQEGNVFSC
SVMHEALHNH YTQKSLSLSL GK 969 gH2 heavy chain (V + constant – hu IgG4P, exons underlined) with signal sequence underlined and italicized    SEQ ID NO:30

*atggagtggt cctgggtgtt tctgttcttc ctgagtgtga ccaccggggt*
*ccactccgaa gtgacactca* aggagtctgg acccgctctg gtgaaaccaa
cccaaacact cactttgaca tgtacttta gtggcttctc attgactacc
tatggaatgg gcgtgggatg gatcagacag ccacctggca aggctctgga
atggctggcc aacatctggt gggatgacga caagtactat aacccgtccc
tgaaaaccg gctgaccatt agcaaggata cttctaaaaa tcaagtggtg
ctgaccatga caaatatgga tccgttgac accgcaacct actactgcgc
ccgcattggt cccataaagt accctacgg accttaccga tatttcgact
tttgggggcca aggacaatg gttactgtct cgagcgcttc tacaaaggc
ccatccgtct tccccctggc gcctgctcc aggagcacct ccgagagcac
agccgccctg ggctgcctgg tcaaggacta cttccccgaa ccggtgacgg

FIGURE 1D (continued)

```
tgtcgtggaa ctcaggcgcc ctgaccagcg gcgtgcacac cttcccggct
gtcctacagt cctcaggact ctactccctc agcagcgtgg tgaccgtgcc
ctccagcagc ttgggcacga agacctacac ctgcaacgta gatcacaagc
ccagcaacac caaggtggac aagagagttg gtgagaggcc agcacaggga
gggagggtgt ctgctggaag ccaggctcag ccctcctgcc tggacgcacc
ccggctgtgc agccccagcc cagggcagca aggcatgccc catctgtctc
ctcacccgga ggcctctgac caccccactc atgcccaggg agagggtctt
ctggattttt ccaccaggct ccgggcagcc acaggctgga tgccctacc
ccaggccctg cgcatacagg ggcaggtgct gcgctcagac ctgccaagag
ccatatccgg gaggaccctg cccctgacct aagcccaccc caaaggccaa
actctccact ccctcagctc agacaccttc tctcctccca gatctgagta
actcccaatc ttctctctgc agagtccaaa tatggtcccc catgcccacc
atgcccaggt aagccaaccc aggcctcgcc ctccagctca aggcgggaca
ggtgccctag agtagcctgc atccagggac aggccccagc cgggtgctga
cgcatccacc tccatctctt cctcagcacc tgagttcctg ggggaccat
cagtcttcct gttcccccca aaacccaagg acactctcat gatctcccgg
accctgagg tcacgtgcgt ggtggtggac gtgagccagg aagacccga
ggtccagttc aactggtacg tggatggcgt ggaggtgcat aatgccaaga
caaagccgcg ggaggagcag ttcaacagca cgtaccgtgt ggtcagcgtc
ctcaccgtcc tgcaccagga ctggctgaac ggcaaggagt acaagtgcaa
ggtctccaac aaaggcctcc cgtcctccat cgagaaaacc atctccaaag
ccaaaggtgg gacccacggg gtgcgagggc cacatggaca gaggtcagct
cggcccaccc tctgcctgg gagtgaccgc tgtgccaacc tctgtcccta
cagggcagcc ccgagagcca caggtgtaca ccctgccccc atcccaggag
gagatgacca agaaccaggt cagcctgacc tgcctggtca aaggcttcta
ccccagcgac atcgccgtgg agtgggagag caatgggcag ccggagaaca
actacaagac cacgcctccc gtgctggact ccgacggctc cttcttcctc
tacagcaggc taaccgtgga caagagcagg tggcaggagg ggaatgtctt
ctcatgctcc gtgatgcatg aggctctgca caaccactac acacagaaga
gcctctccct gtctctgggt aaa
```

FIGURE 1E

Human VK1 2-1-(1) O12 JK4 acceptor framework  SEQ ID NO:31

DIQMTQSPSS LSASVGDRVT ITCRASQSIS SYLNWYQQKP GKAPKLLIYA
ASSLQSGVPS RFSGSGSGTD FTLTISSLQP EDFATYYCQQ SYSTPLTFGG GTKVEIK

Human VK1 2-1-(1) O12 JK4 acceptor framework  SEQ ID NO:32

```
gacatccaga tgacccagtc tccatcctcc ctgtctgcat ctgtaggaga
cagagtcacc atcacttgcc gggcaagtca gagcattagc agctatttaa
attggtatca gcagaaacca gggaaagccc ctaagctcct gatctatgct
gcatccagtt tgcaaagtgg ggtcccatca aggttcagtg gcagtggatc
tgggacagat ttcactctca ccatcagcag tctgcaacct gaagattttg
caacttacta ctgtcaacag agttacagta cccctctcac tttcggcgga
gggaccaagg tggagatcaa a
```

Human VH2 3-1 2-70 JH3 acceptor framework    SEQ ID NO:33

QVTLKESGPA LVKPTQTLTL TCTFSGFSLS TSGMRVSWIR QPPGKALEWL
ARIDWDDDKF YSTSLKTRLT ISKDTSKNQV VLTMTNMDPV DTATYYCARI
AFDIWGQGTM VTVS

Human VH2 3-1 2-70 JH3 acceptor framework    SEQ ID NO:34

```
caggtcacct tgaaggagtc tggtcctgcg ctggtgaaac ccacacagac
cctcacactg acctgcacct tctctgggtt ctcactcagc actagtggaa
tgcgtgtgag ctggatccgt cagccccag ggaaggccct ggagtggctt
gcacgcattg attgggatga tgataaattc tacagcacat ctctgaagac
caggctcacc atctccaagg acacctccaa aaaccaggtg gtccttacaa
tgaccaacat ggaccctgtg gacacagcca cgtattactg tgcacggata
gcttttgata tctggggcca agggacaatg gtcaccgtct ct
```

FIGURE 1F

Amino acid sequence for CSF-1R  SEQ ID NO: 35

```
MGPGVLLLLL VATAWHGQGI PVIEPSVPEL VVKPGATVTL RCVGNGSVEW
DGPPSPHWTL YSDGSSSILS TNNATFQNTG TYRCTEPGDP LGGSAAIHLY
VKDPARPWNV LAQEVVVFED QDALLPCLLT DPVLEAGVSL VRVRGRPLMR
HTNYSFSPWH GFTIHRAKFI QSQDYQCSAL MGGRKVMSIS IRLKVQKVIP
GPPALTLVPA ELVRIRGEAA QIVCSASSVD VNFDVFLQHN NTKLAIPQQS
DFHNNRYQKV LTLNLDQVDF QHAGNYSCVA SNVQGKHSTS MFFRVVESAY
LNLSSEQNLI QEVTVGEGLN LKVMVEAYPG LQGFNWTYLG PFSDHQPEPK
LANATTKDTY RHTFTLSLPR LKPSEAGRYS FLARNPGGWR ALTFELTLRY
PPEVSVIWTF INGSGTLLCA ASGYPQPNVT WLQCSGHTDR CDEAQVLQVW
DDPYPEVLSQ EPFHKVTVQS LLTVETLEHN QTYECRAHNS VGSGSWAFIP
ISAGAHTHPP DEFLFTPVVV ACMSIMALLL LLLLLLLYKY KQKPKYQVRW
KIIESYEGNS YTFIDPTQLP YNEKWEFPRN NLQFGKTLGA GAFGKVVEAT
AFGLGKEDAV LKVAVKMLKS TAHADEKEAL MSELKIMSHL GQHENIVNLL
GACTHGGPVL VITEYCCYGD LLNFLRRKAE AMLGPSLSPG QDPEGGVDYK
NIHLEKKYVR RDSGFSSQGV DTYVEMRPVS TSSNDSFSEQ DLDKEDGRPL
ELRDLLHFSS QVAQGMAFLA SKNCIHRDVA ARNVLLTNGH VAKIGDFGLA
RDIMNDSNYI VKGNARLPVK WMAPESIFDC VYTVQSDVWS YGILLWEIFS
LGLNPYPGIL VNSKFYKLVK DGYQMAQPAF APKNIYSIMQ ACWALEPTHR
PTFQQICSFL QEQAQEDRRE RDYTNLPSSS RSGGSGSSSS ELEEESSSEH
LTCCEQGDIA QPLLQPNNYQ FC
```

Amino acid sequence for CSF-1R  SEQ ID NO: 36

```
IPVIEPSVPELVVKPGATVTLRCVGNGSVEWDGPPSPHWTLYSDGSSSILSTNNATFQNTGTYR
CTEPGDPLGGSAAIHLYVKDPARPWNVLAQEVVVFEDQDALLPCLLTDPVLEAGVSLVRVRGRP
LMRHTNYSFSPWHGFTIHRAKFIQSQDYQCSALMGGRKVMSISIRLKVQKVIPGPPALTLVPAE
LVRIRGEAAQIVCSASSVDVNFDVFLQHNNTKLAIPQQSDFHNNRYQKVLTLNLDQVDFQHAGN
YSCVASNVQGKHSTSMFFRVV
```

Amino acid sequence for CSF-1R  SEQ ID NO: 37

```
MRHTNYSFSPWHGFTIHRAKFIQSQDYQCSALMGGRKVMSISIRLKVQK
```

Amino acid sequence for CSF-1R SEQ ID NO:38 (SNP V32G, A245S, H247P, V279M, position underlined)

```
IPVIEPSVPELVVKPGATVTLRCVGNGSVEWDGPPSPHWTLYSDGSSSILSTNNATFQNTGTYR
CTEPGDPLGGSAAIHLYVKDPARPWNVLAQEVVVFEDQDALLPCLLTDPVLEAGVSLVRVRGRP
LMRHTNYSFSPWHGFTIHRAKFIQSQDYQCSALMGGRKVMSISIRLKVQKVIPGPPALTLVPAE
LVRIRGEAAQIVCSASSVDVNFDVFLQHNNTKLAIHQQSDFHNNRYQKVLTLNLDQVDFQHAGN
YSCVASNVQGKHSTSMFFRVVESAYLNLSSEQNLIQEVTVGEGLNLKVMVEAYPGLQGFNWTYL
GPFSDHQPEPKLANATTKDTYRHTFTLSLPRLKPSEAGRYSFLARNPGGWRALTFELTLRYPPE
VSVIWTFINGSGTLLCAASGYPQPNVTWLQCSGHTDRCDEAQVLQVWDDPYPEVLSQEPFHKVT
VQSLLTVETLEHNQTYECRAHNSVGSGSWAFIPISAGAHTHPPDE
```

FIGURE 2A

```
LIGHT CHAIN Graft 969

1    5   10   15   20   25   30   35   40   45   50   55   60   65   70   75   80   85   90   95  100  105
Light 969          DIQMTQSPASLSASLGETVSIECLASEDIYDNLAWYQKKPGKSPHLLIYAASSLQDGVPSRFSGSGSGTQYSLKINSLESEDAATYFCLQDSEYPWTFGGGTKLELK
                                   |  ||  |||                 | |     |     |||           |||                     |
VK1 2-1-(1) O12    DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK
                                                 |||||                 | |                |||
969 gL7            DIQMTQSPSSLSASVGDRVTITCLASEDIYDNLAWYQQKPGKAPKLLIYAASSLQDGVPSRFSGSGSGTDYTLTISSLQPEDFATYYCLQDSEYPWTFGGGTKVEIK
```

Legend

969 = Rat variable light chain sequence
969 gL7 = Humanized graft of 969 variable light chain using VK1 2-1-(1) O12 plus JK4 human germline as the acceptor framework.

CDRs are shown in bold/underlined
Donor residue is shown in bold/italic and is highlighted: Y71

FIGURE 2B

HEAVY CHAIN Graft 969

```
               1    5    10   15   20   25   30 ab  35   40   45   50   55   60   65   70   75   80 abc 85   90   95       105 1
Heavy 969      QVTLKESGPGILQPSQTLSLTCTFSGFSLTTYGMGVGWIRQPSGKGLEWLANIWWDDDKYYNPSLKNRLTISKDTSNNQAFLKLTNVHTSDSATYYCARIGPIKYPTAPYRYFDFWGPGTMVTVS
                                    ||||                  |                                |  | || || ||||                             |
VH2 3-1 2-70   QVTLKESGPALVKPTQTLTLTCTFSGFSLSTSGMRVSWIRQPPGKALEWLARIDWDDDKFYSTSLKTRLTISKDTSKNQVVLTMTNMDPVDTATYYCARI----------AFDVWGQGTMVTVS
969gH2         EVTLKESGPALVKPTQTLTLTCTFSGFSLTTYGMGVGWIRQPPGKALEWLANIWWDDDKYYNPSLKNRLTISKDTSKNQVVLTMTNMDPVDTATYYCARIGPIKYPTAPYRYFDFWGQGTMVTVS
```

Legend

969 = Rat variable heavy chain sequence
969gH2 = Humanized graft of 969 variable heavy chain using VH2 3-1 2-70 plus JH3 human germline as the acceptor framework.

CDRs are shown in bold/underlined

FIGURE 3

SEQ ID NO: 39

```
MGPGVLLLLL VATAWHGQGI PVIEPSVPEL VVKPGATVTL RCVGNGSVEW DGPPSPHWTL YSDGSSSILS
TNNATFQNTG TYRCTEPGDP LGGSAAIHLY VKDPARPWNV LAQEVVVFED QDALLPCLLT DPVLEAGVSL
VRVRGRPLMR HTNYSFSPWH GFTIHRAKFI QSQDYQCSAL MGGRKVMSIS IRLKVQKVIP GPPALTLVPA
ELVRIRGEAA QIVCSASSVD VNFDVFLQHN NTKLAIPQQS DFHNNRYQKV LTLNLDQVDF QHAGNYSCVA
SNVQGKHSTS MFFRVVESAY LNLSSEQNLI QEVTVGEGLN LKVMVEAYPG LQGFNWTYLG PFSDHQPEPK
LANATTKDTY RHTFTLSLPR LKPSEAGRYS FLARNPGGWR ALTFELTLRY PPEVSVIWTF INGSGTLLCA
ASGYPQPNVT WLQCSGHTDR CDEAQVLQVW DDPYPEVLSQ EPFHKVTVQS LLTVETLEHN QTYECRAHNS
VGSGSWAFIP ISAGAHTHPP DE
```

FIGURE 13
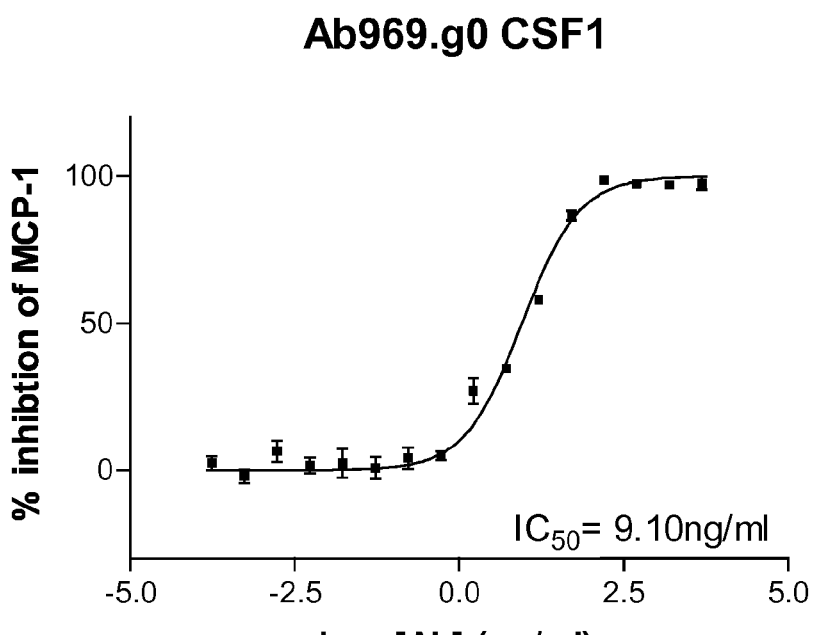
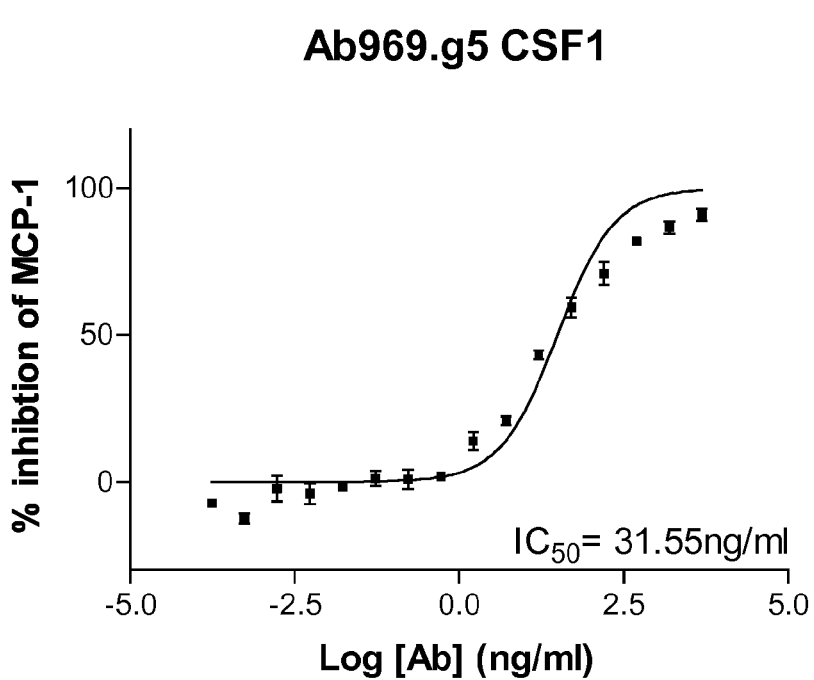

→ Group 1: Vehicle Control (PBS) s.c. 3x weekly d9 - d42 (n=12)
→ Group 2: 30mg/kg Control Antibody s.c. 3x weekly d9 - d42 (n=12) Group
→ 3: 10mg/kg Control Antibody s.c. 3x weekly d9 - d42 (n=12) Group 4:
→ 30mg/kg Antibody Ab535 s.c. 3x weekly d9 - d42 (n=12/9)
→ Group 5: 10mg/kg Antibody Ab535 s.c. 3x weekly d9 - d42 (n=11/10)
→ Group 6: 360mg/kg Positive Control i.v. once weekly for four weeks (day 10, 17, 24 and 31) (n=12/11)

* Denotes significant difference from ADA+ (wild type); # denotes significant difference from ADA-/- mice treated with isotype control antibody ($p \leq 0.05$).

ANTIBODIES

CROSS-REFERENCE TO RELATED APPLICATION

This application is the U.S. national stage application of International Patent Application No. PCT/EP2014/068050, filed Aug. 26, 2014.

The present invention relates to an anti-CSF-1R antibody and binding fragments thereof, DNA encoding the same, host cells comprising said DNA and methods of expressing the antibody or binding fragment in a host cell. The invention also extends to pharmaceutical compositions comprising the antibody or a binding fragment thereof and use of the antibody, binding fragment and compositions comprising the same in treatment.

The colony-stimulating factor 1 (CSF-1), also known as macrophage colony-stimulating factor (M-CSF), is a cytokine produced by a variety of cells, including macrophages, endothelial cells and fibroblasts. CSF-1 is composed of two "monomer" polypeptides, which form a biologically active dimeric CSF-1 protein. CSF-1 exists in at least three mature forms due to alternative RNA splicing (see Cerretti et al., 1988, Molecular Immunology, 25:761). The three forms of CSF-1 are translated from different mRNA precursors, which encode polypeptide monomers of 256 to 554 amino acids, having a 32 amino acid signal sequence at the amino terminus and a putative transmembrane region of approximately 23 amino acids near the carboxyl terminus. The precursor peptides are subsequently processed by amino terminal and carboxyl terminal proteolytic cleavages to release mature CSF-1. Residues 1-149 of all three mature forms of CSF-1 are identical and are believed to contain sequences essential for biological activity of CSF-1. In vivo CSF-1 monomers are glycosylated and dimerized via disulfide linkage. CSF-1 belongs to a group of biological agonists that promote the production of blood cells. Specifically, it acts as a growth and differentiation factor for bone marrow progenitor cells of the mononuclear phagocyte lineage. Further, CSF-1 stimulates the survival, proliferation and function of macrophages via a specific receptor on responding cells.

The CSF-1 receptor (CSF-1R) is also referred to as the c-fms gene product or CD115. CSF-1R is a 165 kDa type 1 TM glycoprotein belonging to the type III receptor tyrosine kinase family. In addition to CSF-1, the structurally similar but sequence unrelated molecule IL-34 has also been shown to be a ligand for CSF-1R (Lin et al., 2008, Science, 320:807-811). Expression of CSF-1R is restricted to cells of the monocyte-macrophage lineage, both circulating and resident tissue populations, and osteoclasts. In addition, it is expressed in a number of cells of the female reproductive system, including oocytes, decidual cells and trophoblasts.

Binding of the ligand CSF-1 to the CSF-1 receptor results in the phosphorylation of the receptor on one or more tyrosine residues, through the action of the tyrosine kinase domain. This phosphorylation can be detected because antibodies are available that bind to the receptor only after phosphorylation (for example, Phospho-M-CSF-Receptor (Tyr546) antibody #3083 from Cell Signaling Technology).

Expression of CSF-1 and CSF-1R correlates with tumour progression and poor diagnosis in many cancer types. Tumour-associated macrophages (TAMs) can be the major component of tumour stroma and high levels of CSF-1 and CSF-1R are associated with high TAM infiltrations and poor prognosis in a number of tumour types.

Antibodies to CSF-1R are known in the art. Sherr et al. (1989, Blood, 73:1786-1793) describe antibodies against CSF-1R that inhibit the CSF-1 activity. WO2009/026303 discloses anti-CSF-1R antibodies which bind to human CSF-1R and in vivo mouse tumour models using an anti-murine CSF-1R antibody. WO2011/123381 discloses anti-CSF-1R antibodies which internalize CSF-1R and have ADCC activity. WO2011/123381 also discloses in vivo mouse tumour models using an anti-murine CSF-1R antibody. WO2011/140249 discloses anti-CSF-1R antibodies which block binding of CSF-1 to CSF-1R and are stated to be useful in the treatment of cancer. WO2009/112245 discloses an anti-CSF-1R IgG1 antibody which inhibits CSF-1 binding to CSF-1R and is stated to be useful in the treatment of cancer, inflammatory bowel disease and rheumatoid arthritis. WO2011/131407 discloses an anti-CSF-1R antibody which inhibits CSF-1 binding to CSF-1R and is stated to be useful in the treatment of bone loss and cancer. WO2011/107553 discloses an anti-CSF-1R antibody which inhibits CSF-1 binding to CSF-1R and is thought to be useful in the treatment of bone loss and cancer. WO2011/070024 discloses anti-CSF-1R antibodies which bind to human CSF-1R fragment delD4.

There is a need in the art to provide new anti-CSF-1R antibodies suitable for therapeutic applications. While the therapeutic application of anti-CSF-1R antibodies in treating certain cancers has been previously described, there is still a need to provide new therapeutic applications for such antibodies.

The term 'fibrotic disease' refers to an aberrant wound-healing response wherein excess fibrous connective tissue is formed in an organ or tissue. The deposition and accumulation of excess extracellular matrix components, such as collagen and fibronectin, results in the hardening and scarring of tissues that can ultimately lead to organ failure.

Examples of fibrotic diseases include pulmonary fibrosis, such as idiopathic pulmonary fibrosis and cystic fibrosis, renal fibrosis, liver fibrosis, liver cirrhosis, primary sclerosing cholangitis, primary biliary cirrhosis, endomyocardial fibrosis, mediastinal fibrosis, myelofibrosis, retroperitoneal fibrosis, progressive massive fibrosis, nephrogenic systemic fibrosis, Crohn's disease, keloid, myocardial infarction, systemic sclerosis, scleroderma and arthrofibrosis.

Wounding results in an immediate coagulation and clotting response with the development of a provisional extracellular matrix (ECM). The platelet aggregation and activation helps promote an inflammatory response characterised by vasodilation and an increase in blood vessel permeability, allowing the recruitment of a variety of immune cells including neutrophils, macrophages, eosinophils and lymphocytes. Neutrophils and macrophages debride the wound, thereby reducing the risk of infection, and together with activated lymphocytes secrete a variety of growth factors and cytokines that serve to further amplify the inflammatory response. Molecules such as TGFβ, PDGF and IL-13 activate macrophages and lead to the recruitment, proliferation and activation of fibroblasts at the wound site. Activated fibroblasts, or myofibroblasts, are characterised by the expression of α-smooth muscle actin and secrete collagen and other ECM components. The activated fibroblasts contract the collagen lattice, drawing the edges of the wound to the centre. Epithelial and endothelial cells proliferate and migrate over the temporary matrix to regenerate the damaged tissue, completing the wound repair.

Persistent tissue insult or injury or a disregulation of the repair pathway leads to an inappropriate wound response. Excess deposition and hyper-cross-linking of the collagen and ECM occurs, resulting in excessive formation and hardening of the scar tissue in place of the normal tissue architecture.

The cause of fibrotic disease can be dependent upon the organ or tissue involved and is unknown in some diseases, such as idiopathic pulmonary fibrosis (IPF). Liver fibrosis and ultimately cirrhosis results from chronic liver damage sustained through exposure to a variety of factors, including environmental and dietary factors or infectious agents. Long-term hepatitis B and C infections can cause liver fibrosis. Sustained over-consumption of alcohol or a high fat/sugar diet can also lead to cirrhosis of the liver. Similarly, diabetes can damage and scar the kidneys, leading to loss of function.

IPF is one of seven interstitial lung diseases the cause of which is unknown. Environmental factors such as radiation exposure or particles may play a role. Individuals who smoke are also at higher risk of this disease. Once diagnosed, the lifespan of patients is very short, with the average survival time being 2-5 years.

Treatment of fibrotic disease typically includes anti-inflammatory and immunosuppressive agents, but these are of little benefit to the patient. The lack of efficacy of these treatments contributed to the reconsideration of IPF and fibrotic disease in general as an aberrant response to wound healing and not an inflammatory condition. Pirfenidone is a small-molecule drug that was approved for use in the treatment of IPF in Japan in 2008 and Europe in 2011, which is likely to work via multiple mechanisms of action. To date, no targeted therapies and no antibody therapies have been approved for fibrotic indications.

Therefore, there is currently an unmet medical need for improved treatment of fibrotic disease. For example, for IPF there is a 3-year survival rate of 50% and a 5-year survival rate of only 20% and transplantation is required in about 20% of cases.

SUMMARY OF THE DISCLOSURE

In one aspect there is provided an anti-CSF-1R antibody or binding fragment thereof comprising a heavy chain, wherein the variable domain of the heavy chain comprises at least one of a CDR having the sequence given in SEQ ID NO: 4 for CDR-H1, a CDR having the sequence given in SEQ ID NO: 5 for CDR-H2 and a CDR having the sequence given in SEQ ID NO: 6 for CDR-H3, for example, wherein CDR-H1 is SEQ ID NO: 4, CDR-H2 is SEQ ID NO: 5 and CDR-H3 is SEQ ID NO: 6.

In one aspect the antibodies or binding fragments according to the present disclosure comprise a light chain, wherein the variable domain of the light chain comprises at least one of a CDR having the sequence given in SEQ ID NO: 1 for CDR-L1, a CDR having the sequence given in SEQ ID NO: 2 for CDR-L2 and a CDR having the sequence given in SEQ ID NO: 3 for CDR-L3, for example, wherein CDR-L1 is SEQ ID NO: 1, CDR-L2 is SEQ ID NO: 2 and CDR-L3 is SEQ ID NO: 3.

The antibodies of the disclosure have a high affinity for CSF-1R, are able to block binding of ligands to CSF-1R, are non-activating to CSF-1R and do not cause internalization of CSF-1R.

The disclosure also extends to a polynucleotide, such as DNA, encoding an antibody or fragment as described herein.

Also provided is a host cell comprising said polynucleotide.

Methods of expressing an antibody or binding fragment thereof are provided herein.

The present disclosure also relates to pharmaceutical compositions comprising said antibodies or binding fragments thereof.

In one embodiment there is provided a method of treatment comprising administering a therapeutically effective amount of an antibody, fragment or composition as described herein.

The present disclosure also extends to an antibody, binding fragment or composition according to the present disclosure for use in treatment, particularly in the treatment of cancer and/or fibrotic disease.

DETAILS OF THE DISCLOSURE

In one embodiment the antibodies provided by the present invention are capable of blocking ligand binding to CSF-1R. Blocking as employed herein refers to physically blocking, such as occluding the receptor, but will also include where the antibody or fragment binds an epitope that causes, for example, a conformational change which means that the natural ligand to the receptor no longer binds (referred to herein as allosteric blocking or allosteric inhibition). In one embodiment the antibodies of the present disclosure bind all isotypes of CSF-1R, for example, those with variations in the ECD domain, such as V23G, A245S, H247P, V279M and combinations of two, three or four of said variations.

Assays suitable for determining the ability of an antibody to block CSF-1R are described in the Examples herein. CSF-1 and IL-34 are both ligands for CSF-1R and the antibodies of the invention preferably inhibit the activity both CSF-1 and IL-34 in a functional cellular screen. The antibodies according to the present invention also preferably do not cause CSF-1R activation and/or CSF-1R internalisation. The antibodies according to the present invention also preferably selectively deplete the non-classical population of monocytes in vivo.

Non-classical monocytes generally refers to monocytes with low expression of CD14 and high expression of CD16. This population of monocytes are thought to be pre-cursors of tumor-associated macrophages.

The antibody molecules of the present invention suitably have a high binding affinity. Affinity may be measured using any suitable method known in the art, including techniques such as surface plasmon resonance, for example BIAcore, as described in the Examples herein, using isolated natural or recombinant CSF-1R or a suitable fusion protein/polypeptide. In one example affinity is measured using a recombinant human CSF-1R extracellular domain as described in the Examples herein. In one example the recombinant human CSF-1R extracellular domain used is a monomer. Suitably, the antibody molecules of the present invention have a binding affinity for isolated human CSF-1R of about 1 nM or less than 1 nM. In one embodiment the antibody molecule of the present invention has a binding affinity of about 500 pM or lower. In one embodiment the antibody molecule of the present invention has a binding affinity of about 250 pM or lower. In one embodiment the antibody molecule of the present invention has a binding affinity of about 200 pM or lower. In one embodiment the present invention provides an anti-CSF-1R antibody with a binding affinity of about 100 pM or lower. In one embodiment the present invention provides a humanised anti-CSF-1R antibody with a binding affinity of about 100 pM or lower, preferably about 10 pM or lower, more preferably about 5 pM or lower. In another embodiment the present invention provides a humanised anti-CSF-1R antibody with a binding affinity of about 100 pM or lower, preferably about 10 pM or lower, more preferably about 5 pM or lower The lower the numerical value of the affinity, the higher the affinity of the antibody or fragment for the antigen.

Human CSF-1R as employed herein refers to the human protein named CSF-1R or a biological active fragment thereof, for example as given in SEQ ID NO: 39 or registered in UniProt under the number P07333. Of course the expressed mature protein does not comprise the signal sequence because the latter is cleaved post-translation.

The present inventors have provided new anti-CSF-1R antibodies, including humanised antibodies. The antibodies were generated from immunisation of rats with rat fibroblasts that were transfected with a vector expressing a CSF-1R extracellular domain. Primary screening of supernatants for human CSF-1R binding of the antibody identified approximately 1000 wells containing antibody with anti-CSF-1R activity. Secondary screening for antibodies capable of preventing human CSF-1 binding to human CSF-1R identified 88 positive wells. Tertiary screening for antibodies capable of preventing CSF-1-dependent survival of primary human monocytes identified 18 positive wells. The variable regions of these 18 positive wells were cloned, which led to successful cloning of 14 antibodies, and subsequent expression provided 9 chimeric anti-CSF-1R antibodies which expressed at sufficient levels and were capable of inhibiting CSF-1 binding. These 9 antibodies were sequenced, found to all have unique sequences, and were used for further study.

The 9 anti-CSF-1R chimeric antibodies were assessed for ligand-blocking activity and ability to inhibit CSF-1 and IL-34 mediated monocyte survival. Four of the antibodies were prioritised for further investigation because they demonstrated complete inhibition of CSF-1 binding and high levels of inhibition of monocyte survival. These four anti-CSF-1R chimeric antibodies were tested for their activity in a number of in vitro assays to assess affinity, inhibition of CSF-1 binding, cross-reactivity with rhesus monkey, cynomolgus monkey and canine CSF-1R, CSF-1R internalization and CSF-1R activation. The four anti-CSF-1R antibodies were also humanised and affinity of the humanised grafts was measured. The humanisation of two of the anti-CSF-1R antibodies generated fully humanised antibodies (no rat donor residues present) with affinity ($K_D$) equivalent to the parental chimeric antibody and a Tm indicating the antibody having suitable thermal stability. In contrast, the other two humanised anti-CSF-1R antibodies had a reduced affinity for CSF-1R, relative to the chimeric antibody, and the Tm was lower. For these reasons, only the fully humanised grafts of two of the antibodies which retained affinity were expressed on a larger scale for further analysis.

Further analysis of the fully humanised grafts of these two antibodies was carried out and an MCP-1 inhibition assay, where the inhibition of CSF-1R signalling by an antibody that blocks CSF-1 binding caused a reduction in the levels of MCP-1 secretion. This assay surprisingly revealed that fully humanised grafts exhibited reduced activity compared to the chimeric antibody. A series of experiments on one of the preferred antibodies, termed Ab969, was carried out to reveal why the fully humanised graft exhibited this reduced activity. A number of intermediate humanised grafts of Ab969 were generated and tested in the MCP-1 inhibition assay. It was found that grafts which contained the variable light chain donor residue Y71 generally showed activity in the MCP-1 inhibition assay comparable to that of the chimeric Ab969. It was hypothesised that this difference in activity of the various antibody grafts in the MCP-1 inhibition assay was due to a change in the antibody on-rate (decreased $K_a$) compared to the chimeric Ab969.

Comparing the thermal stability analysis of Ab969 with other anti-CSF-1R antibodies, e.g., anti-CSF-1R antibody Ab970, suggests that Ab969 may be more stable.

Further biophysical analysis of humanised grafts of Ab969 revealed that some grafts precipitated when the antibody was concentrated. It was shown that a substitution of the lysine residue at position 38 in the light chain, for example glutamine, led to improved physical stability.

Accordingly, one antibody graft of Ab969, Ab969.g2 (also referred to as Ab969), was selected for further in vitro characterisation studies. In addition to the advantageous high binding affinity to CSF-1R, high thermal stability and high physical stability, the antibody demonstrated good inhibition of IL-34-dependent monocyte activation and was also found to be capable of binding to SNP variants of CSF-1R. Ab969.g2 was also used for pharmacodynamic marker analysis in a cynomolgus monkey, where it was shown to bind CSF-1R, block CSF-1 binding and selectively deplete the non-classical population of cynomolgus monkey monocytes in vivo, which are precursor cells of tumour-associated macrophages.

Accordingly, in one embodiment, the present invention provides an antibody comprising a heavy chain and/or a light chain, wherein the heavy chain and/or light chain comprises at least one CDR derived from the anti-CSF-1R antibody 969.2.

Ab969.2 is a full-length humanised IgG4 molecule; the light chain comprises a human kappa chain constant region (Km3 allotype) and the heavy chain comprises a human gamma-4 heavy chain constant region with the hinge-stabilising mutation S241P (Angal et al., 1993). A potential DG isomerisation motif is present within the light chain variable region at the junction of CDR-L2 and the framework. The sequences of Ab969.2 full antibody heavy and light chains are shown in SEQ ID NOs: 27 and 19.

The residues in antibody variable domains are conventionally numbered according to a system devised by Kabat et al., 1987. This system is set forth in Kabat et al., 1987, Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering, corresponding to a shortening of, or insertion into, a structural component, whether framework or complementarity-determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, 1987, A. M., J. Mol. Biol., 196:901-917), the loop equivalent to CDR-H1 extends from residue 26 to residue 32. Thus, unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

Antibodies for use in the present disclosure may be obtained using any suitable method known in the art. The CSF-1R polypeptide/protein, including fusion proteins and cells (recombinantly or naturally) expressing the polypeptide, can be used to produce antibodies which specifically recognise CSF-1R. The polypeptide may be the 'mature' polypeptide or a biologically active fragment or derivative thereof. The human protein is registered in UniProt under the number P07333.

Polypeptides for use to immunize a host may be prepared by processes well-known in the art from genetically engineered host cells comprising expression systems or they may be recovered from natural biological sources. In the present application, the term "polypeptides" includes peptides, polypeptides and proteins. These are used interchangeably unless otherwise specified. The CSF-1R polypeptide may in some instances be part of a larger protein, such as a fusion protein, for example fused to an affinity tag or similar.

Antibodies generated against the CSF-1R polypeptide may be obtained, where immunisation of an animal is necessary, by administering the polypeptides to an animal, preferably a non-human animal, using well-known and routine protocols (see, for example, Handbook of Experimental Immunology, D. M. Weir (ed.), Vol. 4, Blackwell Scientific Publishers, Oxford, England, 1986). Many warm-blooded animals, such as rabbits, mice, rats, sheep, cows, camels or pigs, may be immunized. However, mice, rabbits, pigs and rats are generally most suitable.

Monoclonal antibodies may be prepared by any method known in the art, such as the hybridoma technique (Kohler and Milstein, 1975, Nature, 256:495-497), the trioma technique, the human B-cell hybridoma technique (Kozbor et al., 1983, Immunology Today, 4:72) and the EBV-hybridoma technique (Cole et al., 1985, Monoclonal Antibodies and Cancer Therapy, pp. 77-96, Alan R. Liss, Inc.).

Antibodies may also be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA, 93:7843-7848; WO92/02551; WO04/051268; and WO04/106377.

Screening for antibodies can be performed using assays to measure binding to human CSF-1R and/or assays to measure the ability to block ligand binding to the receptor. Examples of suitable assays are described in the Examples herein.

Specific as used herein is intended to refer to an antibody that only recognises the antigen to which it is specific, or an antibody that has significantly higher binding affinity to the antigen to which it is specific compared to binding to antigens to which it is non-specific, for example, at least 5, 6, 7, 8, 9, or 10 times higher binding affinity.

The amino acid sequences and the polynucleotide sequences of certain antibodies according to the present disclosure are provided in FIGS. 1 and 2.

In one aspect of the invention the antibody is an anti-CSF-1R antibody or binding fragment thereof comprising a heavy chain, wherein the variable domain of the heavy chain comprises at least one of a CDR having the sequence given in SEQ ID NO: 4 for CDR-H1, a CDR having the sequence given in SEQ ID NO: 5 for CDR-H2 and a CDR having the sequence given in SEQ ID NO: 6 for CDR-H3. Preferably the variable domain of the heavy chain comprises the sequence given in SEQ ID NO: 4 for CDR-H1, the sequence given in SEQ ID NO: 5 for CDR-H2 and the sequence given in SEQ ID NO: 6 for CDR-H3.

In a second aspect of the invention the antibody is an anti-CSF-1R antibody or binding fragment thereof comprising a light chain, wherein the variable domain of the light chain comprises at least one of a CDR having the sequence given in SEQ ID NO: 1 for CDR-L1, a CDR having the sequence given in SEQ ID NO: 2 for CDR-L2 and a CDR having the sequence given in SEQ ID NO: 3 for CDR-L3. Preferably the variable domain of the light chain comprises the sequence given in SEQ ID NO: 1 for CDR-H1, the sequence given in SEQ ID NO: 2 for CDR-H2 and the sequence given in SEQ ID NO: 3 for CDR-H3.

In one embodiment the antibody of the invention is an anti-CSF-1R antibody or binding fragment thereof comprising a heavy chain as defined above and additionally comprising a light chain wherein the variable domain of the light chain comprises at least one of a CDR having the sequence given in SEQ ID NO: 1 for CDR-L1, a CDR having the sequence given in SEQ ID NO: 2 for CDR-L2 and a CDR having the sequence given in SEQ ID NO: 3 for CDR-L3. The variable domain of the light chain preferably comprises the sequence given in SEQ ID NO: 1 for CDR-L1, the sequence given in SEQ ID NO: 2 for CDR-L2 and the sequence given in SEQ ID NO: 3 for CDR-L3.

In one embodiment, at least one amino acid is replaced with a conservative substitution in one or more CDRs selected from the group consisting independently of:
  any one of CDR-H1, CDR-H2, CDR-H3, CDR-L1, CDR-L2, CDR-L3;
  any one of the combinations CDR-H1 and H2, CDR-H1 and H3, CDR-H1 and L1, CDR-H1 and L2, CDR-H1 and L3, CDR-H2 and H3, CDR-H2 and L1, CDR-H2 and L2, CDR-H2 and L3, CDR-H3 and L1, CDR-H3 and L2, CDR-H3 and L3, CDR-L1 and L2, CDR-L1 and L3, CDR-L2 and L3;
  CDR-H1, H2 and H3, CDR-H1, H2 and L1, CDR-H1, H2 and L2, CDR-H1, H2 and L3, CDR-H2, H3 and L1, CDR-H2, H3 and L2, CDR-H2, H3 and L3, CDR-H3, L1 and L2, CDR-H3, L1 and L3, CDR-L1, L2, L3;
  any one of the combinations CDR-H1, H2, H3 and L1, CDR-H1, H2, H3 and L2, CDR-H1, H2, H3 and L3, CDR-H2, H3, L1 and L2, CDR-H2, H3, L2 and L3, CDR-H3, L1, L2 and L3, CDR-L1, L2, L3 and H1, CDR-L1, L2, L3 and H2, CDR-L1, L2, L3 and H3, CDR-L2, L3, H1 and H2,
  CDR-H1, H2, H3, L1 and L2, CDR-H1, H2, H3, L1 and L3, CDR-H1, H2, H3, L2 and L3, CDR-L1, L2, L3, H1 and H2, CDR-L1, L2, L3, H1 and H3, CDR-L1, L2, L3, H2 and H3; and
  the combination CDR-H1, H2, H3, L1, L2 and L3.

In one embodiment, a domain of the heavy chain disclosed herein includes the sequence with 1, 2, 3 or 4 conservative amino acid substitutions, for example, wherein the substitutions are in the framework.

In one embodiment, the framework of the heavy chain variable region comprises 1, 2, 3, or 4 amino acids which have been inserted, deleted, substituted or a combination thereof. In one embodiment, the substituted amino acid is a corresponding amino acid from the donor antibody.

In one embodiment, a light variable region disclosed herein includes the sequence with 1, 2, 3 or 4 conservative amino acid substitutions, for example, wherein the substitutions are in the framework.

In one embodiment, the framework of the light chain variable region comprises 1, 2, 3 or 4 amino acids which have been inserted, deleted, substituted or a combination thereof. In one embodiment the substituted amino is a corresponding amino acid from a donor antibody.

In one aspect of the present invention, there is provided an anti-CSF-1R antibody or binding fragment thereof, wherein the variable domain of the heavy chain comprises three CDRs and the sequence of CDR-H1 has at least 60%, 70%, 80%, 90% or 95% identity or similarity to the sequence given in SEQ ID NO: 4, the sequence of CDR-H2 has at least 60%, 70%, 80%, 90% or 95% identity or similarity to the sequence given in SEQ ID NO: 5 and the sequence of CDR-H-3 has at least 60%, 70%, 80%, 90% or 95% identity or similarity to the sequence given in SEQ ID NO: 6. Preferably, the anti-CSF-1R antibody or binding fragment thereof additionally comprises a light chain, wherein the variable domain of the light chain comprises three CDRs and the sequence of CDR-L1 has at least 60%, 70%, 80%, 90% or 95% identity or similarity to the sequence given in SEQ ID NO: 1, the sequence of CDR-L2 has at least 60%, 70%, 80%, 90% or 95% identity or similarity to the sequence given in SEQ ID NO: 2 and the sequence of CDR-L3 has at least 60% identity or similarity to the sequence given in SEQ ID NO: 3.

In one embodiment a variable region is provided with at least 60%, 70%, 80%, 90% or 95% identity or similarity to a variable region sequence disclosed herein. In another embodiment there is provided an anti-CSF-1R antibody which competes with the binding of an antibody or fragment of the invention for binding to the CSF-1R receptor, preferably the extracellular domain of the CSF-1R receptor, more specifically the CSF-1R receptor of SEQ ID NO: 35, 36, 37, 38 and/or 39 or the sequence in the UniProt database entry P07333, in particular the extracellular domain of the CSF-1R receptor of SEQ ID NO: 36 or the 498 amino acids of the extracellular domain disclosed in the UniProt database entry P07333 (amino acids 20 to 517 of P07333).

In one embodiment there is provided an anti-CSF-1R antibody which cross-blocks the binding of an antibody comprising the 6 CDRs given in sequence SEQ ID NO: 1 for CDR-L1, SEQ ID NO: 2 for CDR-L2, SEQ ID NO: 3 for CDR-L3, SEQ ID NO: 4 for CDR-H1, SEQ ID NO: 5 for CDR-H2 and SEQ ID NO: 6 for CDR-H3, for example, with affinity of 100 pM or less, in particular wherein the cross-blocking is allosteric.

In another embodiment, there is provided an anti-CSF-1R-antibody or binding fragment thereof which inhibits or overlaps with the binding of CSF-1 and/or IL-34 to the extracellular domain of the CSF-1R receptor.

In one embodiment there is provided an anti-CSF-1R antibody which cross-blocks the binding of an antibody comprising the 6 CDRs given in sequence SEQ ID NO: 1 for CDR-L1, SEQ ID NO: 2 for CDR-L2, SEQ ID NO: 3 for CDR-L3, SEQ ID NO: 4 for CDR-H1, SEQ ID NO: 5 for CDR-H2 and SEQ ID NO: 6 for CDR-H3, for example, with affinity of 100 pM or less, in particular wherein the antibody cross-blocks the binding by binding the same epitope as the antibody which it blocks.

In one embodiment an antibody or binding fragment thereof is provided wherein a C-terminal residue of the antibody sequence is cleaved, for example, the C-terminal residue of a heavy chain sequence, for example, a terminal lysine. In one embodiment the amino acid is cleaved from a sequence disclosed herein. Generally the cleavage results from post-translation modifications of the expressed antibody or binding fragment.

In another embodiment the anti-CSF-1R antibody of any of the embodiments supra or infra is provided wherein the C-terminal lysine of the heavy chain sequence given in SEQ ID NO: 27 or SEQ ID NO: 29 is missing or deleted. Missing or deleted C-terminal lysine, e.g., position 453 of SEQ ID NO: 27 or position 472 of SEQ ID NO: 30, can be achieved, for example, by expression of the anti-CSF-1R antibody in an expression system without coding the terminal lysine. Alternatively, the deletion of a C-terminal residue, such as lysine, may be effected as a post-translational modification.

In one embodiment the antibody or binding fragment according to the invention is humanised.

As used herein, the term "humanised antibody" refers to an antibody or antibody molecule wherein the heavy and/or light chain contains one or more CDRs (including, if desired, one or more modified CDRs) from a donor antibody (e.g., a murine monoclonal antibody) grafted into a heavy and/or light chain variable region framework of an acceptor antibody (e.g., a human antibody) (see, e.g., U.S. Pat. No. 5,585,089; WO91/09967). For a review, see Vaughan et al., Nature Biotechnology, 1998, 16:535-539. In one embodiment, rather than the entire CDR being transferred, only one or more of the specificity-determining residues from any one of the CDRs described hereinabove are transferred to the human antibody framework (see, for example, Kashmiri et al., 2005, Methods, 36:25-34). In one embodiment only the specificity-determining residues from one or more of the CDRs described hereinabove are transferred to the human antibody framework. In another embodiment only the specificity-determining residues from each of the CDRs described hereinabove are transferred to the human antibody framework. When the CDRs or specificity-determining residues are grafted, any appropriate acceptor variable region framework sequence may be used with regard to the class/type of the donor antibody from which the CDRs are derived, including mouse, primate and human framework regions.

Suitably, the humanised antibody according to the present invention has a variable domain comprising human acceptor framework regions as well as one or more of the CDRs provided specifically herein. Thus, provided in one embodiment is a humanised antibody which binds human CSF-1R, wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: http://vbase.mrc-cpe.cam.ac.uk/.

In a humanised antibody of the present invention, the acceptor heavy and light chains do not necessarily need to be derived from the same antibody and may, if desired, comprise composite chains having framework regions derived from different chains.

In one embodiment a human framework comprises 1, 2, 3, or 4 amino acid substitutions, additions or deletions, for example, 1, 2, 3 or 4 conservative substitutions or substitutions of donor residues.

In one embodiment the sequence employed as a human framework is 80%, 85%, 90%, 95% or more similar or identical to a sequence disclosed herein.

One such suitable framework region for the heavy chain of the humanised antibody of the present invention is derived from the human sub-group VH2 sequence 3-1 2-70 together with the JH3 J-region (SEQ ID NO: 33).

Accordingly, in one example there is provided a humanised antibody comprising the sequence given in SEQ ID NO:

4 for CDR-H1, the sequence given in SEQ ID NO: 5 for CDR-H2 and the sequence given in SEQ ID NO: 6 for CDR-H3, wherein the heavy chain framework region is derived from the human subgroup VH3 sequence 1-3 3-07 together with JH4.

In one example the heavy chain variable domain of the antibody comprises the sequence given in SEQ ID NO: 23.

A suitable framework region for the light chain of the humanised antibody of the present invention is derived from the human germline sub-group VK1 2-1-(1) O12 together with the JK4 J-region (SEQ ID NO: 31).

Accordingly, in one example there is provided a humanised antibody comprising the sequence given in SEQ ID NO: 1 for CDR-L1, the sequence given in SEQ ID NO: 2 for CDR-L2 and the sequence given in SEQ ID NO: 3 for CDR-L3, wherein the light chain framework region is derived from the human subgroup VK1 2-1-(1) O12 plus the JK4 J-region.

In one example the light chain variable domain of the antibody comprises the sequence given in SEQ ID NO: 15.

In a humanised antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residues found at the same position in the donor antibody (see Reichmann et al., 1998, Nature, 332:323-324). Such changes should be kept to the minimum necessary to recover the affinity of the donor antibody. A protocol for selecting residues in the acceptor framework regions which may need to be changed is set forth in WO91/09967.

Accordingly, in one example there is provided a humanised antibody, wherein at least the residue at position 78 of the variable domain of the heavy chain (Kabat numbering) is a donor residue. In one embodiment residue 78 of the heavy chain variable domain is replaced with alanine.

Donor residue as employed herein refers to a residue from the non-human antibody (e.g., murine antibody) which donated the CDRs.

In one embodiment there is provided a humanised antibody wherein the heavy chain variable domain does not contain any donor residues.

Accordingly, in one example there is provided a humanised antibody, wherein at least one of the residues at positions 38, 71 and 87 of the variable domain of the light chain (Kabat numbering) are donor residues. In one embodiment one of the residues selected from the residues at positions 38, 71 and 87 of the variable domain of the light chain (Kabat numbering) is a donor residue. In one embodiment two of the residues selected from the residues at positions 38, 71 and 87, for example, 38 and 71, or 38 and 87, or 71 and 87, of the variable domain of the light chain (Kabat numbering) are donor residues. In one embodiment the three residues at positions 38, 71 and 87 of the variable domain of the light chain (Kabat numbering) are donor residues.

In one embodiment residue 38 of the light chain variable domain is replaced with lysine. In an alternative embodiment residue 38 of the light chain variable domain is replaced with glutamine.

In one embodiment residue 71 of the light chain variable domain is replaced with tyrosine.

In one embodiment residue 87 of the light chain variable domain is replaced with phenylalanine.

In one embodiment there is provided a humanised antibody wherein only residue 71 of the light chain variable region is a donor residue, preferably tyrosine.

In a particular embodiment, the present invention provides an anti-CSF-1R antibody or binding fragment thereof having a heavy chain comprising the heavy chain variable domain sequence given in SEQ ID NO: 23 and a light chain comprising the light chain variable domain sequence given in SEQ ID NO: 15.

In a further aspect of the present invention, an anti-CSF-1R antibody or binding fragment thereof is provided which binds CSF-1R, preferably the extracellular domain of CSF-1R, most preferably the extracellular domain of human CSF-1R, wherein the antibody or binding fragment comprises the light chain variable domain of SEQ ID NO: 15 and the heavy chain variable domain of SEQ ID NO: 23, preferably wherein the antibody or binding fragment thereof is a monoclonal antibody, is an antibody of the IgG1-, IgG2-, or IgG4-type, or is a Fab, modified Fab, Fab', modified Fab', F(ab')$_2$, Fv, single domain antibody (e.g., VH or VL or VHH), scFv, bi-, tri- or tetravalent antibody, Bis-scFv, diabody, triabody or tetrabody.

In one embodiment the disclosure provides an antibody sequence which is 80% similar or identical to a sequence disclosed herein, for example 85%, 90%, 91%, 92%, 93%, 94%, 95% 96%, 97%, 98% or 99% over part or whole of the relevant sequence. In one embodiment the relevant sequence is SEQ ID NO: 15. In one embodiment the relevant sequence is SEQ ID NO: 23.

"Identity", as used herein, indicates that at any particular position in the aligned sequences, the amino acid residue is identical between the sequences. "Similarity", as used herein, indicates that at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains).

Degrees of identity and similarity can be readily calculated (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M. and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., Springer, New York, 1991; the BLAST™ software available from NCBI (Altschul, S. F. et al., 1990, J. Mol. Biol., 215:403-410; Gish, W. and States, D. J., 1993, Nature Genet. 3:266-272; Madden, T. L. et al., 1996, Meth. Enzymol., 266:131-141; Altschul, S. F. et al., 1997, Nucleic Acids Res., 25:3389-3402; Zhang, J. and Madden, T. L., 1997, Genome Res., 7:649-656).

The antibody molecules of the present invention may comprise a complete antibody molecule having full-length heavy and light chains or a binding fragment thereof and may be, but are not limited to, Fab, modified Fab, Fab', modified Fab', F(ab')₂, Fv, single-domain antibodies (e.g., VH or VL or VHH), scFv, bi-, tri- or tetravalent antibodies, Bis-scFv, diabodies, triabodies, tetrabodies and epitope-binding fragments of any of the above (see, for example, Holliger and Hudson, 2005, Nature Biotech., 23(9):1126-1136; Adair and Lawson, 2005, Drug Design Reviews—Online, 2(3):209-217). The methods for creating and manufacturing these antibody fragments are well-known in the art (see, for example, Verma et al., 1998, Journal of Immunological Methods, 216:165-181). Other antibody fragments for use in the present invention include the Fab and Fab' fragments described in WO05/003169, WO05/003170 and WO05/003171. Multi-valent antibodies may comprise multiple specificities, e.g., bispecific, or may be monospecific (see, for example, WO92/22853, WO05/113605, WO2009/040562 and WO2010/035012).

Binding fragment of an antibody as employed herein refers to a fragment capable of binding an antigen with affinity to characterise the fragment as specific for the antigen.

In one embodiment the antibody according to the present disclosure is provided as CSF-1R binding antibody fusion protein, which comprises an immunoglobulin moiety, for example a Fab or Fab' fragment, and one or two single-domain antibodies (sdAb) linked directly or indirectly thereto, for example, as described in WO2009/040562, WO2010/035012, WO2011/030107, WO2011/061492 and WO2011/086091, all incorporated herein by reference.

In one embodiment the fusion protein comprises two domain antibodies, for example as a variable heavy (VH) and variable light (VL) pairing, optionally linked by a disulphide bond.

In one embodiment the Fab or Fab' element of the fusion protein has the same or similar specificity to the single-domain antibody or antibodies. In one embodiment the Fab or Fab' has a different specificity to the single-domain antibody or antibodies, i.e., the fusion protein is multivalent. In one embodiment a multivalent fusion protein according to the present invention has an albumin binding site, for example a VH/VL pair therein provides an albumin binding site.

The constant region domains of the antibody molecule of the present invention, if present, may be selected with regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes, when the antibody molecule is intended for therapeutic uses and antibody effector functions are required. Alternatively, IgG2 and IgG4 isotypes may be used when the antibody molecule is intended for therapeutic purposes and antibody effector functions are not required.

In a specific embodiment, the antibody of the present invention is an IgG2 or IgG4 antibody.

It will be appreciated that sequence variants of these constant region domains may also be used. For example IgG4 molecules in which the serine at position 241 has been changed to proline as described in Angal et al. (1993, Molecular Immunology, 30:105-108) may be used. Accordingly, in the embodiment where the antibody is an IgG4 antibody, the antibody may include the mutation S241P.

It will also be understood by one skilled in the art that antibodies may undergo a variety of post-translational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R. J., 1995, Journal of Chromatography, 705:129-134, 1995). Accordingly, the C-terminal lysine of the antibody heavy chain may be absent.

In one embodiment the antibody heavy chain comprises a CH1 domain and the antibody light chain comprises a CL domain, either kappa or lambda.

In one embodiment the antibody heavy chain comprises a CH1 domain, a CH2 domain and a CH3 domain and the antibody light chain comprises a CL domain, either kappa or lambda.

An antibody provided by the present invention has a heavy chain comprising the sequence given in SEQ ID NO: 27 and a light chain comprising the sequence given in SEQ ID NO: 19. Also provided is an anti-CSF-1R antibody or binding fragment thereof, in which the heavy and light chains are at least 80% (preferably 85%, 90%, 95% or 98%) identical or similar to a heavy chain comprising the sequence given in SEQ ID NO: 27 and a light chain comprising the sequence given in SEQ ID NO: 19. In one embodiment, the light chain has or consists of the sequence given in SEQ ID NO: 19 and the heavy chain has or consists of the sequence given in SEQ ID NO: 27. In another embodiment, the light chain has or consists of the sequence of SEQ ID NO: 19 and the heavy chain has or consists of the sequence of SEQ ID NO: 27, wherein the amino acid lysine at position 453 of SEQ ID NO: 27 is missing or deleted.

Also provided by the present invention is a specific region or epitope of human CSF-1R which is bound by an antibody provided by the present invention, in particular an antibody 969.g2 comprising the heavy chain sequence gH2 (SEQ ID NO: 27) and/or the light chain sequence gL7 (SEQ ID NO: 19).

This specific region or epitope of the human CSF-1R polypeptide can be identified by any suitable epitope-mapping method known in the art in combination with any one of the antibodies provided by the present invention. Examples of such methods include screening peptides of varying lengths derived from CSF-1R for binding to the antibody of the present invention with the smallest fragment that can specifically bind to the antibody containing the sequence of the epitope recognised by the antibody (for example, a peptide in the region of about 5 to 20, preferably about 7, amino acids in length). The CSF-1R peptides may be produced synthetically or by proteolytic digestion of the CSF-1R polypeptide. Peptides that bind the antibody can be identified by, for example, mass spectrometric analysis. In another example, NMR spectroscopy or X-ray crystallography can be used to identify the epitope bound by an antibody of the present invention. Once identified, the epitopic fragment which binds an antibody of the present invention can be used, if required, as an immunogen to obtain additional antibodies which bind the same epitope.

Biological molecules, such as antibodies or fragments, contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or solvent-accessible surface thereof carries no net electrical charge. In one example, the CSF-1R antibody and fragments of the invention may be engineered to have an appropriate isoelectric point. This may lead to antibodies and/or fragments with more robust properties, in particular suitable solubility and/or stability profiles and/or improved purification characteristics.

Thus, in one aspect, the invention provides a humanised CSF-1R antibody engineered to have an isoelectric point different from that of the originally identified antibody. The antibody may, for example, be engineered by replacing an amino acid residue, such as replacing an acidic amino acid residue with one or more basic amino acid residues. Alternatively, basic amino acid residues may be introduced or acidic amino acid residues can be removed. Alternatively, if the molecule has an unacceptably high pI value, acidic residues may be introduced to lower the pI, as required. It is important that when manipulating the pI, care must be taken to retain the desirable activity of the antibody or fragment. Thus, in one embodiment, the engineered antibody or fragment has the same or substantially the same activity as the "unmodified" antibody or fragment.

Programs such as ** ExPASY (see Worldwide Web sites expasy.ch/tools/pi_tool.html and iut-arles.up.univ-mrs.fr/w3bb/d_abim/compo-p.html) may be used to predict the isoelectric point of the antibody or fragment.

It will be appreciated that the affinity of antibodies provided by the present invention may be altered using any suitable method known in the art. The present invention therefore also relates to variants of the antibody molecules of the present invention, which have an improved affinity for CSF-1R. Such variants can be obtained by a number of affinity maturation protocols, including mutating the CDRs (Yang et al., 1995, J. Mol. Biol., 254:392-403), chain shuffling (Marks et al., 1992, Bio/Technology, 10:779-783), use of mutator strains of E. coli (Low et al., 1996, J. Mol. Biol., 250:359-368), DNA shuffling (Patten et al., 1997, Curr. Opin. Biotechnol., 8:724-733), phage display (Thompson et al., 1996, J. Mol. Biol., 256:77-88) and sexual PCR (Crameri et al., 1998, Nature, 391:288-291). Vaughan et al. (supra) discusses these methods of affinity maturation.

If desired, an antibody for use in the present invention may be conjugated to one or more effector molecule(s). It will be appreciated that the effector molecule may comprise a single effector molecule or two or more such molecules linked so as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well-known in the art (see Hellstrom et al., Controlled Drug Delivery, 2nd Ed., Robinson et al., eds., 1987, pp. 623-53; Thorpe et al., 1982, Immunol. Rev., 62:119-58; and Dubowchik et al., 1999, Pharmacology and Therapeutics, 83:67-123). Particular chemical procedures include, for example, those described in WO93/06231, WO92/22583, WO89/00195, WO89/01476 and WO03/031581. Alternatively, where the effector molecule is a protein or polypeptide, the linkage may be achieved using recombinant DNA procedures, for example as described in WO86/01533 and EP0392745.

The term effector molecule as used herein includes, for example, antineoplastic agents, drugs, toxins, biologically active proteins, for example enzymes, other antibodies or antibody fragments, synthetic or naturally occurring polymers, nucleic acids and fragments thereof, e.g., DNA, RNA and fragments thereof, radionuclides, particularly radioiodide, radioisotopes, chelated metals, nanoparticles and reporter groups, such as fluorescent compounds or compounds which may be detected by NMR or ESR spectroscopy.

Examples of effector molecules may include cytotoxins or cytotoxic agents, including any agent that is detrimental to (e.g., kills) cells. Examples, include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxyanthracenedione, mitoxantrone, mithramycin, actinomycin D, 1-dihydrotestosterone, glucocorticoids, procaine, tetracaine, lidocaine, propranolol, and puromycin and analogs or homologs thereof.

Effector molecules also include, but are not limited to, antimetabolites (e.g., methotrexate, 6-mercaptopurine, 6-thioguanine, cytarabine, 5-fluorouracil decarbazine), alkylating agents (e.g., mechlorethamine, thiotepa and chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, anthramycin (AMC), calicheamicins or duocarmycins), and anti-mitotic agents (e.g., vincristine and vinblastine).

Other effector molecules may include chelated radionuclides, such as $^{111}$In and $^{90}$Y, $Lu^{177}$, $Bismuth^{213}$, $Californium^{252}$, $Iridium^{192}$ and $Tungsten^{188}$/$Rhenium^{188}$, or drugs such as, but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, and transferases. Proteins, polypeptides and peptides of interest include, but are not limited to, immunoglobulins, toxins such as abrin, ricin A, *pseudomonas* exotoxin, or diphtheria toxin, proteins such as insulin, tumour necrosis factor, α-interferon, β-interferon, nerve growth factor, platelet-derived growth factor or tissue plasminogen activator, a thrombotic agent or an anti-angiogenic agent, e.g., angiostatin or endostatin, or a biological response modifier such as a lymphokine, interleukin-1 (IL-1), interleukin-2 (IL-2), nerve growth factor (NGF) or other growth factors and immunoglobulins.

Other effector molecules may include detectable substances useful, for example, in diagnosis. Examples of detectable substances include various enzymes, prosthetic groups, fluorescent materials, luminescent materials, bioluminescent materials, radioactive nuclides, positron-emitting metals (for use in positron emission tomography), and non-radioactive paramagnetic metal ions. See, generally, U.S. Pat. No. 4,741,900 for metal ions which can be conjugated to antibodies for use as diagnostics. Suitable enzymes include horseradish peroxidase, alkaline phosphatase, beta-galactosidase, and acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin-binding proteins or albumin-binding compounds such as those described in WO05/117984.

In one embodiment a half-life provided by an effector molecule which is independent of CSF-1R is advantageous.

Where the effector molecule is a polymer it may, in general, be a synthetic or a naturally-occurring polymer, for example, an optionally substituted straight or branched chain polyalkylene, polyalkenylene or polyoxyalkylene polymer or a branched or unbranched polysaccharide, e.g., a homo- or heteropolysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly (ethyleneglycol), such as methoxypoly(ethyleneglycol) or derivatives thereof.

Specific naturally-occurring polymers include lactose, amylose, dextran, glycogen and derivatives thereof.

In one embodiment the polymer is albumin or a fragment thereof, such as human serum albumin or a fragment thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in the average molecular weight range from 500 Da to 50,000 Da, for example from 5000 to 40,000 Da, such as from 20,000 to 40,000 Da. The polymer size may, in particular, be selected on the basis of the intended use of the product, for example, ability to localize to certain tissues, such as tumors, or extend circulating half-life (for review, see Chapman, 2002, Advanced Drug Delivery Reviews, 54:531-545). Thus, for example, where the product is intended to leave the circulation and penetrate tissue, for example for use in the treatment of a tumour, it may be advantageous to use a small molecular-weight polymer, for example, with a molecular weight of around 5000 Da. For applications where the product remains in the circulation, it may be advantageous to use a higher-molecular-weight polymer, for example, having a molecular weight ranging from 20,000 Da to 40,000 Da.

Suitable polymers include a polyalkylene polymer, such as a poly(ethyleneglycol) or, especially, a methoxypoly (ethyleneglycol) or a derivative thereof, and especially with a molecular weight in the range from about 15,000 Da to about 40,000 Da.

In one example antibodies for use in the present invention are attached to poly(ethyleneglycol) (PEG) moieties. In one particular example the antibody is an antibody fragment and the PEG molecules may be attached through any available amino acid side chain or terminal amino acid functional group located in the antibody fragment, for example, any free amino, imino, thiol, hydroxyl or carboxyl group. Such amino acids may occur naturally in the antibody fragment or may be engineered into the fragment using recombinant DNA methods (see, for example, U.S. Pat. No. 5,219,996; U.S. Pat. No. 5,667,425; WO98/25971; WO2008/038024). In one example the antibody molecule of the present invention is a modified Fab fragment wherein the modification is the addition to the C-terminal end of its heavy chain of one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment, appropriately activated effector molecules, for example, thiol-selective derivatives such as maleimides and cysteine derivatives, may be used. An activated polymer may be used as the starting material in the preparation of polymer-modified antibody fragments as described above. The activated polymer may be any polymer containing a thiol-reactive group, such as an α-halocarboxylic acid or ester, e.g., iodoacetamide, an imide, e.g., maleimide, a vinyl sulphone or a disulphide. Such starting materials may be obtained commercially (for example, from Nektar, formerly Shearwater Polymers, Inc., Huntsville, Ala., USA) or may be prepared from commercially available starting materials using conventional chemical procedures. Particular PEG molecules include 20K methoxy-PEG-amine (obtainable from Nektar, formerly Shearwater, Rapp Polymere, and SunBio) and M-PEG-SPA (obtainable from Nektar, formerly Shearwater).

In one embodiment, the antibody is a modified Fab fragment, Fab' fragment or diFab which is PEGylated, i.e., has PEG (poly(ethyleneglycol)) covalently attached thereto, e.g., according to the method disclosed in EP 0948544 or EP1090037 (see also "Poly(ethyleneglycol) Chemistry, Biotechnical and Biomedical Applications", 1992, J. Milton Harris (ed.), Plenum Press, New York; "Poly(ethyleneglycol) Chemistry and Biological Applications", 1997, J. Milton Harris and S. Zalipsky (eds.), American Chemical Society, Washington D.C.; "Bioconjugation Protein Coupling Techniques for the Biomedical Sciences", 1998, M. Aslam and A. Dent, Grove Publishers, New York; and Chapman, A. 2002, Advanced Drug Delivery Reviews, 54:531-545). In one example, PEG is attached to a cysteine in the hinge region. In one example, a PEG modified Fab fragment has a maleimide group covalently linked to a single thiol group in a modified hinge region. A lysine residue may be covalently linked to the maleimide group and a methoxypoly (ethyleneglycol) polymer having a molecular weight of approximately 20,000 Da may be attached to each of the amine groups on the lysine residue. The total molecular weight of the PEG attached to the Fab fragment may therefore be approximately 40,000 Da.

Particular PEG molecules include 2-[3-(N-maleimido) propionamido]ethyl amide of N,N'-bis(methoxypoly(ethylene glycol)) modified lysine (MW 20,000), also known as PEG2MAL40K (obtainable from Nektar, formerly Shearwater).

Alternative sources of PEG linkers include NOF, which supplies GL2-400MA3 (wherein m in the structure below is 5) and GL2-400MA (where m is 2) and n is approximately 450:

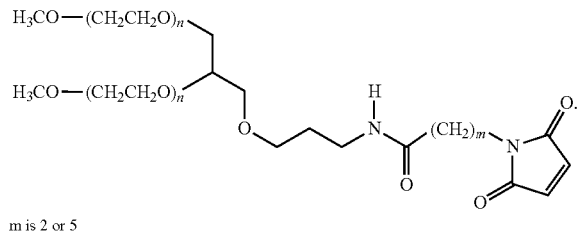

m is 2 or 5

That is to say, each PEG is about 20,000 Da.

Thus, in one embodiment, the PEG is 2,3-Bis(methylpolyoxyethylene-oxy)-1-{[3-(6-maleimido-1-oxohexyl) amino]propyloxy} hexane (the 2 arm branched PEG, —CH$_2$)$_3$NHCO(CH$_2$)$_5$-MAL, Mw 40,000 known as SUNBRIGHT GL2-400MA3.

Further alternative PEG effector molecules of the following type:

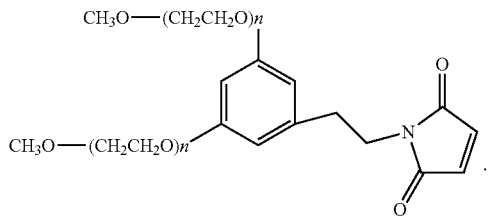

In one embodiment there is provided an antibody, such as a full-length antibody, which is PEGylated (for example, with a PEG described herein), attached through a cysteine amino acid residue at or about amino acid 226 in the chain, for example amino acid 226 of the heavy chain (by sequential numbering).

In one embodiment the present disclosure provides a Fab'PEG molecule comprising one or more PEG polymers, for example 1 or 2 polymers, such as a 40 kDa polymer or polymers.

Fab-PEG molecules according to the present disclosure may be particularly advantageous in that they have a half-life independent of the Fc fragment.

In one embodiment there is provided an scFv conjugated to a polymer, such as a PEG molecule, a starch molecule or an albumin molecule.

In one embodiment the antibody or fragment is conjugated to a starch molecule, for example to increase the half-life. Methods of conjugating start to a protein as described in U.S. Pat. No. 8,017,739, incorporated herein by reference.

A reporter molecule as employed herein is a molecule which is capable of being detected, for example, a fluorescent dye, radiolabel or other detectable entity.

The present invention also provides an isolated DNA sequence encoding the heavy and/or light chain(s) of an antibody molecule of the present invention. Suitably, the DNA sequence encodes the heavy or light chain of an antibody molecule of the present invention. The DNA sequence of the present invention may comprise synthetic DNA, for instance produced by chemical processing, cDNA, genomic DNA or any combination thereof.

DNA sequences which encode an antibody molecule of the present invention can be obtained by methods well-known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

Examples of suitable DNA sequences are provided in FIG. 1.

The present invention also relates to a cloning or expression vector comprising one or more DNA sequences of the present invention. Accordingly, provided is a cloning or expression vector comprising one or more DNA sequences encoding an antibody of the present invention. In one embodiment the vector comprises the sequences given in SEQ ID NO: 28 and/or SEQ ID NO: 20. Suitably, the cloning or expression vector comprises two DNA sequences encoding the light chain and the heavy chain of the antibody molecule of the present invention, preferably SEQ ID NO: 28 and SEQ ID NO: 20, respectively, and suitable signal sequences. In one example the vector comprises an intergenic sequence between the heavy and light chains (see WO03/048208).

General methods by which the vectors may be constructed, transfection methods and culture methods are well-known to those skilled in the art. In this respect, reference is made to "Current Protocols in Molecular Biology", 1999, F. M. Ausubel (ed.), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example E. coli, and other microbial systems may be used, or eukaryotic, for example mammalian, host cell expression systems may also be used. Suitable mammalian host cells include CHO, myeloma or hybridoma cells.

The present invention also provides a process for the production of an antibody molecule according to the present invention, comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The antibodies and fragments according to the present disclosure are expressed at good levels from host cells. Thus the properties of the antibodies and/or binding fragments are suitable for expression on a commercial scale.

Thus a process is provided for culturing a host cell and expressing an antibody or fragment thereof, isolating the latter and optionally purifying the same to provide an isolated antibody or fragment. In one embodiment the process further comprises the step of conjugating an effector molecule to the isolated antibody or fragment, for example conjugating to a PEG polymer in particular as described herein.

In one embodiment a process is provided for purifying an antibody (in particular an antibody or fragment according to the invention) comprising performing anion exchange chromatography in non-binding mode such that the impurities are retained on the column and the antibody is eluted.

In one embodiment the purification employs affinity capture on a CSF-1R column.

In one embodiment the purification employs Cibacron blue or similar for purification of albumin fusion or conjugate molecules.

Suitable ion exchange resins for use in the process include Q.FF resin (supplied by GE Healthcare). The step may, for example, be performed at a pH about 8.

The process may further comprise an initial capture step employing cation exchange chromatography, performed, for example, at a pH of about 4 to 5, such as 4.5. The cation exchange chromatography may, for example, employ a resin such as CAPTO S resin (high flow agarose with a dextran surface extender functionalized with sulfonate groups) or SP SEPHAROSE (agarose functionalized with sulfopropyl groups) FF (supplied by GE Healthcare). The antibody or fragment can then be eluted from the resin employing an ionic salt solution such as sodium chloride, for example at a concentration of 200 mM.

Thus the chromatography step or steps may include one or more washing steps, as appropriate.

The purification process may also comprise one or more filtration steps, such as a diafiltration step.

Thus in one embodiment there is provided a purified anti-CSF-1R antibody or fragment, for example a humanised antibody or fragment, in particular an antibody or fragment according to the invention, in substantially purified from, in particular free or substantially free of endotoxin and/or host cell protein or DNA.

Purified form as used supra is intended to refer to at least 90% purity, such as 91, 92, 93, 94, 95, 96, 97, 98, 99% w/w or more pure.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 µg per mg of antibody product or less, such as 100 µg per mg or less, in particular 20 µg per mg, as appropriate.

The present invention also provides an anti-CSF-1R antibody (or pharmaceutical compositions comprising same) according to the disclosure for use as a medicament.

The present invention also provides an anti-CSF-1R antibody (or pharmaceutical compositions comprising same) according to the disclosure, for the treatment of cancer.

The present invention also provides the use of an anti-CSF-1R antibody (or pharmaceutical composition comprising same) according to the disclosure in the manufacture of a medicament for the treatment or prophylaxis of cancer.

The present invention also provides a method for the treatment of a human subject suffering from or at risk of cancer, the method comprising administering to the subject an effective amount of an anti-CSF-1R antibody according to the disclosure.

The antibody according to the disclosure may be used to treat cancer that is selected from the group consisting of breast cancer, prostate cancer, bone cancer, myeloma, colorectal cancer, leukaemia, lymphoma, skin cancer such as melanoma, oesophageal cancer, gastric cancer, astrocytic cancer, endometrial cancer, cervical cancer, bladder cancer, renal cancer, lung cancer, liver cancer, thyroid cancer, head and neck cancer, pancreatic cancer and ovarian cancer.

In one embodiment the cancer is metastasised cancer from any of the above-listed original cancers, in particular bone cancer.

Surprisingly, we have been able to demonstrate that an anti-CSF-1R antibody that inhibits CSF-1R activity is active in the treatment of fibrotic disease. Specifically, we have been able to demonstrate that an anti-CSF-1R antibody is active in in vivo animal models of pulmonary fibrosis.

The present invention also provides an anti-CSF-1R antibody (or pharmaceutical compositions comprising same) according to the disclosure, for the treatment of fibrotic disease.

The present invention also provides the use of an anti-CSF-1R antibody (or pharmaceutical composition comprising same) according to the disclosure in the manufacture of a medicament for the treatment or prophylaxis of fibrotic disease.

The present invention also provides a method for the treatment of a human subject suffering from or at risk of fibrotic disease, the method comprising administering to the subject an effective amount of an anti-CSF-1R antibody according to the disclosure.

In the present application, the term "fibrotic disease" includes diseases that are characterised by an aberrant response to wound healing wherein excess fibrous connective tissue is formed in an organ or tissue. Illustrative fibrotic diseases include but are not limited to pulmonary fibrosis, such as idiopathic pulmonary fibrosis and cystic fibrosis, renal fibrosis, including tubular atrophy and interstitial fibrosis, liver fibrosis, liver cirrhosis, primary sclerosing cholangitis, primary biliary cirrhosis, endomyocardial fibrosis, mediastinal fibrosis, myelofibrosis, retroperitoneal fibrosis, progressive massive fibrosis, nephrogenic systemic fibrosis, Crohn's disease, keloid, myocardial infarction, scleroderma, systemic sclerosis and arthrofibrosis.

In one embodiment the antibodies or fragments according to the disclosure are employed in the treatment or prophylaxis of cancer or fibrotic disease.

The antibody according to the disclosure may be used in the treatment of inflammatory diseases, for example, inflammatory arthritis, atherosclerosis, multiple sclerosis, inflammatory bowel disease, Crohn's disease, ulcerative colitis, rheumatoid spondylitis, ankylosing spondylitis, arthritis, psoriatic arthritis, rheumatoid arthritis, osteoarthritis, eczema, contact dermatitis, psoriasis, toxic shock syndrome, sepsis, septic shock, endotoxic shock, asthma, chronic pulmonary inflammatory disease, silicosis, pulmonary sarcoidosis, osteoporosis, restenosis, cardiac and renal reperfusion injury, thrombosis, glomerulonephritis, diabetes, graft vs. host reaction, allograft rejection, multiple sclerosis, muscle degeneration, muscular dystrophy, Alzheimer's disease and stroke.

The antibodies and fragments according to the present disclosure may be employed in treatment or prophylaxis.

The antibody molecule of the present invention may also be used in diagnosis, for example in the in vivo diagnosis and imaging of disease states involving CSF-1R.

As the antibodies of the present invention are useful in the treatment and/or prophylaxis of a pathological condition, the present invention also provides a pharmaceutical or diagnostic composition comprising an antibody molecule of the present invention in combination with one or more of a pharmaceutically acceptable excipient, diluent or carrier. Accordingly, provided is the use of an antibody of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition, comprising adding and mixing the antibody molecule of the present invention together with one or more of a pharmaceutically acceptable excipient, diluent or carrier.

The antibody molecule may be the sole active ingredient in the pharmaceutical or diagnostic composition. Alternatively, the antibody may be administered in combination, e.g., simultaneously, sequentially or separately, with one or more other therapeutically active ingredients. According the antibody molecule in the pharmaceutical or diagnostic composition may be accompanied by other active ingredients, including other antibody ingredients, for example, the epidermal growth factor receptor family (EGFR, HER-2), vascular endothelial growth factor receptors (VEGFR), platelet-derived growth factor receptor (PDGFR) antibodies, or non-antibody ingredients such as imatinib, dasatinib, nioltinib, basutinib, gefitinib, erlotinib, temsirolimus, vandetanib, vemurafenib, crizotinib, vorinostat, romidepsin, bortezomib, sorafenib, sunitinib, pazopanib, regorafenib, cabozantinib, perfenidone, steroids or other drug molecules, in particular drug molecules whose half-life is independent of CSF-1R binding.

Active ingredient as employed herein refers to an ingredient with a pharmacological effect, such as a therapeutic effect, at a relevant dose.

The pharmaceutical compositions suitably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic, pharmacological or preventive effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician.

Generally, a therapeutically effective amount will be from 0.01 mg/kg to 500 mg/kg, for example 0.1 mg/kg to 200 mg/kg, such as 100 mg/kg.

Pharmaceutical compositions may be conveniently presented in unit dose forms containing a predetermined amount of an active agent of the invention per dose.

Therapeutic doses of the antibodies according the present disclosure show no apparent or limited toxicology effects in vivo.

Compositions may be administered individually to a patient or may be administered in combination (e.g., simultaneously, sequentially or separately) with other agents, drugs or hormones.

In one embodiment the antibodies or binding fragments according to the present disclosure are employed with one or more other cancer treatment options, such as chemotherapy, radiation therapy or surgery. If administered with a chemotherapeutic agent, the antibody can be administered before or after the chemotherapeutic agent or at the same time. Chemotherapy treatments that can be used in combination with the antigen-binding proteins that are provided include, but are not limited to, alkylating/DNA-damaging agents (e.g., carboplatin, cisplatin), antimetabolites (e.g., capecitabine, gemcitabine, 5-fluorouracil), and mitotic inhibitors (e.g., paclitaxel, vincristine).

The antibodies to be used to treat various inflammatory diseases can be used alone or combined with various other anti-inflammatory agents.

The antibodies to be used to treat various fibrotic diseases can be used alone or combined with various other anti-fibrotic agents. An examples of such an agent is perfenidone.

The dose at which the antibody molecule of the present invention is administered depends on the nature of the condition to be treated, the severity of the condition present and whether the antibody molecule is being used prophylactically or to treat an existing condition.

The frequency of dose will depend on the half-life of the antibody molecule and the duration of its effect. If the antibody molecule has a short half-life (e.g., 2 to 10 hours) it may be necessary to give one or more doses per day. Alternatively, if the antibody molecule has a long half-life (e.g., 2 to 15 days) and/or a long-lasting pharmacodynamic (PD) profile it may only be necessary to give a dose once per day, once per week or even once every 1 or 2 months.

Half-life as employed herein is intended to refer to the duration of the molecule in circulation, for example in serum/plasma.

Pharmacodynamics as employed herein refers to the profile and in particular the duration of the biological action of the molecule according the present disclosure.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example, mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH-buffering substances, may be present in such compositions.

Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g., by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably, in formulations according to the present disclosure, the pH of the final formulation is not similar to the value of the isoelectric point of the antibody or fragment; for example, if the pH of the formulation is 7, then a pI of from 8-9 or above may be appropriate. While not wishing to be bound by theory, it is thought that this may ultimately provide a final formulation with improved stability, for example, the antibody or fragment remains in solution.

In one example the pharmaceutical formulation at a pH in the range of 4.0 to 7.0 comprises: 1 to 200 mg/mL of an antibody according to the present disclosure, 1 to 100 mM of a buffer, 0.001 to 1% of a surfactant, and a) 10 to 500 mM of a stabiliser, b) 10 to 500 mM of a stabiliser and 5 to 500 mM of a tonicity agent, or c) 5 to 500 mM of a tonicity agent.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be on a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J., 1991).

In one embodiment the formulation is provided as a formulation for topical administration, including inhalation.

Suitable inhalable preparations include inhalable powders, metering aerosols containing propellant gases and inhalable solutions free from propellant gases. Inhalable powders according to the disclosure containing the active substance may consist solely of the above-mentioned active substances or of a mixture of the above-mentioned active substances with a physiologically acceptable excipient.

These inhalable powders may include monosaccharides (e.g., glucose or arabinose), disaccharides (e.g., lactose, saccharose, maltose), oligo- and polysaccharides (e.g., dextrans), polyalcohols (e.g., sorbitol, mannitol, xylitol), salts (e.g., sodium chloride, calcium carbonate) or mixtures of these with one another. Mono- or disaccharides are suitably used, the use of lactose or glucose, particularly but not exclusively in the form of their hydrates.

Particles for deposition in the lung require a particle size of less than 10 microns, such as 1-9 microns, for example from 0.1 to 5 µm, in particular from 1 to 5 µm. The particle size of the active ingredient (such as the antibody or fragment) is of primary importance.

The propellant gases which can be used to prepare the inhalable aerosols are known in the art. Suitable propellant gases are selected from among hydrocarbons, such as n-propane, n-butane or isobutane, and halohydrocarbons, such as chlorinated and/or fluorinated derivatives of methane, ethane, propane, butane, cyclopropane or cyclobutane. The above-mentioned propellant gases may be used on their own or in mixtures thereof.

Particularly suitable propellant gases are halogenated alkane derivatives selected from among TG 11, TG 12, TG 134a and TG227. Of the above-mentioned halogenated hydrocarbons, TG134a (1,1,1,2-tetrafluoroethane) and TG227 (1,1,1,2,3,3,3-heptafluoropropane) and mixtures thereof are particularly suitable.

The propellant-gas-containing inhalable aerosols may also contain other ingredients, such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively, topical administration to the lung may also be by administration of a liquid solution or suspension formulation, for example, employing a device such as a nebulizer, for example, a nebulizer connected to a compressor (e.g., the PARI LC Plus® jet nebulizer connected to a PARI MASTER® compressor manufactured by PARI Respiratory Equipment, Inc., Midlothian, Va.).

The antibody of the invention can be delivered dispersed in a solvent, e.g., in the form of a solution or a suspension. It can be suspended in an appropriate physiological solution, e.g., saline or another pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension can employ, for example, a lyophilised antibody.

The therapeutic suspensions or solution formulations can also contain one or more excipients. Excipients are well-known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacturing processes.

This may include production and sterilization by filtration of the buffered solvent/solution used for the formulation, aseptic suspension of the antibody in the sterile buffered solvent solution, and dispensing of the formulation into sterile receptacles by methods familiar to those of ordinary skill in the art.

Nebulizable formulations according to the present disclosure may be provided, for example, as single dose units (e.g., sealed plastic containers or vials) packed in foil envelopes. Each vial contains a unit dose in a volume, e.g., 2 mL, of solvent/solution buffer.

The antibodies disclosed herein may be suitable for delivery via nebulisation.

It is also envisaged that the antibody of the present invention may be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

In one embodiment the present disclosure comprises use of antibodies or fragments thereof as a reagent or diagnosis, for example conjugated to a reporter molecule. Thus there is provided an antibody or fragment according to the disclosure which is labelled. In one aspect there is provided a column comprising an antibody or fragment according to the disclosure.

Thus there is provided an anti-CSF-1R antibody or fragment for use as a reagent for such uses as:

1) Purification of CSF-1R protein (or a binding fragment thereof)—being conjugated to a matrix and used as an affinity column, or (as a modified form of anti-CSF-1R) as a precipitating agent (e.g., in a form modified with a domain recognised by another molecule, which may be modified), which is optionally precipitated by an anti-Fc reagent).

2) Detection and/or quantification of CSF-1R on cells or in cells, live or fixed (cells in vitro or in tissue or cell sections). Uses for this may include quantification of CSF-1R as a biomarker, to follow the effect of anti-CSF-1R treatment. For these purposes, the candidate might be used in a modified form (e.g., by addition of another moiety, or as a genetic fusion protein or chemical conjugate, such as addition of a reporter molecule, for example a fluorescent tag used for the purposes of detection).

3) Purification or sorting of CSF-1R-bearing cells labeled by binding to a candidate modified in the ways exemplified in (1) and (2).

Comprising in the context of the present specification is intended to mean including.

Where technically appropriate, embodiments of the invention may be combined.

Embodiments are described herein as comprising certain features/elements. The disclosure also extends to separate embodiments consisting of or consisting essentially of said features/elements.

Technical references such as patents and applications are incorporated herein by reference.

Any embodiments specifically and explicitly recited herein may form the basis of a disclaimer, either alone or in combination with one or more further embodiments.

The present invention is further described by way of illustration only in the following examples, which refer to the following Figures:

FIGS. 1A to 1F show certain amino acid and polynucleotide sequences.

FIGS. 2A and 2B show alignments of certain sequences.

FIG. 3 shows the sequence of human CSF-1R extracellular domain encoded by a polynucleotide employed to transfect cells and expressing the protein on the surface of the cell. These cells were then employed to immunize host animals.

FIG. 13 shows the effect on inhibition of CSF-1-mediated monocyte survival by humanised antibody 969.g5 compared to chimeric Ab969.g0.

Figure 18A:
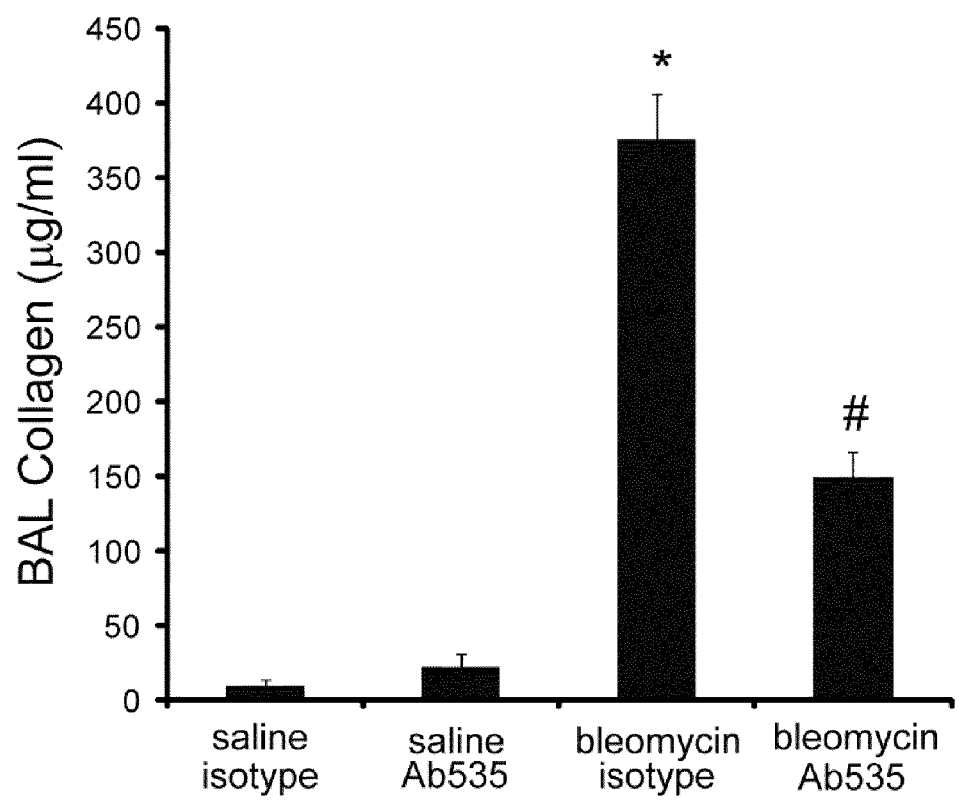
FIG. 18a shows the effect of treatment of bleomycin-induced lung fibrosis with Ab535 on BALF collagen concentration compared to an isotype control.
Figure 18B:
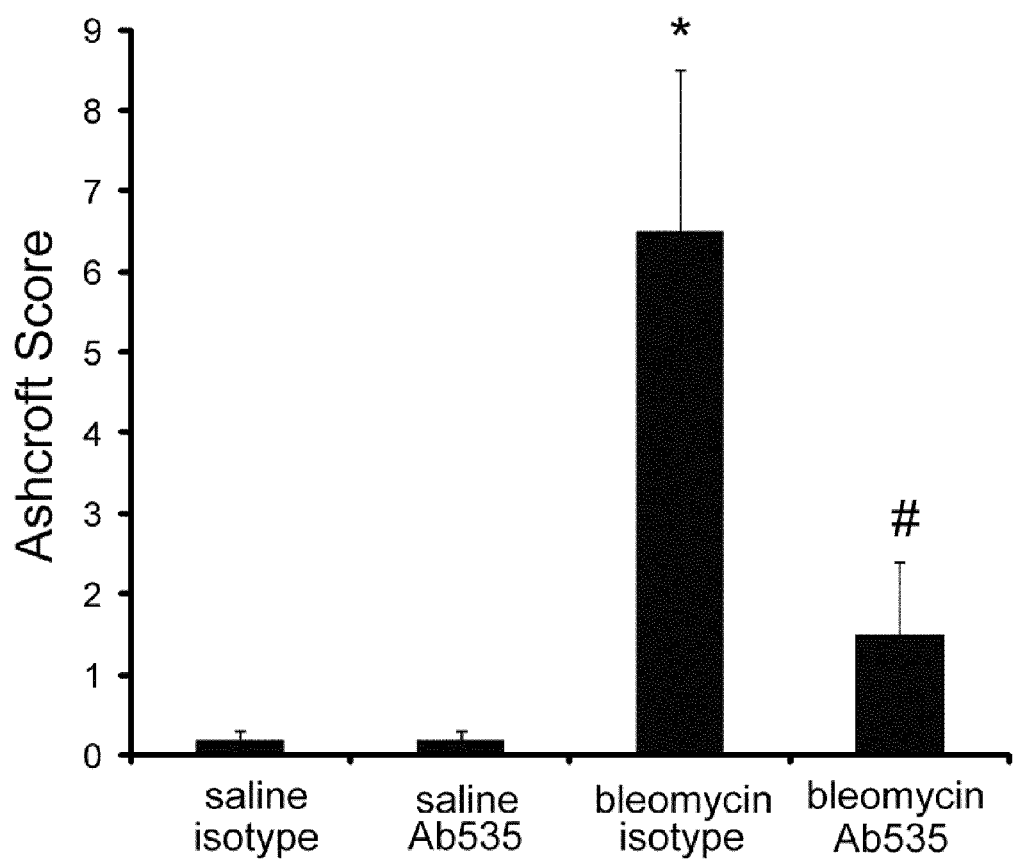
FIG. 18b shows the effect of treatment of bleomycin-induced lung fibrosis with Ab535 on the fibrotic pathology of lung samples measured by the Ashcroft score compared to an isotype control.
Figure 18C:
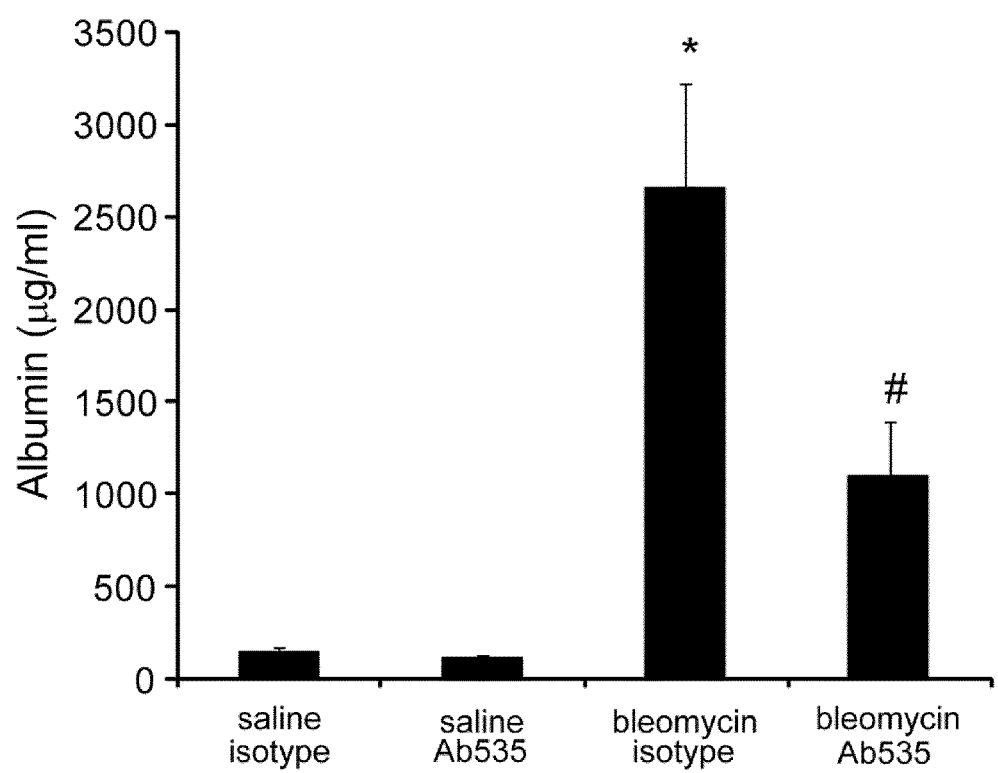
FIG. 18c shows the effect of treatment of bleomycin-induced lung fibrosis with Ab535 on the concentration of albumin in the serum compared to an isotype control.
Figure 18D:
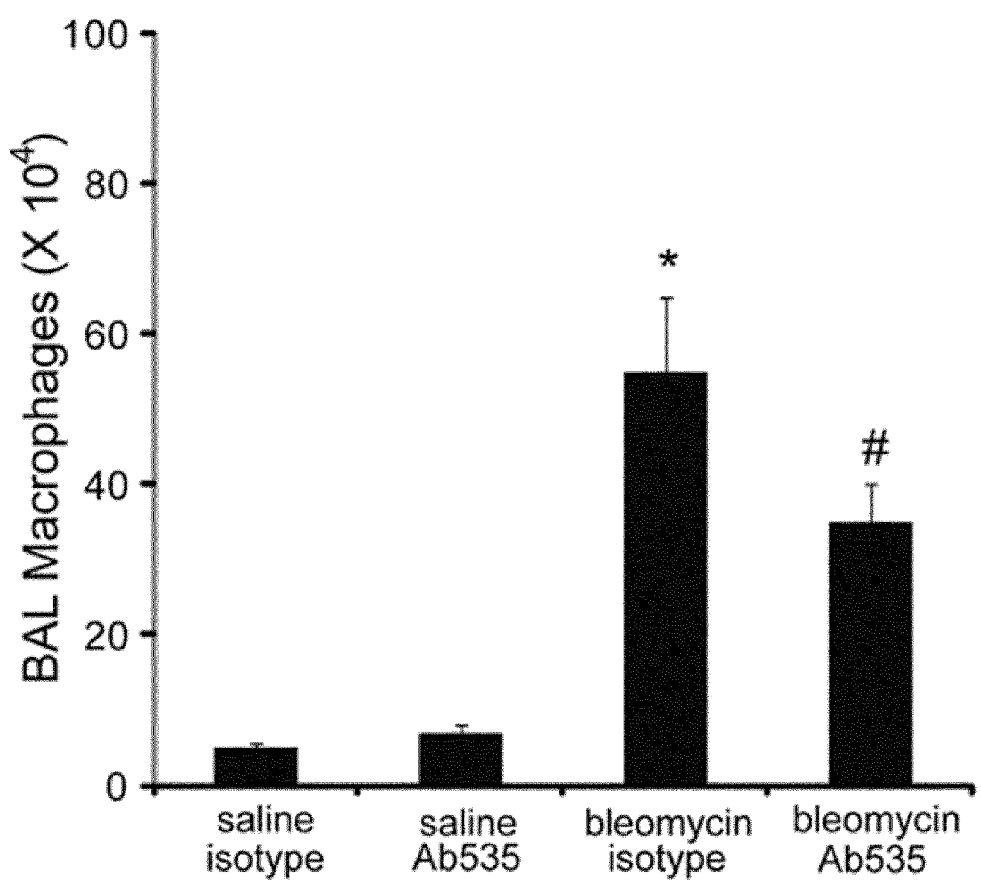

FIG. 18d shows the number of macrophages in the BAL fluid of mice from a bleomycin-induced lung fibrosis study and shows that treatment of bleomycin-induced lung fibrosis with Ab535 reduced the number of macrophages in BAL fluid compared to isotype control-treated animals. Data shown as means±SEM; * denotes significant difference from saline isotype; # denotes significant difference from bleomycin-treated mice dosed with isotype control antibody ($p \leq 0.05$).

Figure 19:
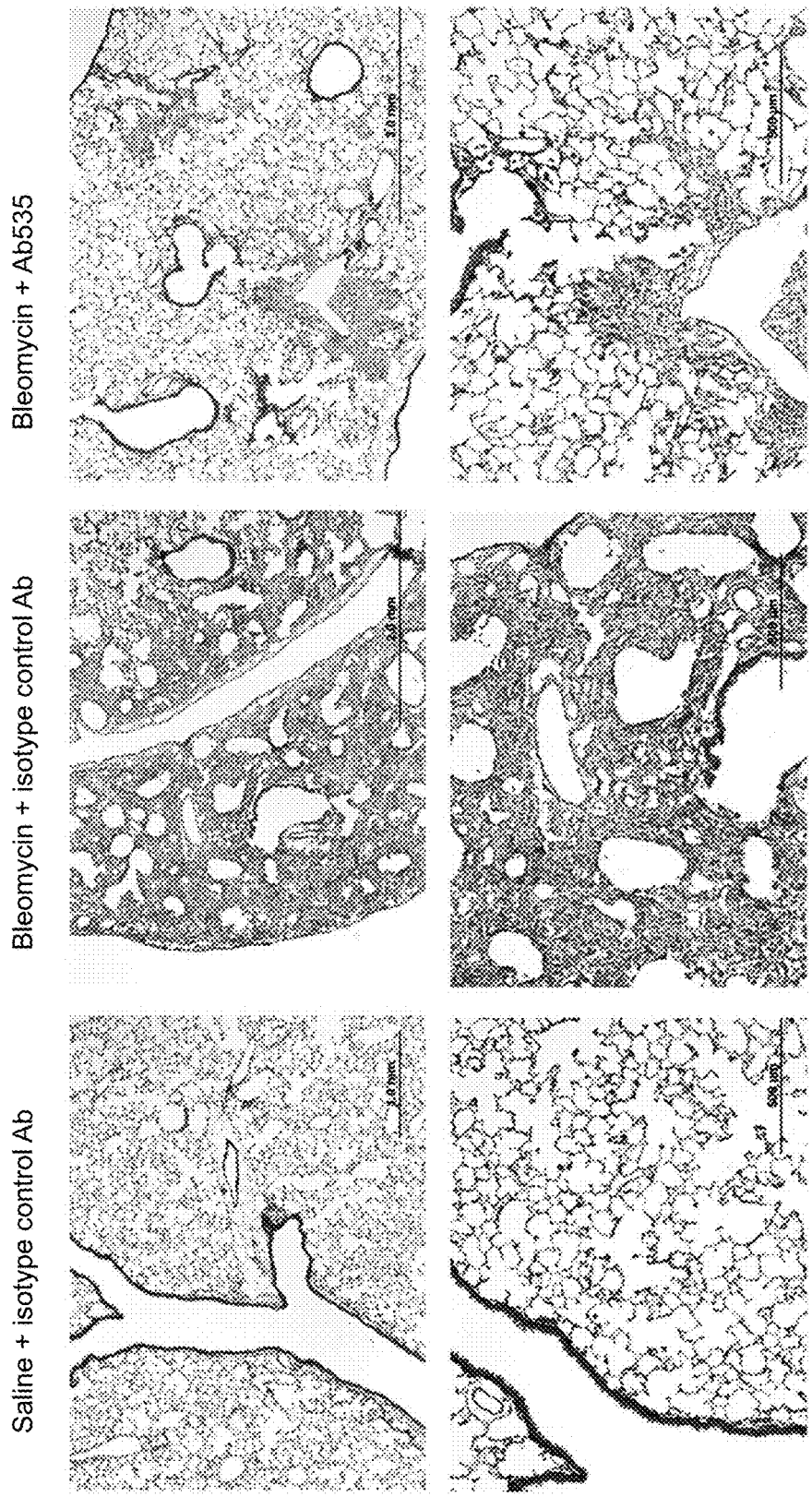

FIG. 19 shows representative images of the histopathological analysis of lungs from saline control, bleomycin plus isotype control and bleomycin plus Ab535-treated animals.

Figure 20A:
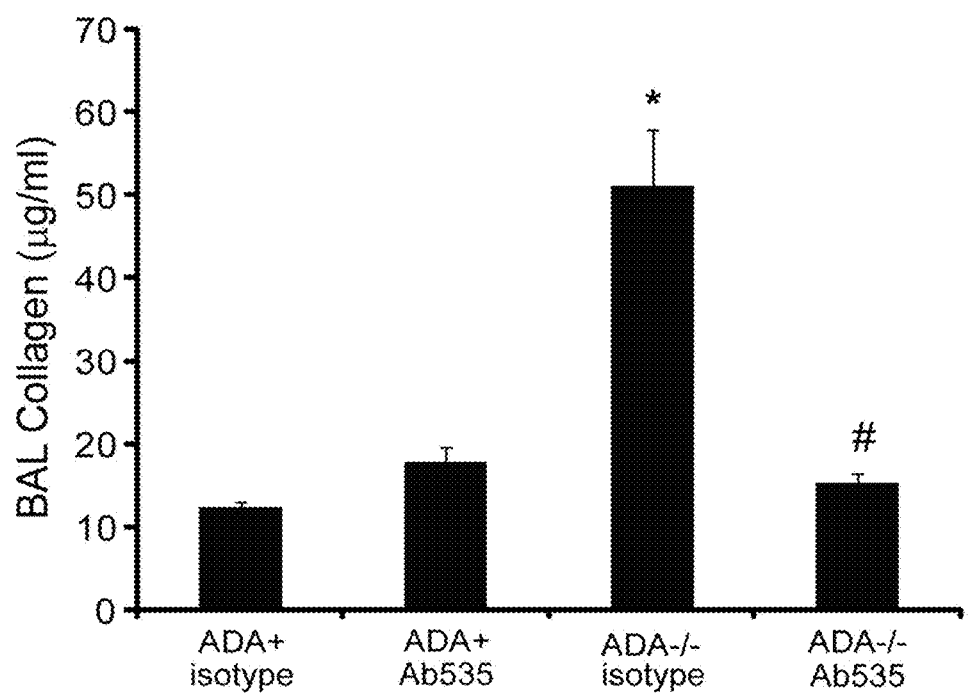

FIG. 20a shows the effect of treatment of ADA-deficient mice with induced lung fibrosis with Ab535 on BALF collagen concentration compared to treatment with the isotype control.

Figure 20B:
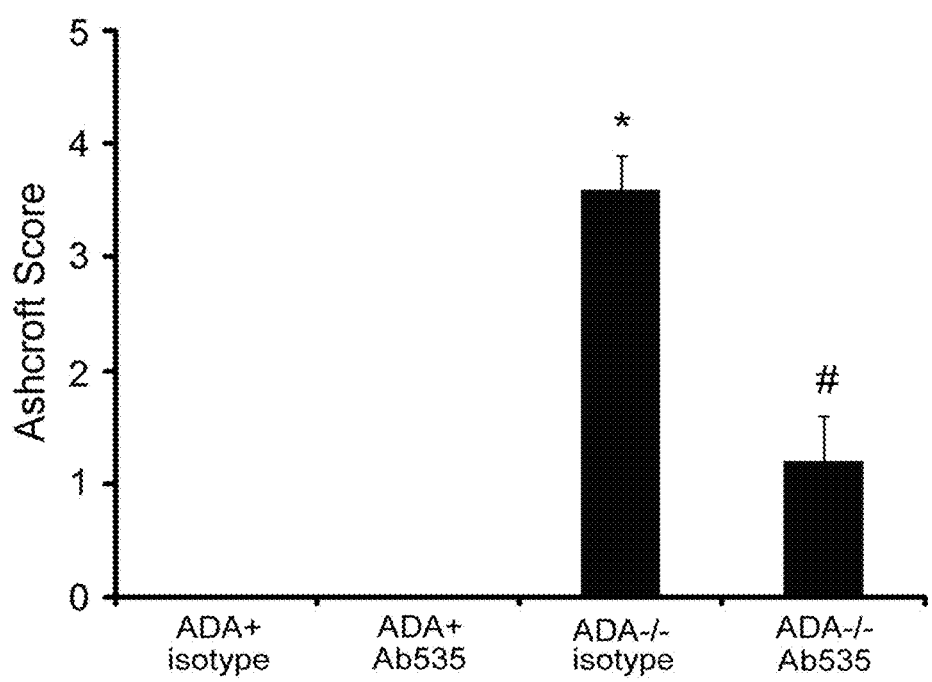

FIG. 20b shows the effect of treatment of ADA-deficient mice with induced lung fibrosis with Ab535 on the fibrotic pathology of lung samples measured by the Ashcroft score compared to treatment with the isotype control.

Figure 20C:
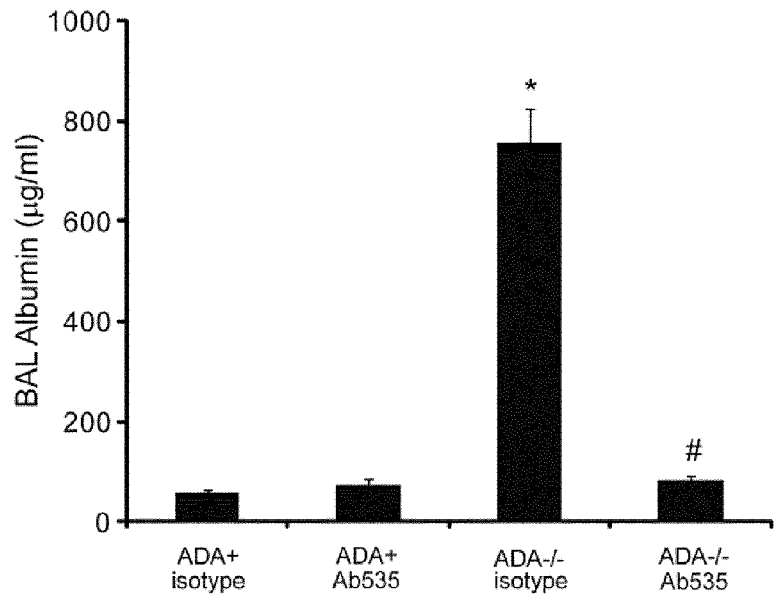

FIG. 20c shows the effect of treatment of ADA-deficient mice with induced lung fibrosis with Ab535 on the concentration of albumin in the serum compared to treatment with the isotype control.

Figure 20D:
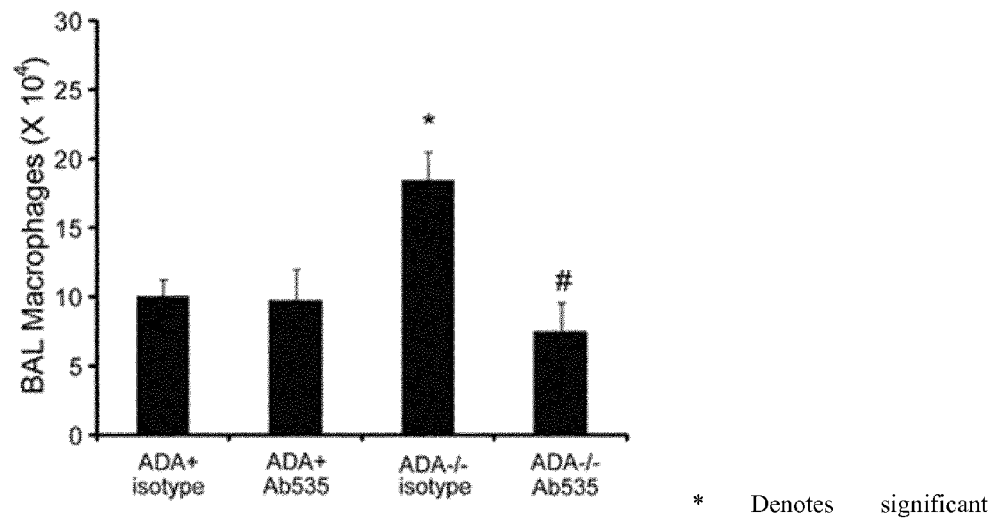

FIG. 20d shows the number of macrophages in the BAL fluid of mice from an ADA-deficient model of pulmonary fibrosis and shows that treatment of ADA-deficient mice with induced lung fibrosis with Ab535 reduced the number of macrophages in the BAL fluid.

Figure 21:
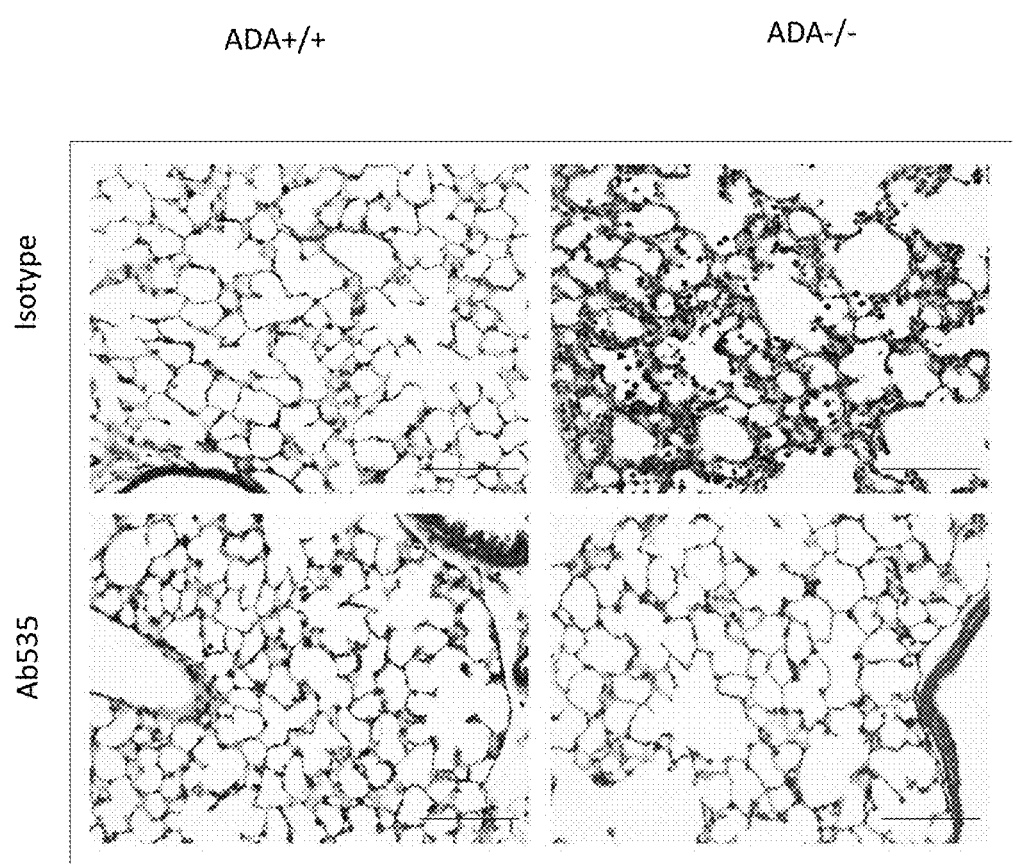

FIG. 21 shows representative images of the histopathological analysis of lungs from normal mice (ADA+) and ADA-deficient mice with induced lung fibrosis (ADA−) both treated with isotype control or Ab535.

EXAMPLES

Example 1—Generation of an Anti-CSF-1R Antibody

Immunisation

Female Sprague-Dawley rats were immunised with syngeneic RFL6 rat fibroblasts that had been transiently transfected with a vector expressing the human CSF-1R extracellular domain linked to a glycosylphosphatidyl-inositol (GPI) anchor. FIG. 3 shows SEQ ID NO: 39 which is the human CSF-1R extracellular domain sequence used in the immunisation of rats.

Rats received five subcutaneous immunisations at three-week intervals of $3-9 \times 10^6$ transfected cells per animal. Freund's Complete Adjuvant (50% in PBS) was injected at an adjacent site with the first cell immunisation. Two weeks post-final immunisation, peripheral blood mononuclear cells (PBMCs) and spleens were harvested.

Primary Screening of Antibody Supernatants

Antibody supernatants were initially screened for their ability to bind human CSF-1R expressed on transfected HEK293 cells by fluorescence microvolume assay technology (FMAT).

Approximately 1000 wells with anti-CSF-1R reactivity were identified in a primary FMAT screen of 600×96-well plates. In total, approximately $3 \times 10^8$ B cells (rat splenocytes) were screened for the production of CSF-1R binding antibodies by FMAT.

Secondary Screening of Antibody Supernatants

A medium-throughput assay was devised to identify FMAT-positive wells that contained neutralising anti-CSF-1R activity, i.e., antibodies that have the ability to prevent human CSF-1 binding to the human CSF-1R receptor. Antibody supernatants were incubated with CSF-1R-expressing THP-1 cells prior to incubation with human CSF-1. The level of CSF-1 binding to THP-1 cells was measured by flow cytometry using an anti-CSF-1 polyclonal antibody. Irrelevant antibody supernatants were used as negative controls.

The secondary screen was applied to supernatants from 779 antibody wells and 88 of these wells demonstrated detectable CSF-1 blocking activity.

Tertiary Screening of Antibody Supernatants

Antibody supernatants that had shown neutralising activity in the secondary screen were tested for their ability to prevent CSF-1-dependent survival of primary human monocytes. Monocytes were purified from human blood and $1 \times 10^4$ cells incubated with each antibody supernatant in the presence of 20 ng/ml human CSF-1. After 72 hours of incubation, the number of viable monocytes was measured by CellTiter-Glo assay.

The tertiary screen was applied to supernatants from 59 of the antibody wells identified in the secondary screen and 18 wells demonstrated an ability to reduce CSF-1-mediated monocyte survival.

Cloning of Antibody Variable Regions and Reanalysis of Blocking Activity

Variable region (V-region) cloning was attempted from the 18 antibody wells demonstrating CSF-1-neutralising activity. The heavy and light immunoglobulin V-regions were amplified by RT-PCR using primers specific to the rat antibody constant regions and a redundant primer set that anneals to sequences encoding rat immunoglobulin leader peptides. The V-region genes were recovered from 14 antibodies and cloned into heavy- and light-chain human IgG4 expression vectors.

Antibody vector pairs were transiently transfected into HEK293F cells and the conditioned medium tested for CSF-1 neutralising activity on THP-1 cells (as described above). Nine of the antibodies had the capacity to partially or fully inhibit CSF-1 binding compared to control conditioned medium.

Sequence Analysis of Nine Neutralising Anti-CSF-1R Antibodies

The nine neutralising antibodies were sequenced to assess sequence diversity. All nine antibodies were unique. These antibodies were cloned and expressed for further profiling studies.

Example 2—In Vitro Properties of Anti-Human CSF-1R Chimeric Ab969 and Anti-Murine CSF-1R Ab535 i) Expressing Chimeric Ab969

Variable regions of the nine neutralising antibodies identified in Example 1 were cloned into separate heavy- and light-chain expression vectors and were expressed as full-length human IgG4 antibodies.

The VH genes were cloned into vector pVhg4FL(V19H), which contains DNA encoding a natural leader sequence and the human gamma-4 heavy chain constant region with the hinge-stabilising mutation S241P. The VL genes (kappa) were cloned into vector pKH10.1(V4L), which contains DNA encoding a natural leader sequence and the human kappa chain constant region (Km3 allotype).

Antibodies were expressed by transient co-transfection of matching heavy- and light-chain vector pairs into CHO-K1 cells. Purification of the antibodies into PBS, pH 7.4 was performed so that the level of aggregate in the final preparation was less than 1%.

The panel of nine antibodies included an antibody designated antibody 969. The chimeric antibody comprising the rat variable regions and the human gamma-4 heavy chain constant region and human kappa chain constant region is referred to as antibody 969 or antibody 969cHcL or antibody 969.g0 in the following examples.

ii) Ligand-Blocking Assay

The capacity of each of the nine antibodies to inhibit CSF-1 binding to THP-1 cells was assessed by flow cytometry. THP-1 cells were incubated with each antibody at 0.5, 0.125, 0.031, 0.0078 and 0.00195 µg/ml for 30 minutes. An irrelevant IgG4 antibody served as an isotype control. After washing, cells were incubated with 0.5 µg/ml human CSF-1 for 30 minutes. After further washing, bound CSF-1 was detected by sequential incubation with biotinylated anti-CSF-1 antibody and Alexa488-conjugated streptavidin. Receptor-bound ligand was measured by flow cytometry and median fluorescence intensity (MFI) plotted.

Figure 4:
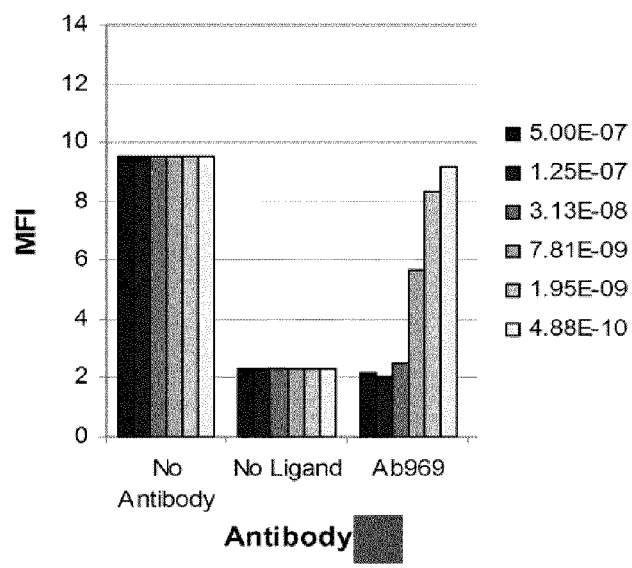
FIG. 4 shows the inhibition of CSF-1 binding to THP-1 cells by antibody Ab969.

This assay identified four antibodies, including Ab969, that were superior to the remaining antibodies tested, demonstrating complete inhibition of CSF-1 binding at a concentration of 31.3 ng/ml. The results for Ab969 are shown in FIG. 4.

iii) Inhibition of CSF-1- and IL-34-Mediated Monocyte Survival

Anti-Human CSF-1R

The purified anti-human CSF-1R antibodies were tested for their capacity to inhibit the CSF-1- and IL-34-driven survival and proliferation of primary human monocytes. In each assay, the mitogen (CSF-1 or IL-34) was used at a concentration that gave maximal stimulation of the monocytes.

Figure 5A:
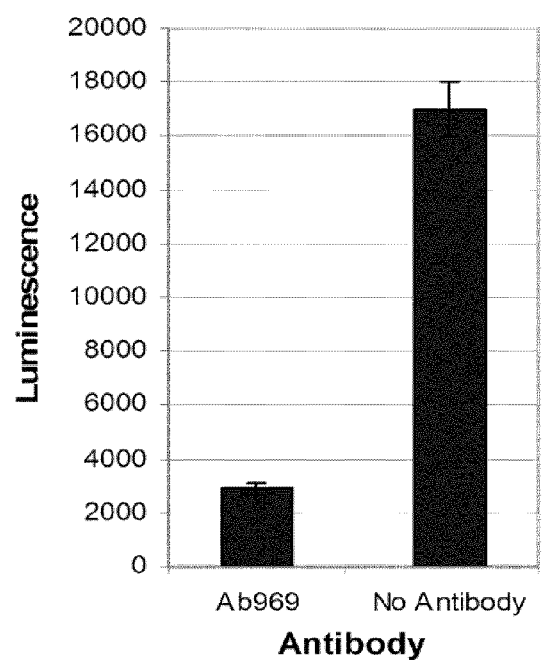
FIG. 5a shows the inhibition of CSF-1-driven survival and proliferation by primary human monocytes by antibody Ab969.

Human PBMCs were prepared from fresh human whole blood on a Ficoll gradient and monocytes were purified by negative selection. Monocytes were incubated with 0.25 µg/ml antibody and 20 ng/ml CSF-1 for 72 hours and the relative number of viable cells determined using CellTiter-Glo analysis. The luminescence readout correlates with the number of viable cells. Results shown in FIG. 5a.

Figure 5B:
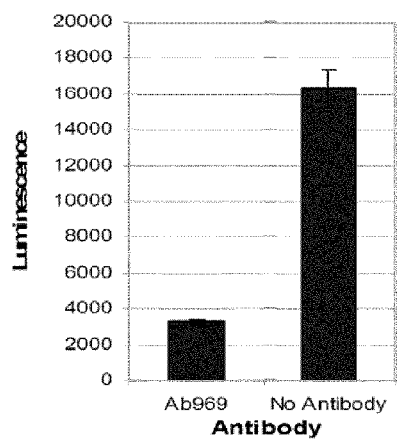
FIG. 5b shows the inhibition of IL-34-driven survival and proliferation by primary human monocytes by antibody Ab969.

Human PBMCs were prepared from fresh human whole blood on a Ficoll gradient and monocytes were purified by negative selection. Monocytes were incubated with 0.25 µg/ml antibody and 20 ng/ml IL-34 for 72 hours and the relative number of viable cells determined using CellTiter-Glo analysis. The luminescence readout correlates with the number of viable cells. Results shown in FIG. 5b.

Four of the antibodies, including Ab969, demonstrated superior inhibition of monocyte survival compared to the remaining antibodies for both CSF-1 (FIG. 5a) and IL-34 (FIG. 5b) stimulation, in line with their ligand-blocking activities.

Anti-Mouse CSF-1R

Figure 6:
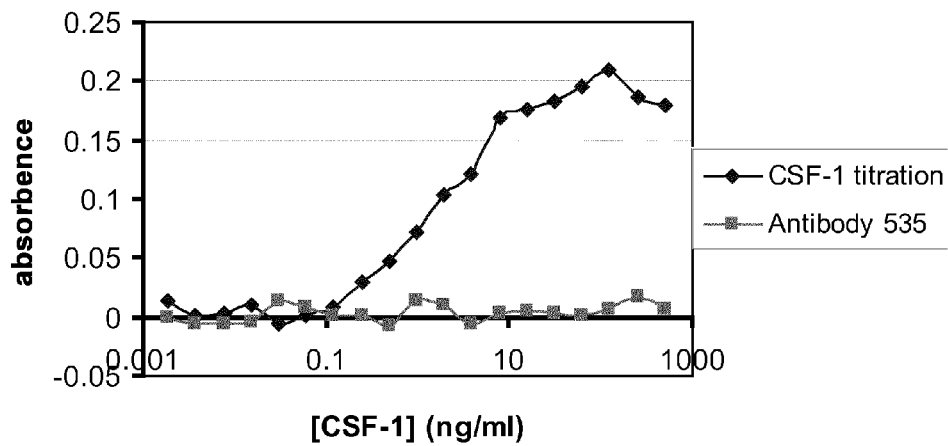
FIG. 6 shows the inhibition of CSF-1-driven survival and proliferation by primary murine monocytes by antibody Ab535.

Primary murine CD11b$^+$ monocytes were purified from mouse spleens. The monocytes were then incubated with a titration of murine CSF-1 (mCSF-1) for 24 hours. The release of MCP-1 into the cell medium was measured by ELISA and a dose-dependent release of MCP-1 by mCSF-1 demonstrated. In a separate arm of the study, 10 µg/ml anti-murine CSF-1R Ab535 was added along with the mCSF-1 titration. The release of MCP-1 was completely inhibited by Ab535 at all concentrations of CSF-1 tested (FIG. 6).

The MCP-1 release assay was performed using primary murine monocytes with a constant CSF-1 concentration of 100 ng/ml and a titration of Ab535. A dose-dependent inhibition of MCP-1 release was demonstrated and an $IC_{50}$ calculated. The mean $IC_{50}$ of Ab535 from two independent experiments was determined to be 8.08 ng/ml.

Conclusion: Treatment of murine monocytes with CSF-1 caused a dose-dependent release of MCP-1, which was completely inhibited by treatment with 10 µg/ml Ab535. Ab535 inhibits CSF-1-driven MCP-1 release from murine monocytes in a dose-dependent manner, with a mean $IC_{50}$ of 8.08 ng/ml (n=2). This $IC_{50}$ value is similar to that exhibited by the anti-human-CSF-1R antibodies.

iv) Affinity

Antibodies were tested for their ability to bind CSF-1R in a BIAcore assay by measurement of binding kinetics to a purified recombinant CSF-1R/Fc fusion protein.

The assay format was capture of the anti-CSF-1R antibodies by immobilised anti-human IgG,F(ab')$_2$, then a titration of hCSF-1R/Fc over the captured surface. BIA (Biomolecular Interaction Analysis) was performed using a BIAcore 3000 (GE Healthcare Bio-Sciences AB). All experiments were performed at 25° C. An AffiniPure F(ab')$_2$ fragment goat anti-human IgG, F(ab')$_2$ fragment specific (Jackson ImmunoResearch), was immobilised on a CM5 Sensor Chip (GE Healthcare Bio-Sciences AB) via amine coupling chemistry to a level of 5000 response units (RU). HBS-EP buffer (10 mM HEPES, pH 7.4, 0.15M NaCl, 3 mM EDTA, 0.005% Surfactant P20, GE Healthcare Bio-Sciences AB) was used as the running buffer with a flow rate of 10 µl/min. An injection of an anti-CSF-1R antibody was performed to give a capture level of approximately 100 RU on the immobilised anti-human IgG,F(ab)$_2$.

Recombinant human CSF-1R/Fc (R&D Systems) was passed over the captured anti-CSF-1R antibody at 5 nM at a flow rate of 30 ul/min for 5 min, then the flow rate was increased to 100 ul/min for 30 min for the dissociation phase. The injection at 5 nM was performed twice along with a corresponding buffer control. These sensorgrams were used to generate the dissociation rate. Recombinant human CSF-1R/Fc was titrated over the captured anti-CSF-1R antibody from 2.5 nM at a flow rate of 30 ul/min for 5 min followed by a 10 min dissociation phase. These sensorgrams were used to generate the association rate. The surface was regenerated at a flow rate of 10 ul/min by a 10 ul injection of 40 mM HCl followed by a 5 ul injection of 10 mM NaOH. Double referenced background subtracted binding curves were analysed using the BIAevaluation software (version 4.1) following standard procedures. Kinetic parameters were determined from the fitting algorithm.

Three of the four tested antibodies exhibited affinities ($K_D$) of less than 10 pM. This compares favourably with the anti-murine-CSF-1R parallel reagent, Ab535. The results for Ab969 and Ab553 are shown in Table 1.

TABLE 1

| Antibody | On-rate $K_a$ (M$^{-1}$s$^{-1}$) | Off-rate $K_d$ (s$^{-1}$) | Affinity $K_D$ (M) | Affinity $K_D$ (pM) |
|---|---|---|---|---|
| Ab969 | 2.58 × 10$^6$ | 2.49 × 10$^{-5}$ | 9.65 × 10$^{-12}$ | 9.6 |
| Ab535 | 2.24 × 10$^6$ | 1.06 × 10$^{-5}$ | 4.73 × 10$^{-12}$ | 4.7 |

The affinity of the antibodies was also measured by a cell-based assay using THP-1 cells. The antibodies were directly labelled with Alexa-488 fluorescent dye and affinity measured by quantitative flow cytometry. An additional BIAcore analysis confirmed that fluorescent conjugation of the antibodies did not alter the affinity toward recombinant CSF-1R protein. The results are shown in Table 2.

The absolute affinity values derived by the two methodologies are different, and this difference is usually observed when the two systems are compared. However, the cell-based method demonstrated that the antibodies bind CSF-1R with high affinity.

TABLE 2

| Antibody | Cell-based affinity $K_D \pm$ S.D. (nM) | BIAcore affinity $K_D$ (pM) |
|---|---|---|
| Ab969 | 2.20 ± 0.19 | 4.80 | v) Inhibition of CSF-1 Binding ($IC_{50}$)

Four antibodies were analysed by measuring their relative potency at inhibiting CSF-1 binding to THP-1 cells. All four antibodies exhibited potent inhibition of CSF-1 binding with $IC_{50}$ values of less than 5 ng/ml (~30 pM) in this assay format.

TABLE 3

| Antibody | Mean $IC_{50}$ ± S.D. (ng/ml) |
|---|---|
| Ab969 | 2.89 ± 1.22 | vi) Antibody Cross Reactivity

Four antibodies were tested for cross-reactivity with rhesus monkey, cynomolgus monkey and canine full-length CSF-1R. All four antibodies bound rhesus and cynomolgus CSF-1R in addition to human CSF-1R, demonstrating clear binding significantly above the level of the isotype control.

TABLE 4

| Antibody | Cross-reactivity | | |
|---|---|---|---|
| | Cynomolgus | Rhesus | Canine |
| Ab969 | Yes | Yes | No | vii) CSF-1R Internalization
Ab969

Figure 7:
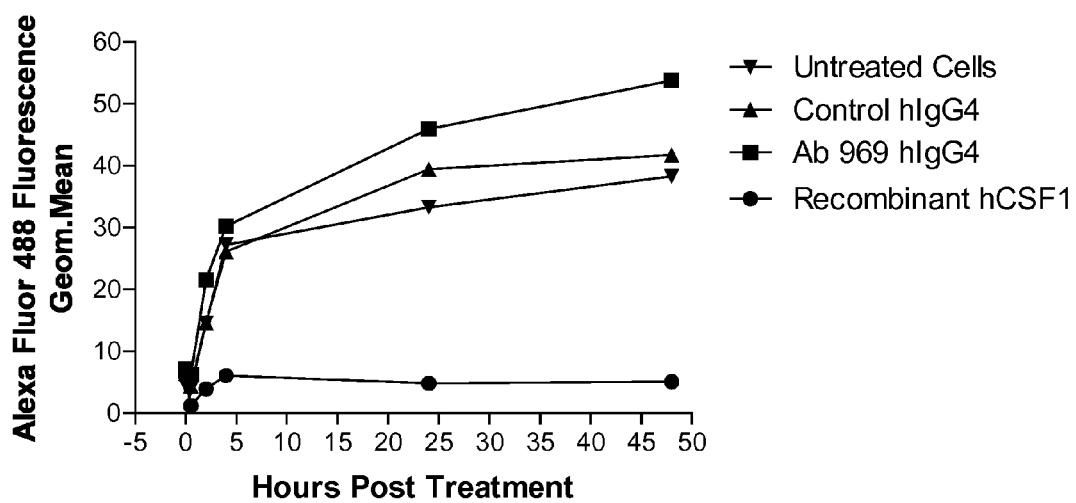
FIG. 7 shows the levels of cell-surface CSF-1R on THP-1 cells incubated with Ab969, human CSF-1 and an isotype control.
Figure 8:
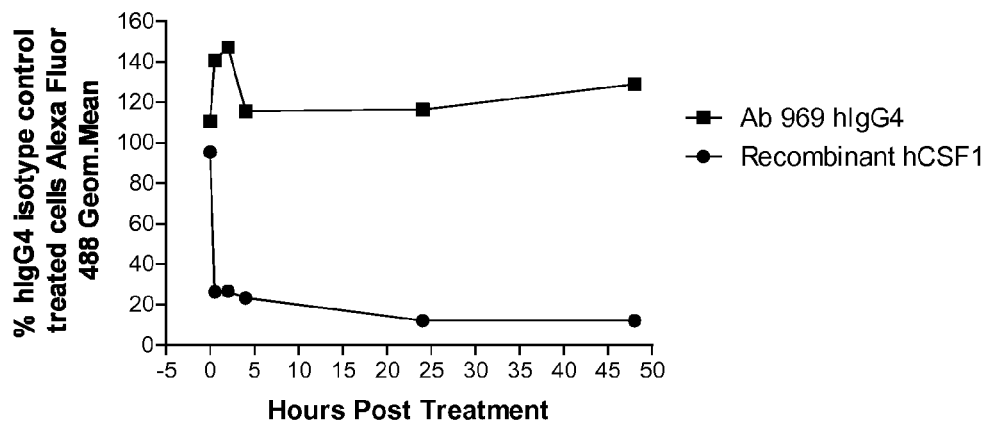
FIG. 8 shows the relative level of cell-surface CSF-1R on THP-1 cells treated with Ab969 compared to an isotype control.

THP-1 cells were incubated with Ab969 for 0, 0.5, 2, 4, 24 and 48 hours. Cells were also treated with human CSF-1 and an isotype control that served as positive and negative controls, respectively. At each timepoint, the level of cell-surface CSF-1R was measured by flow cytometry (FIG. 7). The relative level of cell-surface CSF-1R on cells treated with Ab969 compared to the isotype control was calculated and is shown in FIG. 8.

Treatment of THP-1 cells with recombinant CSF-1 caused a rapid and sustained decrease in the level of cell-surface CSF-1R; the natural ligand binds to its cognate receptor and drives internalisation of the ligand-receptor complex.

THP-1 cells treated with Ab969 exhibited higher levels of cell-surface CSF-1R expression compared to the untreated and isotype control-treated THP-1 cells throughout the whole 48-hour time course. This data strongly suggests that treatment of THP-1 cells with Ab969 does not cause internalisation of cell-surface expressed hCSF-1R up to 48 hours post-treatment.

As the time course progressed there was a notable increase in cell-surface expressed CSF-1R on the untreated and treated THP-1 cells, with the exception of cells treated with CSF-1. This might be due to expression changes during the period of cell growth over the 48-hour time period of the experiment and could potentially be a stress response.

In order to provide further evidence that Ab969 does not potentiate receptor internalisation, and also preclude the possibility that the THP-1 cell line is not physiologically relevant, primary human monocytes were also used in an internalisation assay. The data from this assay also demonstrated that Ab969 does not cause rapid internalisation of cell-surface CSF-1R on healthy primary human monocytes.
Ab535

The mouse leukaemic monocyte/macrophage cell line RAW264.7 expresses high levels of murine CSF-1R (mCSF-1R) and represents a suitable cell-based system for testing whether the anti-murine CSF-1R antibody Ab535 can elicit receptor internalisation.

Figure 9:
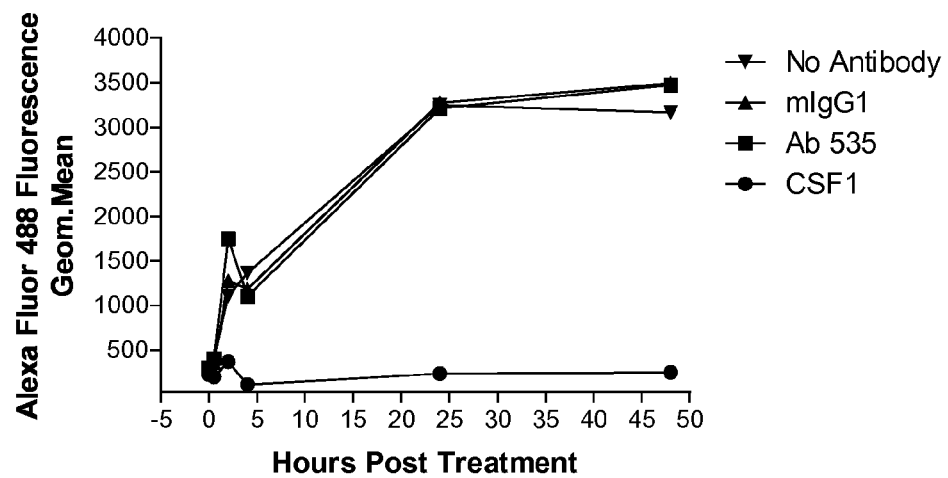
FIG. 9 shows the levels of cell-surface CSF-1R on RAW264.7 cells incubated with Ab 535, CSF-1 and an isotype control.
Figure 10:
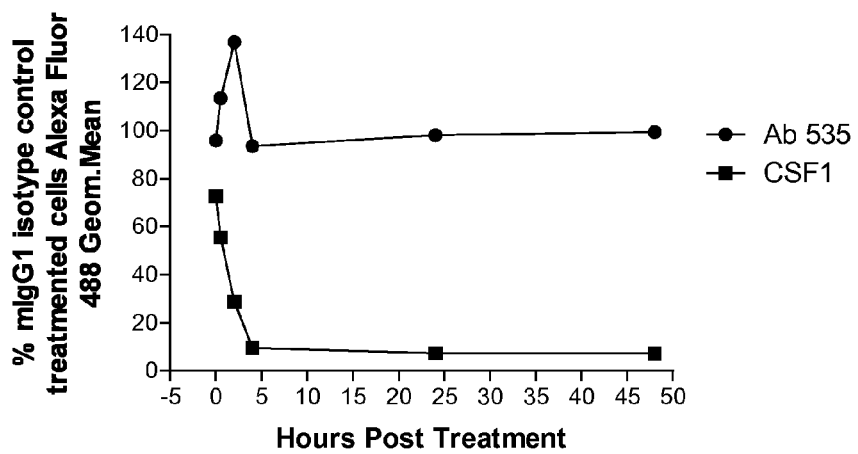
FIG. 10 shows the relative level of cell-surface CSF-1R on RAW264.7 cells treated with Ab535 compared to an isotype control.

RAW264.7 cells were incubated with Ab535 for 0, 0.5, 2, 4, 24 and 48 hours. Cells were also treated with human CSF-1 and an isotype control that served as a positive and negative control, respectively. At each timepoint, the level of cell-surface CSF-1R was measured by flow cytometry (FIG. 9). The relative level of cell-surface CSF-1R compared to the isotype control was calculated and is shown in FIG. 10.

The data show that treatment of THP-1 cells with recombinant CSF-1 caused a rapid and sustained decrease in the level of cell-surface CSF-1R.

A clear reduction of cell-surface mCSF-1R levels was observed on RAW264.7 cells treated with human CSF-1 for 2 hours relative to the untreated and isotype control-treated cells. This reduction is maintained throughout the 48 hour study. This demonstrates that human CSF-1 elicits internalisation of mCSF-1R and validates the experimental system for monitoring receptor internalisation.

RAW264.7 cells treated with Ab535 exhibit similar levels of cell-surface mCSF-1R compared to untreated and isotype control-treated cells throughout the whole 48-hour time course. As antibody-mediated receptor internalisation would be expected to occur within this timeframe, this data strongly suggests that Ab535 does not trigger mCSF-1R internalisation.

In order to provide further evidence that Ab535 does not potentiate receptor internalisation, primary murine $CD11b^+$ monocytes-macrophages were used in an internalisation assay. These results also demonstrated that treatment of mouse monocyte-macrophages with Ab535 does not cause internalisation of cell-surface expressed mCSF-1R up to 24 hours post-treatment.

viii) CSF 1-R Activation

CSF-1 binds to CSF-1R, causing the formation of receptor dimers, which triggers rapid receptor phosphorylation by bringing the kinase domains together in close proximity. This subsequently leads to receptor internalisation and the activation of several well-characterised signal transduction pathways, including the Ras-MAPK pathway. It is possible that an anti-CSF-1R antibody could elicit receptor clustering and trigger a downstream signalling cascade. This may be an undesired property for an antibody that should inhibit receptor signalling, so receptor agonism by Ab969 was tested using two independent in vitro assay formats.

In the first assay format, antibodies were incubated with cells transfected with human full-length CSF-1R and phosphorylation of the receptor and downstream signal transduction molecules monitored by Western blotting.

The THP-1 cell line represented a starting point for monitoring the activation status of CSF-1R. However, the expression level of CSF-1R in this cell line is relatively low, making it difficult to perform biochemical analysis. Therefore, an experimental system was devised so that the level of CSF-1R phosphorylation could be robustly detected. Phosphorylation of CSF-1R can be detected at two tyrosine residues, Y723 and Y809. In addition, phosphorylation of p44/42 MAPK (Erk1/2) at T202 and Y204 was measured as an independent readout of CSF-1R activity. Stimulation with CSF-1 was included as a positive control in all experiments.

HEK293F cells were transfected with a plasmid vector expressing full-length CSF-1R. After 24 hours of incubation in serum-free conditions, cells were stimulated with a 100 µg/ml to 0.001 µg/ml titration of Ab969.g0 for 5 minutes. Cells were also treated with 500 ng/ml recombinant CSF-1 to provide a positive control. Untreated cells were included as a negative control. Protein lysates from treated and untreated cells were separated by SDS-polyacrylamide electrophoresis and blotted onto nitrocellulose. Western immunoblotting was performed using antibodies to phospho-Y723 CSF-1R (Cell Signaling Technology, #3151), phospho-Y809 (Cell Signaling Technology, #3154), total CSF-1R (Cell Signaling Technology, #3152) and phospho-ERK1/2 (p44/42 MAPK) (Cell Signaling Technology, #5301).

Figure 11:
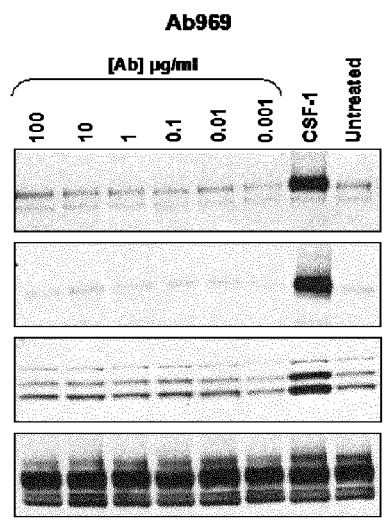
FIG. 11 shows the level of CSF-1R phosphorylation on HEK293F cells transfected with CSF-R upon stimulation with CSF-1 or treatment with Ab969.

Unstimulated CSF-1R-transfected HEK293F cells exhibited a low basal level of CSF-1R phosphorylation. Stimulation of cells with CSF-1 resulted in a level of CSF-1R phosphorylation at residues Y723 and Y809 readily observed by Western blotting analysis (FIG. 11). There was also clear stimulation of ERK1/2 phosphorylation upon CSF-1 treatment. Treatment of the transfected HEK293F cells with antibody Ab969.g0 did not stimulate phosphorylation of CSF-1R or potentiate ERK1/2 activation.

In a second assay, antibody Ab969 (monomeric and cross-linked) was incubated with primary human monocytes and MCP-1 secretion used as a marker of CSF-1R activation. CSF-1 treatment of human monocytes causes them to release monocyte chemoattractant protein-1 (MCP-1). If anti-CSF-1R antibodies have an ability to activate the CSF-1R receptor on monocytes, a release of MCP-1 would be expected to occur.

The biochemical assays described previously used only monomeric anti-CSF-1R antibody. However, it is possible that a cross-linked IgG1 would have an enhanced capacity to bring CSF-1R molecules into close proximity and trigger tyrosine phosphorylation and downstream signalling. To assess this, the MCP-1 assay was also performed using Ab969.g0 that had been cross-linked with an anti-human-Fc antibody.

Human monocytes were prepared from human whole blood as follows: 60-100 ml human whole blood was collected in BD Vacutainer 10 ml Lithium Heparin 171 IU Tubes. Blood was split into 3-4 Leucosep Ficoll tubes (Greiner Bio-One) and topped up with PBS. Tubes were centrifuged at 1000 g, 20° C. for 10 minutes with no brake, and the PBMC layer was collected. Cells were pelleted, and monocytes were then isolated using positive selection human CD14 beads (Miltenyi Biotec, 130-050-201) according to the manufacturer's protocol. Antibody Ab969.g0 was cross-linked by adding goat anti-human IgG Fc antibody (R&D Systems, G-102-C) at a ratio of 2:1 Ab969.g0:Fc. Monocytes were seeded at 20,000 cells per well in media in the presence of a dose titration of antibody Ab969.g0 or cross-linked Ab969.g0 (half-log dilution series comprising 16 concentrations, maximum 10 µg/ml). Control wells contained no antibody, in the presence and absence of 100 ng/ml CSF-1, and in the presence and absence of anti-human-Fc antibody (at the same concentration as present in the top concentration of antibody Ab969.g0 (5 µg/ml)). Cells were incubated for 24 hours, plates were spun to pellet cells, and supernatant was collected. Secreted MCP-1 was measured by MSD (K151AYB-2) according to the manufacturer's protocol.

Figure 12:
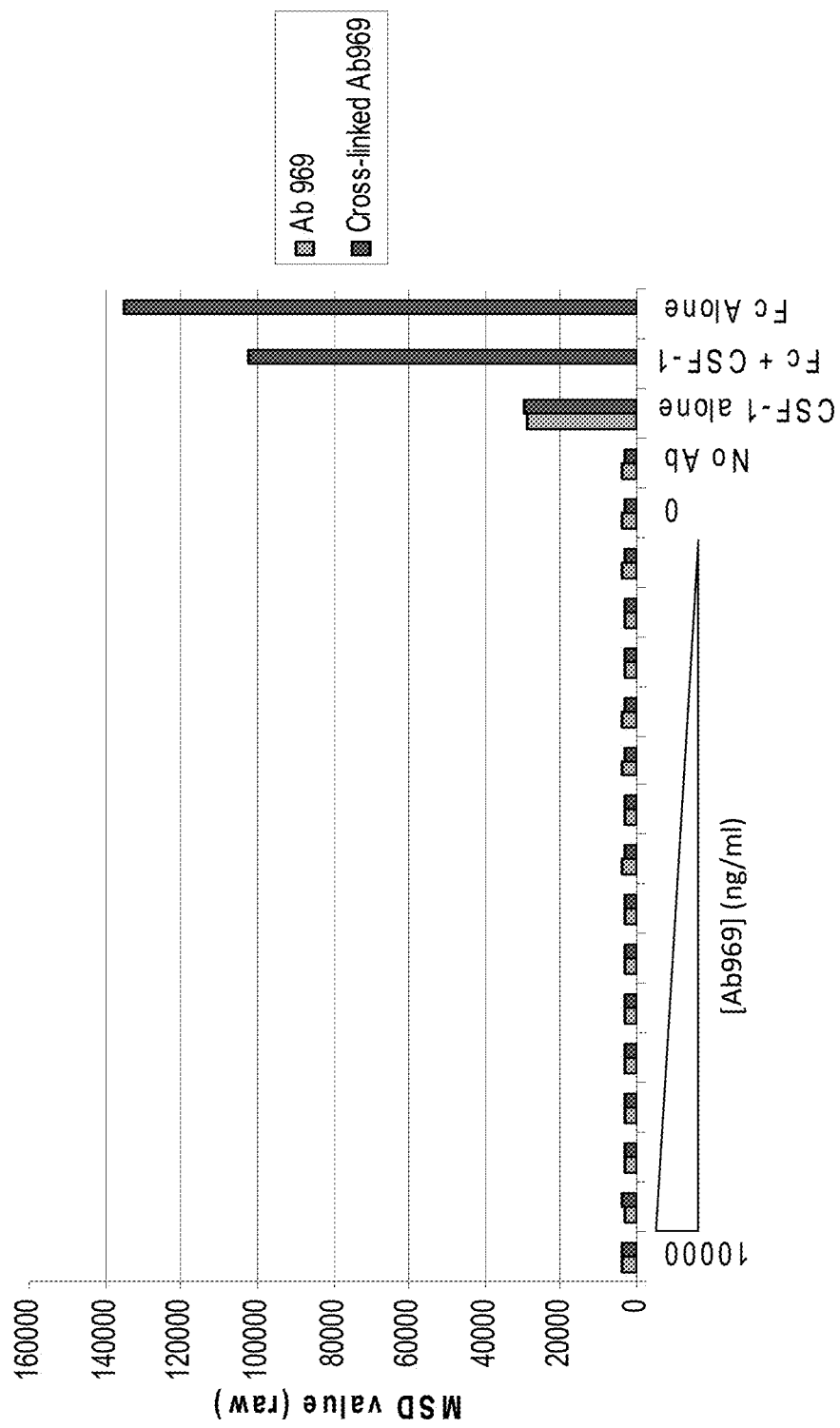
FIG. 12 shows the level of MCP-1 secretion from primary human monocytes when incubated with Ab969 and CSF-1.

The result from the experiment is shown in FIG. 12. No increase in MCP-1 levels was detected for any of the Ab969.g0 treatments, either in monomeric or cross-linked format; the concentration of MCP-1 in the medium of treated cells was identical to untreated cells. As expected, cells treated with CSF-1 gave a significant and reproducible increase in MCP-1 levels.

Example 3—Humanisation of Antibody 969 and Selection of Humanised Graft

Four anti-CSF-1R antibodies were selected for humanisation based on their affinity and properties measured in Example 2.

i) Generation of Humanised Grafts

Antibodies 969 and 970 were humanised by grafting the CDRs from the rat antibody V-regions onto human germline antibody V-region frameworks.

The CDRs grafted from the donor to the acceptor sequence are as defined by Kabat (Kabat et al., 1987), with the exception of CDR-H1, where the combined Chothia/Kabat definition is used (see Adair et al., 1991, Humanised antibodies, WO91/09967).

Human V-region VK1 2-1-(1) O12 plus JK4 J-region (V BASE, http://vbase.mrc-cpe.cam.ac.uk/) was chosen as the acceptor for the light chain CDRs. Human V-region VH2 3-1 2-70 plus JH3 J-region (V BASE, http://vbase.mrc-cpe.cam.ac.uk/) was chosen as the acceptor for the heavy chain CDRs.

A number of framework residues from the rat V-regions were retained in the humanised sequences, as shown in Table 1.

Genes encoding initial humanised light and heavy chain V-region sequences, named gL1 and gH1, respectively, were designed and constructed by an automated synthesis approach. Further variants of both the light and heavy chain V-regions were created by modifying the gL1 and gH1 genes by oligonucleotide-directed mutagenesis.

The VK genes (gL1 to gL9) were cloned into the human light chain expression vector pKH10.1, which contains DNA encoding the human Kappa chain constant region (Km3 allotype). The VH genes (gH1 and gH2) were cloned into the human gamma-4 heavy chain expression vector pVhγ4P FL, which contains DNA encoding the human gamma-4 heavy chain constant region with the hinge-stabilising mutation S241P (Angal et al., 1993, Mol Immunol., 30:105-8). Different combinations of plasmids encoding the variant light and heavy chains were co-transfected into HEK293F, resulting in the expression of the humanised, recombinant 969 antibodies.

The other three anti-CSF-1R antibodies were also humanised by providing a conservative graft containing a number of donor residues in the heavy and light chains predicted to be of importance and a fully humanised graft containing no donor residues.

ii) Affinity of Humanised Antibodies

Each humanised graft was assessed for (i) binding affinity to human CSF-1R by BIAcore and (ii) melting temperature (Tm) measured by Thermofluor analysis, both relative to the parental chimeric antibody. Melting temperature is believed to provide an early indication of the stability of an antibody molecule, with unstable antibodies typically exhibiting a Tm less than 75.0° C.

The grafts representing the stages of humanisation of Ab969 are shown in Table 5. Table 5 also shows the chimeric antibody of Ab696 (969cHcL). The conservative graft (969gH1gL1) exhibited an affinity constant ($K_D$) of 2.4 pM, so there was no apparent loss of affinity compared to the chimeric rat antibody (969cHcL). The Tm of the 969gH1gL1 conservative graft was 78.8° C. and therefore above a threshold value of 75.0° C. Substitution of the A78 donor residue for V78 in the heavy chain to produce 969gH2gL1 did not reduce antibody affinity ($K_D$=2.3 pM). Upon stepwise substitution of K38, Y71 and F87 donor residues, to Q38, F71 and Y87, respectively, no changes in affinity were observed. The final humanised graft 969gH2gL8 containing no donor residues exhibited an affinity similar to the parental chimeric antibody (4.1 pM).

TABLE 5

| Antibody Graft | VK donor residues | VH donor residues | $k_a$ ($M^{-1}s^{-1}$) | $k_d$ ($s^{-1}$) | $K_D$ (pM) |
|---|---|---|---|---|---|
| 969cHcL | N/A | N/A | 2.31E+06 | 7.99E−06 | 3.5 |
| 969gH1gL1 | K38, Y71, F87 | A78 | 2.04E+06 | 5.00E−06 | 2.4 |
| 969gH1gL2 | Y71, F87 | A78 | 1.46E+06 | 5.00E−06 | 3.4 |
| 969gH1gL3 | K38, F87 | A78 | 1.80E+06 | 5.00E−06 | 2.8 |
| 969gH1gL4 | K38, Y71 | A78 | 2.39E+06 | 5.00E−06 | 2.1 |
| 969gH1gL5 | F87 | A78 | 9.26E+05 | 6.11E−06 | 6.6 |
| 969gH1gL6 | K38 | A78 | 1.15E+06 | 5.00E−06 | 4.4 |
| 969gH1gL7 | Y71 | A78 | 1.50E+06 | 5.00E−06 | 3.3 |
| 969gH1gL8 | — | A78 | 1.17E+06 | 5.00E−06 | 4.3 |
| 969gH2gL1 | K38, Y71, F87 | — | 2.27E+06 | 5.23E−06 | 2.3 |
| 969gH2gL2 | Y71, F87 | — | 1.78E+06 | 6.11E−06 | 3.4 |
| 969gH2gL3 | K38, F87 | — | 2.12E+06 | 7.29E−06 | 3.4 |
| 969gH2gL4 | K38, Y71 | — | 2.20E+06 | 9.64E−06 | 4.4 |
| 969gH2gL5 | F87 | — | 7.68E+05 | 5.00E−06 | 6.5 |
| 969gH2gL6 | K38 | — | 1.40E+06 | 6.23E−06 | 4.4 |
| 969gH2gL7 | Y71 | — | 1.40E+06 | 5.00E−06 | 3.6 |
| 969gH2gL8 | — | — | 1.23E+06 | 5.00E−06 | 4.1 |

Ab969 possesses a potential DG isomerisation motif at the junction of CDR-L2 and the framework. This DG site aspartic acid residue in the 969gH2gL7 and 969gH2gL8 grafts was mutated to serine to give an inert SG sequence. Affinity towards CSF-1R was measured by BIAcore and no apparent loss of affinity was detected (Table 6). Furthermore, the final 969H2gL7(SG) and 969gH2gL8(SG) grafts retained a high Tm of 80.5° C. and 79.9° C., respectively.

TABLE 6

| Antibody Graft | VK donor residues | VH donor residues | $k_a$ ($M^{-1}s^{-1}$) | $k_d$ ($s^{-1}$) | $K_D$ (pM) |
|---|---|---|---|---|---|
| 969cHcL | N/A | N/A | 4.35E+06 | 8.53E−06 | 2.0 |
| 969gH2gL7 DG | Y71 | — | 2.56E+06 | 7.16E−06 | 2.8 |
| 969gH2gL7 SG | Y71 | — | 2.54E+06 | 5.00E−06 | 2.0 |
| 969gH2gL8 DG | — | — | 2.18E+06 | 5.00E−06 | 2.3 |
| 969gH2gL8 SG | — | — | 3.22E+06 | 5.00E−06 | 1.6 |

The humanisation of Ab969 and one other anti-CSF-1R antibody, Ab970, generated fully humanised antibodies (no rat donor residues present) with affinity ($K_D$) equivalent to the parental chimeric antibody and a Tm that gave an initial prediction of molecule stability. The fully humanised version of Ab969 (969gH2gL8(SG)) was renamed Ab969.g5. From here on, the chimeric version of Ab969 will be referred to as Ab969.g0.

The affinity of purified chimeric and humanised grafts of Ab969 antibodies toward recombinant CSF-1R was measured again by BIAcore analysis. Previous BIAcore experiments performed during the humanisation process were carried out using crude cell supernatants rather than purified antibody. A slight reduction in the affinity was detected, with $K_D$ values being increased from approximately 4 pM to 5 pM.

TABLE 7

| Antibody | Experiment | $k_a$ ($M^{-1}s^{-1}$) | $k_d$ ($s^{-1}$) | $K_D$ (pM) |
|---|---|---|---|---|
| 969.g0 | 1 | 2.16E+06 | 9.49E−06 | 4.4 |
|  | 2 | 2.16E+06 | 9.10E−06 | 4.2 |
|  | Mean | 2.16E+06 | 9.30E−06 | 4.3 |
| 969.g5 | 1 | 1.63E+06 | 8.13E−06 | 5.0 |
|  | 2 | 1.50E+06 | 7.96E−06 | 5.3 |
|  | Mean | 1.57E+06 | 8.05E−06 | 5.1 | iii) Inhibition of CSF-1-Mediated Monocyte Survival by Ab969.g0 and Ab969.g5

CSF-1 is required for the activation and survival of monocytes in culture; if CSF-1 is removed, then monocytes rapidly undergo apoptosis. An assay was devised that used MCP-1 (monocyte chemotactic protein-1; also known as CCL2, chemokine C-C motif ligand 2) as a readout. Upon CSF-1 stimulation, human monocytes secrete MCP-1, which can be detected in cell supernatants by an ELISA, typically 24 hours after stimulation. The inhibition of CSF-1R signalling by antibodies that block CSF-1-binding causes a reduction in MCP-1 secretion.

Human PBMCs were prepared from fresh human whole blood on a Ficoll gradient and CD14$^+$ monocytes purified by positive selection. A total of $2\times10^4$ monocytes were incubated with a half-log dilution series of 10 µg/ml to 0.35 pg/ml antibody in the presence of 100 ng/ml human CSF-1 for 24 hours. Controls comprising 'no antibody, no CSF-1' and 'no antibody, with CSF-1' were included to provide minimum and maximum MCP-1 release values. After the 24-hour incubation, cells were pelleted by centrifugation and the supernatant collected. The concentration of MCP-1 was measured using the Human CCL2/MCP-1 DuoSet ELISA (R&D Systems, DY279) following the manufacturer's instructions.

From henceforth the assay is referred to as the 'MCP-1 inhibition assay'.

The MCP-1 inhibition assay was employed to compare the activity of humanised 969.g5 with chimeric Ab969.g0. Five independent assays were performed using four different donors of monocytes. In all assays, the Ab969.g5 humanised graft exhibited an unexpected significantly lower activity compared to the parental chimeric antibody 969.g0. A single representative experiment is shown in FIG. 13. The mean $IC_{50}$ for 969.g0 in the monocyte assay was 24.6 ng/ml, compared to 333.0 ng/ml for 969.g5. This indicates a 13.5-fold decrease in antibody potency when both antibodies are compared using this assay format.

A series of experiments were performed using Ab969 in order to reveal why the humanised antibody exhibited a reduced activity in the MCP-1 inhibition assay. The data suggested that the activity loss of Ab969.g5 observed in the MCP-1 inhibition assay was due to the order in which antibody and ligand were added to the target cells. The activity of both Ab969.g0 and Ab969.g5 was reduced when a competitive assay format is applied, but more importantly, a larger differential in their blocking-activity was detected. To analyse whether a lower 'on-rate' of humanised Ab969 could be responsible for the reduction in potency a BIAcore analysis was performed. These data had identified that, while the $K_D$ of Ab969.g0 and Ab969.g5 were similar, the Ka was lower for Ab969.g5, at $1.57\times10^6$ $M^{-1}$ $s^{-1}$ compared to $2.16 \times 10^6$ M$^{-1}$ s$^{-1}$ for 969.g0 (see Table 5). In a competitive assay, where CSF-1 and the anti-CSF-1R antibody are competing for binding to the same receptor, a slower antibody on-rate could result in reduced blocking activity if the on-rate for the ligand is also high and the ligand is present at a high concentration. It is known that human CSF-1 has a particularly high on-rate at $2.19 \times 10^6$ M$^{-1}$ s$^{-1}$, similar to the antibodies, and the assay was performed with a high CSF-1 concentration (250 ng/ml).

In order to provide further evidence that the reduction in blocking activity of 969.g5 was due to an innate property of the antibody, an ELISA that measures CSF-1 binding to CSF-1R was developed. This method is from here on referred to as the 'ELISA ligand-blocking assay'. This assay was performed using competitive binding, where CSF-1 and antibody were pre-mixed before application to plate-bound CSF-1R. The assay was also carried out to assess the influence of CSF-1 concentration on antibody activity.

When the IC$_{50}$ of 969.g0 and 969.g5 was measured in the ligand-blocking ELISA using a CSF-1 concentration of ing/ml, both antibodies appeared to have similar activity, with an IC$_{50}$ of 12.83 ng/ml versus 19.65 ng/ml, respectively. When a concentration of 10 ng/ml CSF-1 was used in the assay, the IC$_{50}$ of both Ab969.g0 and Ab969.g5 increased, but more importantly, the differential between them increased further, to 79.29 ng/ml versus 268.10 ng/ml, respectively. The trend continued in an assay using 100 ng/ml CSF-1, where Ab969.g0 and Ab969.g5 gave IC$_{50}$ values of 828.70 ng/ml and 3947.00 ng/ml, respectively. A competitive assay demonstrates that Ab969.g5 is less active than Ab969.g0 at blocking CSF-1 binding to CSF-1R. This reduction in potency becomes more pronounced as the concentration of CSF-1 is increased.

Figure 14:
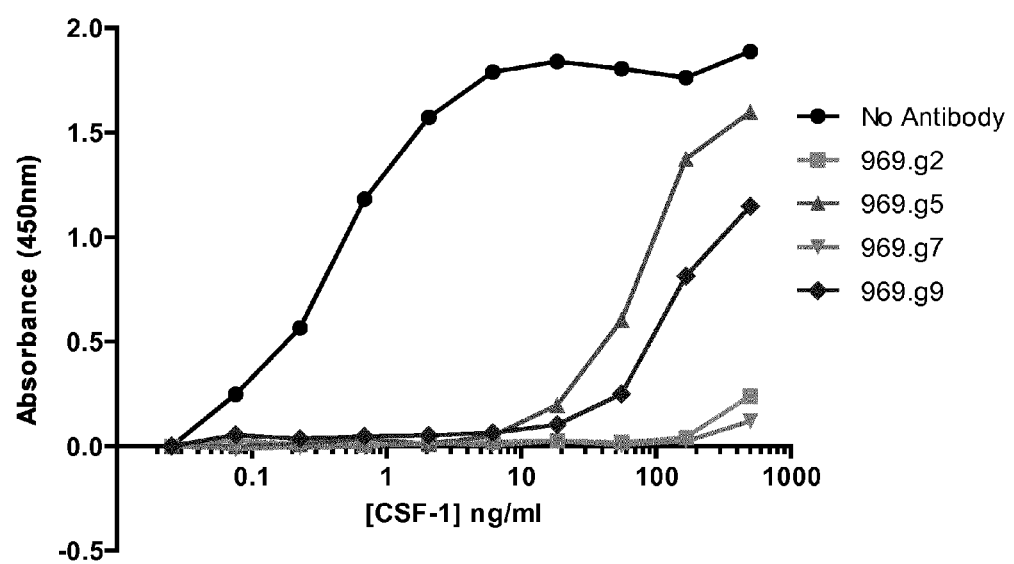
FIG. 14 shows the effect on inhibition of CSF-1-mediated monocyte survival by various humanised antibody grafts of Ab969.

The in vitro activity of each antibody was tested in the MCP-1 inhibition assay. The assay format that uses a CSF-1 titration with a single concentration of antibody was chosen, as the format enables rapid screening of a large antibody panel and highlights any differential CSF-1R blocking activity. In this assay, a dose-dependent release of MCP-1 from the primary human monocytes was detected and the relative ability of each antibody to block CSF-1R activity was measured by the concentration of CSF-1 where MCP-1 was released. Monocytes were seeded at 20,000 cells per well in media in the presence of a titration of recombinant human CSF-1 (2-fold dilution series comprising 18 concentrations, maximum 500 ng/ml). A single dose of 1 µg/ml antibody was added. Cells were incubated for 24 h and supernatant was collected. Secreted MCP-1 was measured by ELISA. The MCP-1 inhibition assay revealed that antibodies Ab969.g2 and Ab969.g7 retained high CSF-1R blocking activity, with both entities capable of completely inhibiting MCP-1 secretion when CSF-1 was added to the monocytes at a concentration greater than 100 ng/ml (FIG. 14). In this assay, a clear loss of activity was detected for Ab969.g5, which could only inhibit MCP-1 secretion up to a CSF-1 concentration of 10 ng/ml. Similarly, antibody Ab969.g9 exhibited reduced CSF-1R blocking activity compared to Ab969.g2 and Ab969.g7.

The IC$_{50}$ of selected Ab969 humanised grafts was measured in the MCP-1 assay to provide a more thorough assessment of their relative ability to inhibit CSF-1-mediated monocyte activation. It was considered important to assess antibody activity using several different donors with no pooling of monocytes from mixed sources. Table 9 shows IC$_{50}$ values of the antibodies accumulated from assays performed on Ab969 using 6 different donors.

Both the Ab969.g2 and Ab969.g7 humanised grafts exhibit a relative IC$_{50}$ that is comparable with the chimeric Ab969.g0 antibody. In stark contrast, Ab969.g5, exhibits much less potency in the assay (mean chimeric/graft IC$_{50}$ ratio of 19.6).

TABLE 9

| | | | IC$_{50}$ (ng/ml) | | | | | | | |
|---|---|---|---|---|---|---|---|---|---|---|
| Antibody | VK donor residues | VH donor residues | Donor 1 | Donor 2 | Donor 3 | Donor 4 | Donor 5 | Donor 6 | Mean ± S.E. | Mean chimeric/graft |
| 969.g0 | N/A | N/A | 31.0 | 5.7 | 59.4 | 41.7 | 20.9 | 7.1 | 27.6 +/− 8.5 | N/A |
| 969.g7 | K38, Y71 | — | 46.3 (1.5) | 6.1 (1.1) | N/A | N/A | N/A | N/A | 26.2 +/− 14.2 | 1.3 |
| 969.g2 | Y71 | — | N/A | N/A | 80.6 (1.4) | 42.2 (1.0) | 22.3 (1.1) | 14.4 (2.0) | 39.9 +/− 14.8 | 1.3 |
| 969.g5 | — (SG) | — | 667.1 (21.5) | 100.3 (17.6) | N/A | N/A | N/A | N/A | 383.7 +/− 200.4 | 19.6 | iv) Identification of Humanised Grafts of Ab 969 with Activity Equivalent to Chimeric Ab969 in MCP-1 Inhibition Assay A panel of Ab969 humanised intermediate grafts were prepared by transient expression so that in vitro activity could be compared (Table 8). The corresponding chimeric antibody (Ab969.g0) and fully humanised graft (Ab969.g5) were also included in the transient expression so that a direct comparison of antibody characteristics could be made within the same batch.

TABLE 8

| Antibody | Graft | VK donor residues | VH donor residues |
|---|---|---|---|
| 969.g0 | 969cHcL | N/A | N/A |
| 969.g7 | 969gH2gL4 | K38, Y71 | — |
| 969.g9 | 969gH2gL6 | K38 | — |
| 969.g2 | 969gH2gL7 | Y71 | — |
| 969.g5 | 969gH2gL8(SG) | — | — | v) Affinity of Humanised Ab696 Antibody Panel

The affinity of each Ab969 humanised antibody graft and the parental chimeric antibody was measured by BIAcore (Table 10), where three independent experiments were carried out and the mean values calculated. The data shows that affinity (K$_D$) does not appear to change during the humanisation process from chimeric molecule (Ab969.g0) through to the 'fully humanised' antibody Ab969.g5. However, the antibody 'on-rate' decreases when humanisation proceeds beyond the Ab969.g2 graft; both Ab969.g4 and Ab969.g5 possess lower K$_a$ values than the preceding grafts. Furthermore, the K$_a$ for Ab969.g5 is lower than Ab969.g4, potentially indicating that the mutation of the DG isomerisation site to SG reduces the antibody on-rate further still.

TABLE 10

| Antibody Graft | Antibody Name | VK donor residues | VH donor residues | $k_a$ (M$^{-1}$s$^{-1}$) | $k_d$ (s$^{-1}$) | $K_D$ (pM) |
|---|---|---|---|---|---|---|
| 969cHcL | 969.0 | N/A | N/A | 2.83E+06 | 1.03E−05 | 3.6 |
| | | | | 2.79E+06 | 1.10E−05 | 3.9 |
| | | | | 2.68E+06 | 9.51E−06 | 3.6 |
| | | | | 2.77E+06 | 1.03E−05 | 3.7 |
| 969gH1gL1 | 969.g1 | K38, Y71, F87 | A78 | 2.65E+06 | 8.47E−06 | 3.2 |
| | | | | 2.57E+06 | 6.04E−06 | 2.4 |
| | | | | 2.51E+06 | 9.88E−06 | 3.9 |
| | | | | 2.58E+06 | 8.13E−06 | 3.2 |
| 969gH2gL1 | 969.g6 | K38, Y71, F87 | — | 2.43E+06 | 8.84E−06 | 3.6 |
| | | | | 2.44E+06 | 8.95E−06 | 3.7 |
| | | | | 2.54E+06 | 6.63E−06 | 2.6 |
| | | | | 2.47E+06 | 8.14E−06 | 3.3 |
| 969gH2gL4 | 969.g7 | K38, Y71 | — | 2.57E+06 | 7.73E−06 | 3.0 |
| | | | | 2.60E+06 | 9.41E−06 | 3.6 |
| | | | | 2.52E+06 | 1.15E−05 | 4.6 |
| | | | | 2.56E+06 | 9.55E−06 | 3.7 |
| 969gH2gL7 | 969.g2 | Y71 | — | 2.46E+06 | 1.07E−05 | 4.3 |
| | | | | 2.49E+06 | 8.39E−06 | 3.4 |
| | | | | 2.44E+06 | 8.74E−06 | 3.6 |
| | | | | 2.46E+06 | 9.28E−06 | 3.8 |
| 969gH2gL8 | 969.g4 | — | — | 1.99E+06 | 5.00E−06 | 2.5 |
| | | | | 1.94E+06 | 6.65E−06 | 3.4 |
| | | | | 1.97E+06 | 5.00E−06 | 2.5 |
| | | | | 1.97E+06 | 5.55E−06 | 2.8 |
| 969gH2gL8(SG) | 969.g5 | — | — | 1.71E+06 | 5.00E−06 | 2.9 |
| | | | | 1.85E+06 | 7.03E−06 | 3.8 |
| | | | | 1.84E+06 | 6.76E−06 | 3.7 |
| | | | | 1.80E+06 | 6.26E−06 | 3.5 |

CONCLUSIONS

The testing of a panel of Ab969 humanised grafts in several assays revealed that the tyrosine residue at position 71 (e.g., Y71) within the light chain improved activity of the antibody. Substitution of Y71 for, e.g., a phenylalanine results in a reduction of antibody on-rate (decreased $K_a$) relative to the parental chimeric molecule. This results in a reduced ability of the antibody to block CSF-1 binding to CSF-1R, revealed in an assay monitoring the activity of CSF-1R in primary human monocytes (MCP-1 inhibition assay).

Example 4—Molecular Stability of Humanised Ab696 Panel i) Thermal Stability

Thermal stability (measured as melting temperature, Tm) was determined by two independent methods; one method monitors unfolding by binding of fluorescent dye to exposed hydrophobic surfaces (Thermofluor method), the other by calorimetry (DSC), an orthogonal technique.

$T_M$ measured by Thermofluor for various grafts of antibody 969 (in PBS, pH 7.4) is summarised in Table 11.

TABLE 11

| Sample | $T_m1$ Mean (° C.) | $T_m1$ S.D. (° C.) | $T_m2$ Mean (° C.) | $T_m2$ S.D. (° C.) |
|---|---|---|---|---|
| 969.g2 | 80.5 | 0.6 | 65.6 | 0.4 |
| 969.g2 | 80.5 | 0.6 | 65.6 | 0.4 |
| 969.g5 | 79.7 | 0.6 | 64.7 | 0.2 |
| 969.g5 (pH 5.0) | 82.7 | 0.1 | 59.9 | 0.5 |
| 969.g7 | 79.8 | 0.5 | 65.9 | 0.4 |
| 969.g9 | 79.4 | 0.5 | 65.8 | 0.5 |
| IgG4 Control | 66.4 | 0.8 | ND | ND |

Overall, the Fab' T. as measured by Thermofluor suggests that most 969 grafts are more thermally stable than the IgG4 control.

ii) The Effect of Sample Concentration on Aggregation Propensity

As a predictor of the stability of samples during storage, the effect of antibody concentration on stability in PBS, pH 7.4 was studied.

Experiment 1

Antibodies were concentrated to >10 mg/ml and incubated at room temperature for 5 days. Immediately after concentration (T$_0$) 969.g7 appeared cloudy and 969.g8 appeared slightly opalescent. In contrast, the 969.g5 sample was judged to be clear by visual inspection. After 5 days of incubation at room temperature, the 965.g5 sample remained clear, whereas the aggregation of 969.g7 and 969.g8 had progressed further, each exhibiting a heavy precipitate.

From this study, it was possible to rank the samples in order of resistance to aggregation in these conditions as follows: 969.g5>969.g8>969g7.

Experiment 2

Prior to concentration, all three antibody samples were clear by visual inspection, with the exception of 969.g6 (at 4.68 mg/ml) which appeared opalescent. Upon concentration to 16 mg/ml, precipitation of 969.g6 was noted after 24 hours of storage at both room temperature and 4° C. However, both 969.g1 and 969.g4 remained visibly clear. After 5 days of further incubation, large particles were evident for sample 969.g1 at both room temperature and 4° C. No aggregation was observed for sample 969.g4 at either room temperature or 4° C., as judged by visual inspection.

From this study it was possible to show that 969.g6 had some aggregation instability when stored at low concentration (4.68 mg/ml) in PBS, pH 7.4. Furthermore, this precipitation was exacerbated by further antibody concentration. Concentrated 969.g1 showed a slower rate of aggregation, whereas concentrated 969.g4 remained stable for up to 5 days at either storage temperature. The order of stability to aggregation was therefore: 969.g4>969.g1>969.g6.

Experiment 3: Antibodies 969.g2, 969.g5, 969.g7 and 969.g9

Analysis was performed on the samples immediately after concentration ($T_0$), after an overnight incubation and 5 days after concentration. All samples were clear by visual inspection before concentration and there was no evidence of particle formation. Immediately after concentration to 23.07 mg/ml, the 969.g7 sample showed precipitation, as had been observed previously in experiment 1. There was slight opalescence observed with 969.g9, which became more noticeable after 24 hours of storage at either room temperature or 4° C. All of the other 969 grafts appeared clear by visual inspection immediately post-concentration.

After 21 days incubation there was no further visible change from that observed after overnight incubation at room temperature; both the 969.g7 and 969.g9 grafts aggregated as a result of concentrating the samples, while there was no obvious visible aggregation for the other samples.

Overall the 969.g2 sample showed the least tendency to aggregate as a result of increasing the concentration. This also correlated with the highest T. as measured by Thermofluor.

Conclusion: During the expression and purification of the humanised Ab969 panel, it became apparent that increasing the antibody concentration above 10 mg/ml resulted in rapid precipitation of some humanised antibody grafts. Specifically, Ab969.g1, Ab969.g6 and Ab969.g7 formed precipitate, while Ab969.g2, Ab969.g4 and Ab969.g5 did not. This data indicates that a substitution of the lysine residue at position 38 (K38) within the light chain for glutamine improves antibody stability when concentrated above 10 mg/ml.

Example 5: In Vitro Analysis of Ab969.g2 i) Sequence of Ab969.g2

Ab969.g2 contains the gL7 light chain graft and gH2 heavy chain graft. Alignments of the rat antibody (donor) V-region sequences with the human germline (acceptor) V-region sequences are shown in FIGS. 2A and 2B, together with the final humanised sequences for the light chain graft gL7 and heavy chain graft gH2.

The heavy chain framework residues in graft gH2 are all from the human germline gene. The Glutamine residue at position 1 of the human heavy chain framework was replaced with Glutamic acid (E1) to improve the expression and purification of a homogeneous product, e.g., by the conversion of Glutamine to pyroGlutamate at the N-terminus of antibodies and antibody fragments.

The light chain framework residues in graft gL7 are all from the human germline gene, with the exception of residue 71 (Kabat numbering), where the donor residue Tyrosine was retained. Retention of this residue provided improved potency of the humanised antibody, as shown in Example 3.

ii) Inhibition of IL-34-Dependent Human Monocyte Activation

The activity of Ab969.g2 compared to 969.g0 was assessed in the IL-34-dependent human monocyte assay. The experiment was performed using two separate monocyte donors and the mean $IC_{50}$ for inhibition of IL-34-mediated monocyte stimulation was calculated (Table 12). There was no significant difference in $IC_{50}$ between Ab969.g2 and Ab969.g0.

Primary human monocytes were seeded at 20,000 cells per well in the presence of 100 ng/ml recombinant human IL-34 and a dose titration of anti-CSF-1R antibody (half-log dilution series comprising 16 concentrations, maximum 10 µg/ml). Cells were incubated for 24 hours and supernatant was collected. Secreted MCP-1 was measured by ELISA (R&D Systems, DY279). The graph shows the percentage inhibition of MCP-1 production compared to the CSF-1-only control.

TABLE 12

| Antibody | $IC_{50}$ (ng/ml) | | |
|---|---|---|---|
| | Donor 1 | Donor 2 | Mean ± S.E. |
| 969.g0 | 20.10 | 9.79 | 14.95 +/− 5.17 |
| 969.g2 | 20.58 | 9.59 | 15.09 +/− 5.51 | iii) Binding of Ab969.g2 to SNPs of Human CSF-1R

There are four non-synonymous single-nucleotide polymorphisms (SNPs) located within the ligand-binding domain of the human CSF-1R gene that have been reported in the human population. These SNPs are V32G, A245S, H247P and V279M (FIG. 1F). Each SNP variant of human CSF-1R was generated and stably expressed in cell lines. Binding of Ab969.g2 to each SNP was confirmed by flow cytometry.

Example 6: Pharmacodynamic Marker Analysis in Cynomolgus Monkey

A pharmacokinetic/pharmacodynamic (PK/PD) study with the humanised monoclonal anti-CSF-1R antibody 969.g2 was performed to demonstrate the pharmacological activity of the antibody in a non-human primate (cynomolgus monkey). Groups of three cynomolgus monkeys were dosed intravenously with a single dose of either 7 mg/kg (Group 1) or 1.5 mg/kg (Group 2) 969.g2 antibody. The antibody was well-tolerated with no adverse clinical signs. Serum samples were taken at multiple timepoints throughout the 25-day study.

The serum concentration of 969.g2 was measured by ELISA and pharmacokinetic analysis was performed (Table 13). PK parameters were calculated using WinNonlin software. $t_{1/2}$ is half-life of antibody in serum.

$C_{max}$ is peak concentration of antibody in serum.

AUC is the area under the curve (the integral of the concentration-time curve) and provides an indication of total exposure to the drug.

Clearance is the volume of plasma cleared of drug per unit of time.

Vol. Dist. is the volume of distribution, the apparent volume in which a drug is distributed.

There was a good correlation between observed and predicted values (animal 2 being an exception and regarded as an outlier). $C_{max}$ was proportional to the dose; AUC was greater than dose-proportional, indicating slower clearance at the higher dose. The majority of 969.g2 was detected in the serum.

TABLE 13

| Animal | Dose [mg/kg] | t½ [h] | Cmax [µg/mL] | AUC$_{INF\_obs}$ [h*µg/mL] | Clearance (Cl$_{obs}$) [mL/h/kg] | Vol. Distribution (V$_{z\_obs}$) [mL/kg] |
|---|---|---|---|---|---|---|
| 1 | 7 | 66.1 | 209.4 | 23184.5 | 0.30 | 28.8 |
| 2 | 7 | 30.3 | 117.6 | 6075.9 | 1.15 | 50.4 |
| 3 | 7 | 63.3 | 188.7 | 16761.0 | 0.42 | 38.1 |
| 4 | 1.5 | 27.9 | 36.1 | 1928.1 | 0.78 | 31.3 |
| 5 | 1.5 | 22.7 | 34.7 | 1668.6 | 0.90 | 29.5 |
| 6 | 1.5 | 27.1 | 36.6 | 1634.8 | 0.92 | 35.9 |

The primary route for clearance of CSF-1 is through binding to its cognate receptor, CSF-1R. Blockade of CSF-1 binding to CSF-1R is expected to increase the serum concentration of CSF-1 though prevention of receptor-mediated clearance, a phenomenon that has been observed in murine models. Therefore, an increase in serum CSF-1 concentration is a pharmacodynamic marker of CSF-1R engagement and inhibition.

Both doses of 969.g2 instigated a rapid and significant accumulation of serum CSF-1. The effect was dose-dependent, with the 7 mg/kg dose giving a peak CSF-1 concentration of approximately 10-fold higher than the 1.5 mg/kg dose. A pharmacokinetic/pharmacodynamic relationship was observed with normalisation of CSF-1 levels following clearance of the antibody. CSF-1 levels returned to baseline by the end of the study for both treatment groups. Results are shown in FIGS. 15a and 15b.

Figure 15A:
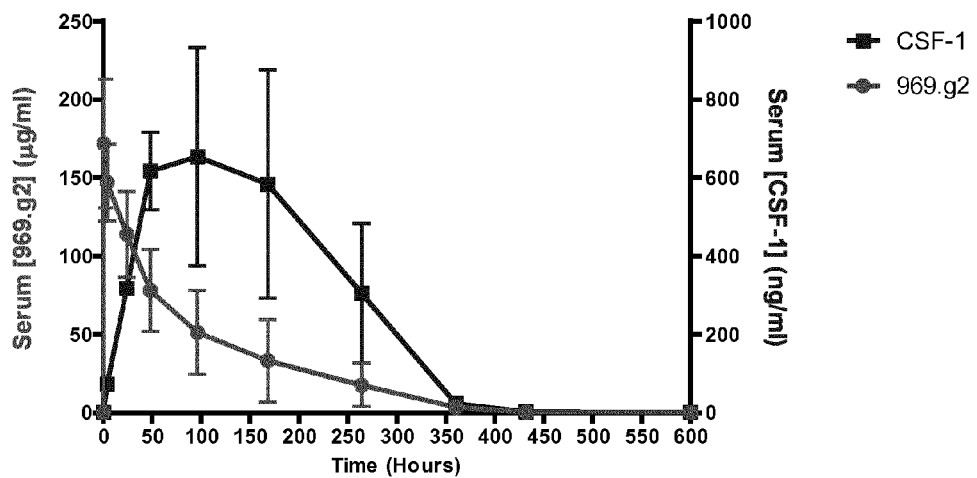
FIG. 15a shows the concentration of CSF-1 in serum samples taken from cynomolgus monkeys treated with a single intravenous dose of 7 mg/kg Ab969.g2.

FIG. 15a shows the concentration of CSF-1 in serum samples taken from cynomolgus monkeys treated with a single intravenous dose of 7 mg/kg Ab969.g2. The serum concentration of CSF-1 was measured in two independent assays. The graph shows the mean concentration of CSF-1 for the three animals in Group 1 (7 mg/kg) with standard error (squares). Also shown is the mean serum concentration of Ab969.g2 (circles).

Figure 15B:
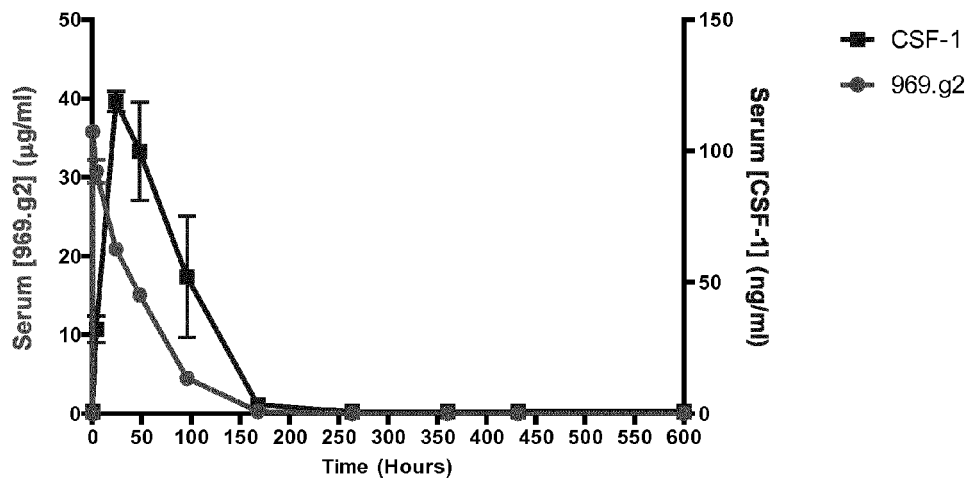
FIG. 15b shows the concentration of CSF-1 in serum samples taken from cynomolgus monkeys treated with a single intravenous dose of 1.5 mg/kg Ab969.g2.

FIG. 15b shows the concentration of CSF-1 in serum samples taken from cynomolgus monkeys treated with a single intravenous dose of 1.5 mg/kg Ab969.g2. The serum concentration of CSF-1 was measured in two independent assays. The graph shows the mean concentration of CSF-1 for the three animals in Group 2 (1.5 mg/kg) with standard error (squares). Also shown is the mean serum concentration of Ab969.g2 (circles).

There are two major populations of circulating human and cynomolgus monkey monocytes: (i) CD14+CD16− 'classical' monocytes and (ii) CD14+CD16+ 'non-classical' or 'resident' monocytes. Murine models have demonstrated that resident tissue macrophages, including TAMs, are derived from the non-classical monocyte population. Furthermore, non-classical monocytes are derived from further differentiation of the classical monocyte population. Circulating monocyte populations in cynomolgus monkeys dosed with 969.g2 were monitored by four-colour flow cytometry of whole blood. Flow cytometry was performed using anti-cyno-CD45-PerCP, anti-human-HLA-DR-APC, anti-human-CD14-FITC (My4 clone) and anti-human-CD16-PE (3G8 clone) antibodies. Gates were set using the appropriate isotype control for each antibody. Classical monocytes were defined as CD45+ HLA-DR+ CD14+ CD16−. Non-classical monocytes were defined as CD45+ HLA-DR+ CD14+ CD16+.

Figure 15C:
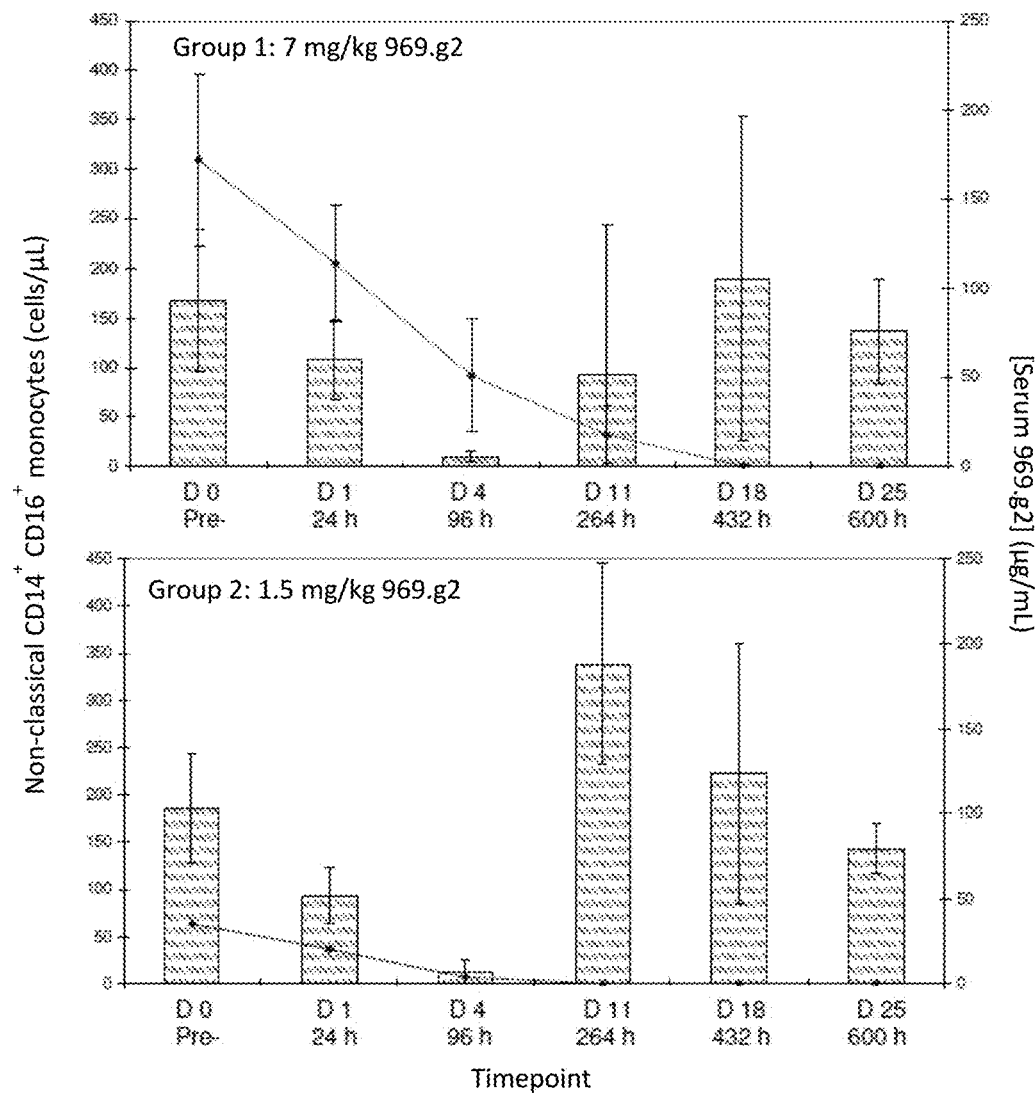
FIG. 15c shows the effect of administering antibody Ab969.g2 to cynomolgus monkeys at dosages of 7 mg/kg and 1.5 mg/kg on circulating non-classical monocytes at different timepoints.

Both doses of 969.g2 instigated a gradual depletion of non-classical CD14+ CD16+ monocytes throughout the first week of the study. Almost total depletion of non-classical monocytes was caused by the 7 mg/kg dose. Non-classical monocyte reduction by both 7 mg/kg and 1.5 mg/kg doses appeared to peak at the day 4 timepoint, with numbers returning to normal by day 11. Results are shown in FIG. 15c. The bar graphs show the mean number of circulating non-classical CD14+ CD16+ monocytes at timepoints throughout the study (days (D) 0, 1, 4, 18 and 25) with standard error. The mean concentration of serum CSF-1 is also plotted with standard error.

This example (i) confirmed that antibody 969.g2 was capable of binding CSF-1R and blocking CSF-1 binding in the cynomolgus monkey, (ii) demonstrated pharmacological activity of the antibody 969.g2 in a non-human primate model, (iii) demonstrated that antibody 969.g2 selectively depleted the non-classical population of cynomolgus monkey monocytes in vivo—the monocyte population believed to be precursors of tumour-associated macrophages, and (iv) that serum CSF-1 concentration was suitable as a biomarker for measuring 969.g2 activity.

Example 7: Inhibition of Growth of MCF-7 Breast Cancer Xenograft

Antibody 969.g2 is not capable of binding to mouse CSF-1R. Accordingly, in vivo mouse studies were carried out using an anti-murine CSF-1R antibody Ab535 to show the utility of Ab969.g2 in treating cancer and fibrosis. Ab535 has been shown to have comparable properties and activity to Ab969.g2 in a number of in vitro experiments.

Ab535 has been shown to inhibit CSF-1-mediated monocyte survival in Example 2 iii), has a comparable affinity in Example 2 iv) and does not trigger CSF-1R internalization in Example 2 vii).

An in vivo study on Ab535 in the in vivo MCF-7 breast cancer xenograft model was carried out as follows:

The study measured the therapeutic efficacy of the antibody Ab535, administered subcutaneously (s.c.), vs. a control antibody, a positive control and the vehicle control in immunodeficient nude mice bearing subcutaneous transplants of the human breast cancer xenograft MCF-7. Tumour growth inhibition was used as a therapeutic parameter. The human breast cancer MCF-7 was used as subcutaneous xenotransplantation model in immunodeficient female NMRT:nu/nu mice. The MCF-7 cell line was obtained from the tumour bank of the National Cancer Institute (USA). For experimental use, cells were cultivated in vitro in RPMI 1640 medium+10% FCS. Cells were taken from sub-confluent cultures and inoculated subcutaneously into mice. At palpable tumour size (4-10 mm) treatment started. The test compounds and the vehicle control were given s.c. three times per week. The positive control was administered intravenously once daily on days 24, 33 and 40. The injection volumes were individually adjusted to the body weight at time of injection. Tumour diameters were measured three times weekly with a caliper. Tumour volumes were calculated according to V=(length×(width)2)/2. For calculation of the relative tumour volume (RTV), the volumes at each measurement day were related to the day of first treatment. At each measurement day the median and mean tumour volumes per group and also the median treated to control (T/C) values in percent were calculated.

Figure 16:
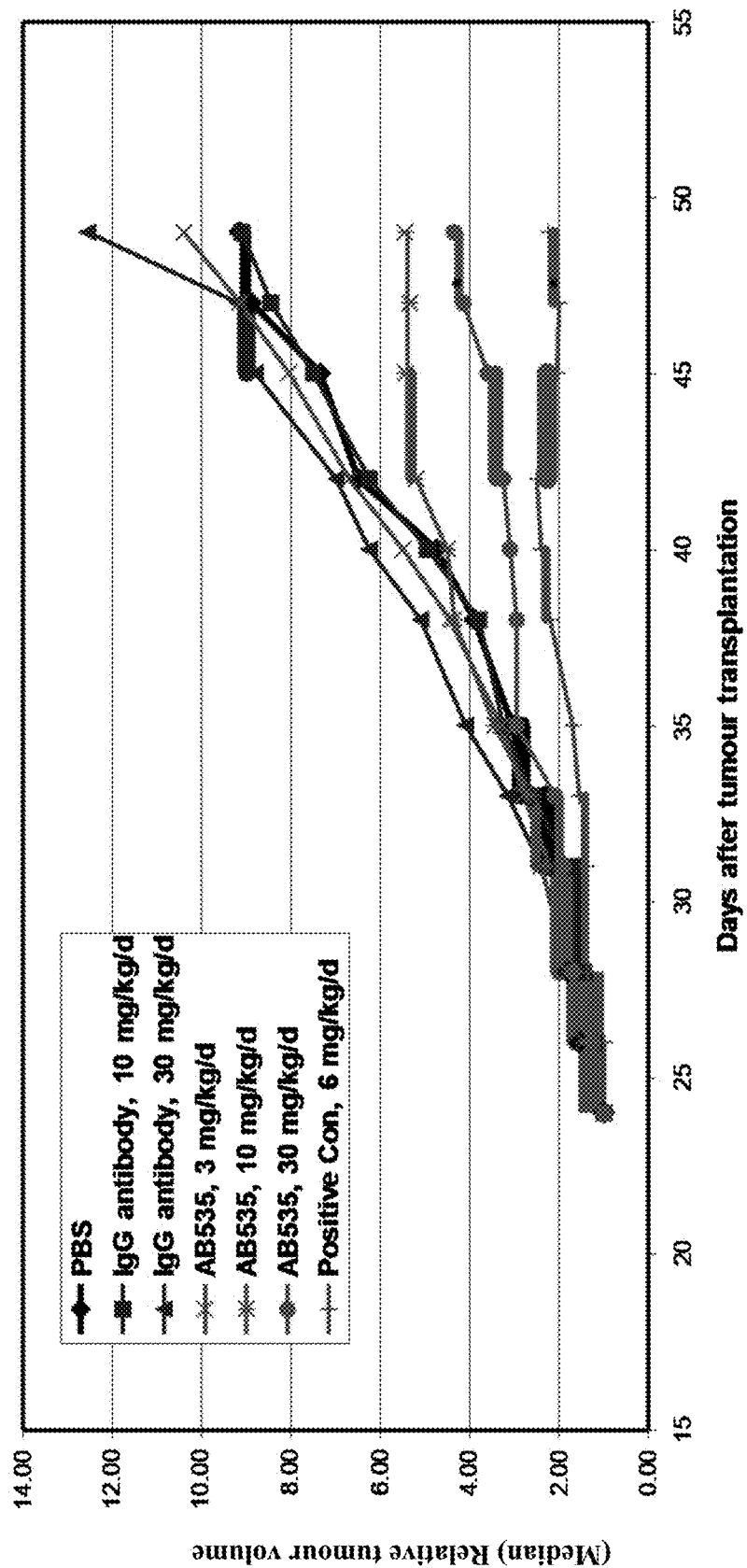
FIG. 16 shows the antitumor effect of antibody Ab535 vs. a control antibody, a positive control and the vehicle control in immunodeficient nude mice bearing subcutaneous transplants of the human breast cancer xenograft MCF-7.

Results are shown in FIG. 16. Ab535 showed a dose-dependent antitumour effect. Both dosages of the control mouse IgG antibody did not induce a tumour growth inhibition. Relative tumour volumes were comparable with the vehicle control and the positive control caused tumour growth inhibition.

Conclusion: The test antibody Ab535 induced a statically significant antitumour effect in the human breast cancer xenograft MCF-7 at the highest dose (30 mg/kg/day).

Example 8: Inhibition of Growth of PC-3 Orthotopic Prostate Cancer

The antitumoral and antimetastatic efficacy of antibody Ab535 was also tested using an orthotopic prostate cancer model PC-3 in vivo. The PC-3 cell line was genetically altered to continuously express luciferase, allowing in vivo bioluminescence imaging analysis, which allowed monitoring of tumour growth in vivo and performance of ex vivo metastasis analysis in selected organs.

The study consisted of 6 experimental groups, each containing either 11 (Group 5) or 12 (all other groups) male NMRI nude mice after randomization. At day 0, PC-3 cells were orthotopically implanted into the prostates of all participating male NMRI nude mice. On day 3, the onset of tumor growth was verified via in vivo bioluminescence imaging. On day 8, a second in vivo bioluminescence imaging was performed and tumor-bearing animals were randomized into six groups according to the imaging results, such that mean bioluminescence intensity and thus tumor size was similar in each group. On the following day (day 9), therapy was initiated. Animals of Groups 2 and 3 received 30 and 10 mg/kg of Control Antibody, respectively, 3×weekly s.c. until day 42. Animals of Treatment Groups 4 and 5 received 30 and 10 mg/kg of antibody Ab535, respectively, 3× weekly s.c. until day 42. Animals of Group 1 represented the Vehicle Control and received Vehicle (PBS) 3× weekly s.c. until day 42. Animals of Group 6 represented the Positive Control and received 360 mg/kg control i.v. once weekly for four weeks (on days 10, 17, 24 and 31). During the course of the study, the growth of the orthotopically implanted PC-3 tumors was monitored in vivo on days 3, 8 (randomization), 15, 22, 29, 36 and 43 using bioluminescence imaging.

A necropsy was performed at the study end. Primary tumor weight and volume were determined. Selected organs (liver, spleen and lung) were collected, a portion of each fixed in formalin and the remainder analyzed regarding the metastasis pattern via bioluminescence imaging using an in vitro luciferase assay. Additionally, the femur from one leg and the same portion of lumbar spine were collected for analyzing the metastasis pattern in bones using the in vitro luciferase assay.

Figure 17:
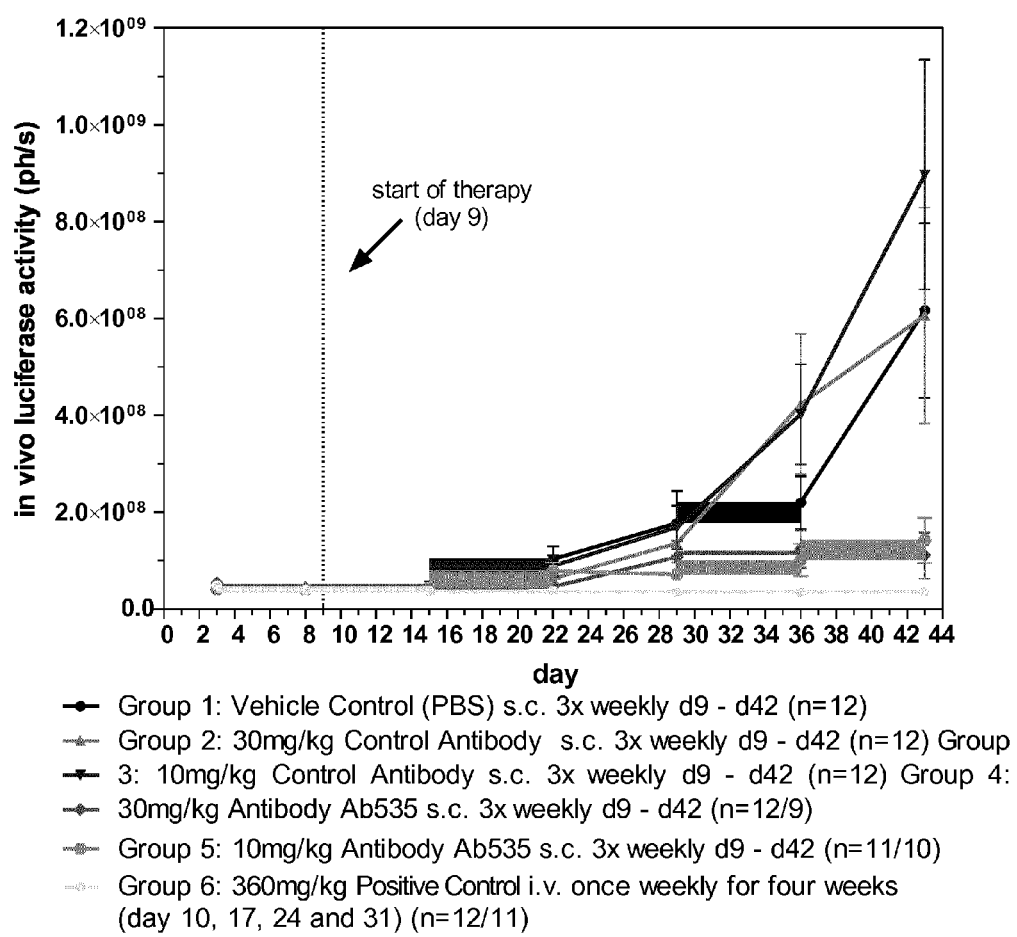
FIG. 17 shows the antitumoral efficacy of antibody Ab535 vs. a control antibody, a positive control and the vehicle control in an orthotopic prostate cancer model PC-3.

The in vivo bioluminescence signal was composed of both primary tumor and metastasis (whole body imaging). Based on these data, a tumor growth curve could be calculated for all groups (FIG. 17). Tumor development was homogeneous within all study groups until randomization and start of therapy. In the following, Vehicle Control Group 1 as well as the two Control Antibody RTE11 Groups 2 and 3 showed a regular tumor growth. A highly significant reduction of tumor growth measured in vivo on day 43 could be observed for the positive control (Group 6). Antibody Ab535, administered at 30 or 10 mg/kg, respectively (Groups 4 and 5), led to a significant reduction of tumor growth when monitored using in vivo bioluminescence imaging.

Primary tumor volumes and wet weights were determined during necropsy on day 44. The Positive Control (Group 6) led to a highly significant reduction of both primary tumor volume and weight. When antibody Ab535 was administered at 30 mg/kg (Group 4), a significant reduction of both primary tumor volume and weight could be observed. When Ab535 was administered at 10 mg/kg (Group 5), reduction of tumour volume was noticeable but less than shown by Group 4. No significant antitumoral efficacy could be observed in case of the Control Antibody.

Using the bioluminescence imaging technique, primary tumor luciferase activities were measured post-necropsy. The results obtained were comparable to the results of the necropsy findings and the in vivo growth curve. Positive control (Group 6) led to a highly significant reduction of the primary tumor luciferase activity. Antibody Ab535, administered at 30 mg/kg (Group 4), led to a significant reduction of the primary tumor luciferase activity, whereas the reduction was less when Ab535 was administered at 10 mg/kg (Group 5). No significant reduction of the luciferase activity could be found for the Control Antibody.

Several additional organs (liver, spleen, lung, femur and a part of the lumbar spine) were analyzed using the ex vivo bioluminescence imaging technique. In the case of the positive control, significant reductions of luciferase activity could be shown for the femur and lumbar spine, whereas the signal reduction was just below significance in the case of the liver and spleen. In the case of Antibody Ab535, administered at 30 mg/kg (Group 4), the reduction of luciferase activity was significant for the liver and noticeable for all other organs. The Control Antibody (Groups 2 and 3) did not lead to any reduction of luciferase activity in all organs tested.

In conclusion, a significant antitumoral efficacy could be demonstrated for the antibody Ab535 in this tumor model, combined with a noticeable antimetastatic efficacy.

Example 9: Effect of Anti-CSF-1R Antibody in a Bleomycin-Induced In Vivo Model of Pulmonary Fibrosis Bleomycin is an antibiotic first isolated from *Streptomyces verticillatus* and has been used as a chemotherapeutic for various cancers. The bleomycin model of lung fibrosis is a well-established model and was used essentially as described in Madtes, D. K. et al., 1999, Am. J. Respir. Cell Mol. Biol., 20:924-34. The detailed protocol can be found in Morschl, E., Molina, J. G., Volmer, J., Mohsenin, A., Pero, R. S., Hong, J. S., Kheradmand, F., Lee, J. J. and Blackburn, M. R. (2008), A3 adenosine receptor signaling influences pulmonary inflammation and fibrosis, Am. J. Respir. Cell Mol. Biol., 39:697-705.

All mice used were wild type C57Blk6 female mice (20 g) purchased from Harlan Laboratories. An intra-tracheal (IT) cut down instillation was used where mice were anaesthetised with avertin and a tracheostomy performed in order to instill a 3.5 unit dose of bleomycin in 50 µl of saline or 50 µl of saline alone as a control. Treatment in this manner leads to an inflammatory phase that peaks on day 7 after bleomycin exposure and a fibrotic phase that is maximum on day 21-post exposure. The effect of antibody Ab535 was investigated where antibody was dosed only in the fibrotic phase of the model and was administered subcutaneously at 30 mg/kg, three times per week from day 9-21. Animals were sacrificed at day 21 and readouts included histopathological analysis of the lungs, BAL (bronchoalveolar lavage) fluid cellularity and the measurement of soluble collagen in BAL fluid. Histopathological analysis was conducted to score lung damage using a modified Ashcroft scoring system to determine the severity of lung fibrosis (Hubner, R. H. et al., 2008, Biotechniques, 44:507-17). Excised lungs were inflated with 10% formalin to 25 cm pressure and processed through a series of alcohols and xylene, and embedded in paraffin, and tissue sections de-paraffinised prior to processing and staining with Masson's Trichrome.

The amount of soluble collagen in BAL fluid was assessed using a commercially available Sircol assay kit following the manufacturer's instructions.

The effect on the macrophage population in the BAL fluid was determined using cytospin preparations. Aliquots of BAL cells were spun onto microscope slides, stained with Diff-Quik and macrophages counted.

It was found that therapeutic treatment with the anti-CSF-1R antibody, Ab535, with dosing started at day 9 resulted in greatly reduced bleomycin-induced lung fibrosis. Both the severity and extent of fibrosis was significantly reduced. The treated mice had reduced collagen production, improved fibrotic pathology and improved pulmonary barrier protection.

FIG. 18a shows that treatment of bleomycin-induced lung fibrosis with Ab535 reduced BALF collagen concentration compared to treatment with the isotype control.

FIG. 18b shows that treatment of bleomycin-induced lung fibrosis with Ab535 reduced the Ashcroft score of the samples compared to treatment with the isotype control, which thus shows that the mice treated with Ab535 had improved fibrotic pathology.

FIG. 18c shows that treatment of bleomycin-induced lung fibrosis with Ab535 reduced the concentration of albumin in the serum compared to treatment with the isotype control, which thus shows that the vascular permeability of the mice treated with Ab535 was improved.

FIG. 19 shows representative images of the histopathological analysis of lungs from saline control, bleomycin plus isotype control and bleomycin plus Ab535-treated animals. Animals treated with Ab535 had a greatly reduced fibrosis of the lungs compared to the isotype control and bleomycin-treated animals.

Example 10. Effect of Anti-CSF-1R Antibody in an Adenosine Deaminase-Deficient Mouse Model of Pulmonary Fibrosis Adenosine is a potent signalling nucleoside, the levels of which increase when cells suffer stress or are damaged, and a wide variety of responses are produced when adenosine engages its specific G protein-coupled receptors. Adenosine deaminase (ADA) is a purine catabolism enzyme that converts adenosine to inosine. ADA knockout mice have been generated and shown to have increased levels of adenosine in serum as well as in tissues such as kidney, liver and lung (Blackburn, M. R. et al., 1998, J. Biol. Chem., 273(9):5093-5100). These mice exhibit features of chronic lung disease, such as alveolar destruction, airway inflammation and excessive mucus production, which are associated with increased levels of adenosine in the lung (Blackburn, M. R. et al., 2000, J. Exp. Med., 192:159-70). The effects are such that the mice die by three weeks of age due to respiratory distress. Administration of exogenous ADA using a low-dose regimen reduces adenosine levels and extends the lifespan of these mice, allowing a model of pulmonary fibrosis to be developed (Chunn, J. L. et al., 2005, J. Immunol., 175:1937-46; Pedroza, M. et al., 2011, PLoS One, 6(7):e22667). In this model, chronic elevation of adenosine levels is associated with an increase in pro-fibrotic mediators including TGFβ-1 in the lungs, increased collagen deposition in lung tissue and increased fibrotic lung pathology. To investigate the effect of molecules with anti-fibrotic potential, ADA-deficient mice are maintained on a low-dose exogenous ADA regimen for several weeks; the ADA treatment is then stopped and the potential anti-fibrotic agent administered.

The effect of the anti-CSF-1R antibody Ab535 was investigated in the ADA knockout mouse model of pulmonary fibrosis. In this model, the enzyme-deficient mice were maintained on ADA enzyme therapy from day 1 to day 21 post-birth. An ADA-polyethylene glycol (PEG) conjugate was prepared (Young, H. W. et al., 2004, J. Immunol., 173:1380-89) and intramuscular injections were administered on postnatal days 1, 5, 9, 13 and 17 (0.625, 1.25, 2.5, 2.5 and 2.5 units, respectively), followed by 5 units injected intraperitoneally on day 21. No further enzyme was administered after day 21. Ab535 was dosed subcutaneously at 30 mg/kg, in a volume of 100 µl three times/week from day 25 (post-natally) until the animals were sacrificed on day 42.

Animals were sacrificed on day 42 and readouts included histopathological analysis of the lungs, BAL fluid cellularity and quantitation of soluble collagen in BAL fluid. Histopathological analysis was conducted to score lung damage using a modified Ashcroft scoring system to determine the severity of lung fibrosis (Hubner et al., 2008, Biotechniques 44: 507-17). Excised lungs were inflated with 10% formalin to 25 cm pressure and processed through a series of alcohols and xylene, and embedded in paraffin, and tissue sections de-paraffinised prior to processing and staining with Masson's Trichrome.

The amount of soluble collagen in BAL fluid was also assessed using a commercially available Sircol assay kit following the manufacturer's instructions.

The effect on the macrophage population in the BAL fluid was determined using cytospin preparations. Aliquots of BAL cells were spun onto microscope slides, stained with Diff-Quik and macrophages counted.

It was found that therapeutic treatment with anti-CSF-1R antibody Ab535 significantly reduced lung fibrosis in ADA-deficient mice. The treated mice had reduced collagen production, improved fibrotic pathology and improved pulmonary barrier function and protection.

FIG. 20a shows that treatment of ADA-deficient mice with induced lung fibrosis with Ab535 reduced BALF collagen concentration compared to treatment with the isotype control.

FIG. 20b shows that treatment of ADA-deficient mice with induced lung fibrosis with Ab535 reduced the Ashcroft score of the samples compared to treatment with the isotype control, which thus shows that the mice treated with Ab535 had improved fibrotic pathology.

FIG. 20c shows that treatment of ADA-deficient mice with induced lung fibrosis with Ab535 reduced the concentration of albumin in the serum compared to treatment with the isotype control, which thus shows that the vascular permeability of the mice treated with Ab535 was improved.

FIG. 20d shows that treatment of ADA-deficient mice with induced lung fibrosis receiving Ab535 had reduced numbers of macrophages in BAL fluid.

FIG. 21 shows representative images of the histopathological analysis of lungs from normal mice (ADA+) and ADA-deficient mice with induced lung fibrosis (ADA−), both treated with isotype control or Ab535. In the ADA− mice, animals treated with Ab535 had greatly reduced fibrosis of the lungs compared to the isotype control.

Accordingly, it has been shown in two mouse models of lung fibrosis that treatment with an anti-CSF-1R antibody can effectively treat fibrotic disease.

The invention claimed is:

1. An anti-colony stimulating factor 1 receptor (CSF-1R) antibody comprising:
   i) a heavy chain, wherein the variable domain of the heavy chain comprises SEQ ID NO:4 for CDR-H1, SEQ ID NO:5 for CDR-H2 and SEQ ID NO:6 for CDR-H3; and
   ii) a light chain, wherein the variable domain of the light chain comprises SEQ ID NO:1 for CDR-L1, SEQ ID NO:2 for CDR-L2 and SEQ ID NO:3 for CDR-L3.

2. The anti-CSF-1R antibody according to claim 1, wherein the heavy chain comprises SEQ ID NO:23.

3. The anti-CSF-1R antibody according to claim 1, wherein the light chain comprises SEQ ID NO:15.

4. The anti-CSF-1R antibody according to claim 1, wherein the antibody molecule is selected from the group consisting of: a complete antibody molecule having full length heavy and light chains or an antigen binding fragment thereof.

5. The anti-CSF-1R antibody according to claim 1, said antibody having an effector or a reporter molecule attached to it.

6. The anti-CSF-1R antibody according to claim 1, having a binding affinity for human CSF-1R of 10 pM or less.

7. An isolated DNA sequence encoding the heavy and/or light chain(s) of an antibody according to claim 1.

8. A cloning or expression vector comprising one or more DNA sequences according to claim 7.

9. The vector according to claim 8, wherein the vector comprises SEQ ID NO:28 and/or SEQ ID NO:20.

10. A host cell comprising one or more cloning or expression vectors according to claim 9.

11. A process for the production of an antibody, comprising culturing the host cell of claim 10 and isolating the antibody.

12. A pharmaceutical composition comprising an antibody according to claim 1, in combination with one or more of a pharmaceutically acceptable excipient, diluent or carrier, wherein the pharmaceutical composition optionally comprises other active ingredients.

13. An anti-colony stimulating factor 1 receptor (CSF-1R) antibody, having a heavy chain comprising SEQ ID NO:23 and a light chain comprising SEQ ID NO: 15, or having a heavy chain comprising SEQ ID NO:27 and a light chain comprising SEQ ID NO:19.

* * * * *

UNITED STATES PATENT AND TRADEMARK OFFICE
CERTIFICATE OF CORRECTION

PATENT NO. : 9,908,939 B2
APPLICATION NO. : 14/914676
DATED : March 6, 2018
INVENTOR(S) : Graham Craggs, Karine Jeannine Madeleine Hervé and Diane Marshall Page 1 of 1

It is certified that error appears in the above-identified patent and that said Letters Patent is hereby corrected as shown below:

In the Specification

Column 32,
Line 28, "of 5000" should read --of ~5000--.

Column 39,
Line 22, "ing/ml" should read --1ng/ml--.

Column 43,
Line 28, "T. as" should read --$T_m$ as--.

Signed and Sealed this
Fourth Day of December, 2018

Andrei Iancu
*Director of the United States Patent and Trademark Office*

SEQUENCE LISTING

<160> NUMBER OF SEQ ID NOS: 39

<210> SEQ ID NO 1
<211> LENGTH: 11
<212> TYPE: PRT
<213> ORGANISM: Artificial Sequence
<220> FEATURE:
<223> OTHER INFORMATION: CA019_969 Ab sequences CDR-L1

<400> SEQUENCE: 1

Leu Ala Ser Glu Asp Ile Tyr Asp Asn Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CA019_969 Ab sequences CDRL2

<400> SEQUENCE: 2

Tyr Ala Ser Ser Leu Gln Asp
1               5

<210> SEQ ID NO 3
<211> LENGTH: 9
<212> TYPE: PRT
<213> ORGANISM: Artificial Sequence
<220> FEATURE:
<223> OTHER INFORMATION: CA019_969 Ab sequences CDR-L3

<400> SEQUENCE: 3

Leu Gln Asp Ser Glu Tyr Pro Trp Thr
1               5

<210> SEQ ID NO 4
<211> LENGTH: 12
<212> TYPE: PRT
<213> ORGANISM: Artificial Sequence
<220> FEATURE:
<223> OTHER INFORMATION: CA019_969 Ab sequences CDR-H1

<400> SEQUENCE: 4

Gly Phe Ser Leu Thr Thr Tyr Gly Met Gly Val Gly
1               5                   10

<210> SEQ ID NO 5
<211> LENGTH: 16
<212> TYPE: PRT
<213> ORGANISM: Artificial Sequence
<220> FEATURE:
<223> OTHER INFORMATION: CA019_969 Ab sequences CDR-H2

<400> SEQUENCE: 5

Asn Ile Trp Trp Asp Asp Asp Lys Tyr Tyr Asn Pro Ser Leu Lys Asn
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: CA019_969 Ab sequences CDR-H3

<400> SEQUENCE: 6

Ile Gly Pro Ile Lys Tyr Pro Thr Ala Pro Tyr Arg Tyr Phe Asp Phe
1               5                   10                  15

<210> SEQ ID NO 7
<211> LENGTH: 107
<212> TYPE: PRT
<213> ORGANISM: Artificial Sequence
<220> FEATURE:
<223> OTHER INFORMATION: Rat Ab 969 VL region

<400> SEQUENCE: 7

Asp Ile Gln Met Thr Gln Ser Pro Ala Ser Leu Ser Ala Ser Leu Gly
 1               5                  10                  15

Glu Thr Val Ser Ile Glu Cys Leu Ala Ser Glu Asp Ile Tyr Asp Asn
             20                  25                  30

Leu Ala Trp Tyr Gln Lys Lys Pro Gly Lys Ser Pro His Leu Leu Ile
         35                  40                  45

Tyr Tyr Ala Ser Ser Leu Gln Asp Gly Val Pro Ser Arg Phe Ser Gly
     50                  55                  60

Ser Gly Ser Gly Thr Gln Tyr Ser Leu Lys Ile Asn Ser Leu Glu Ser
 65                  70                  75                  80

Glu Asp Ala Ala Thr Tyr Phe Cys Leu Gln Asp Ser Glu Tyr Pro Trp
                 85                  90                  95

Thr Phe Gly Gly Gly Thr Lys Leu Glu Leu Lys
            100                 105

<210> SEQ ID NO 8
<211> LENGTH: 321
<212> TYPE: DNA
<213> ORGANISM: Artificial Sequence
<220> FEATURE:
<223> OTHER INFORMATION: Rat Ab 969 VL region

<400> SEQUENCE: 8
gacatccaga tgacacagtc tccagcttcc ctgtctgcat ctctgggaga aactgtctcc      60
atcgaatgtc tagcaagtga ggacatttac gataatttag cgtggtacca gaagaagcca     120
ggaaaatctc ctcacctcct catctattat gcaagtagct tgcaagatgg ggtcccatca     180
cggttcagtg gcagtggatc tggcacacag tattctctca aaatcaacag cctggaatct     240
gaagatgctg cgacttattt ctgtctacag gattctgagt atccgtggac gttcggtgga     300
ggcaccaagc tggaattgaa a                                               321

<210> SEQ ID NO 9
<211> LENGTH: 127
<212> TYPE: PRT
<213> ORGANISM: Artificial Sequence
<220> FEATURE:
<223> OTHER INFORMATION: Rat Ab 969 VL region with signal sequence
      underlined and italicized

<400> SEQUENCE: 9

Met Gly Val Pro Thr Gln Leu Leu Val Leu Leu Leu Leu Trp Ile Thr
 1               5                  10                  15

Asp Ala Ile Cys Asp Ile Gln Met Thr Gln Ser Pro Ala Ser Leu Ser
             20                  25                  30

Ala Ser Leu Gly Glu Thr Val Ser Ile Glu Cys Leu Ala Ser Glu Asp
         35                  40                  45

Ile Tyr Asp Asn Leu Ala Trp Tyr Gln Lys Lys Pro Gly Lys Ser Pro
     50                  55                  60

His Leu Leu Ile Tyr Tyr Ala Ser Ser Leu Gln Asp Gly Val Pro Ser
 65                  70                  75                  80

```
Arg Phe Ser Gly Ser Gly Ser Gly Thr Gln Tyr Ser Leu Lys Ile Asn
                85                  90                  95

Ser Leu Glu Ser Glu Asp Ala Ala Thr Tyr Phe Cys Leu Gln Asp Ser
            100                 105                 110

Glu Tyr Pro Trp Thr Phe Gly Gly Gly Thr Lys Leu Glu Leu Lys
        115                 120                 125

<210> SEQ ID NO 10
<211> LENGTH: 381
<212> TYPE: DNA
<213> ORGANISM: Artificial Sequence
<220> FEATURE:
<223> OTHER INFORMATION: Rat Ab 969 VL region with signal sequence
      underlined and italicized

<400> SEQUENCE: 10
atgggtgtcc ccactcagct cttggtgttg ttgctgctgt ggattacaga tgccatatgt      60
gacatccaga tgacacagtc tccagcttcc ctgtctgcat ctctgggaga aactgtctcc     120
atcgaatgtc tagcaagtga ggacatttac gataatttag cgtggtacca agaagaagcca    180 ggaaaatctc ctcacctcct catctattat gcaagtagct tgcaagatgg ggtcccatca     240
cggttcagtg gcagtggatc tggcacacag tattctctca aaatcaacag cctggaatct     300
gaagatgctg cgacttattt ctgtctacag gattctgagt atccgtggac gttcggtgga     360
ggcaccaagc tggaattgaa a                                               381

<210> SEQ ID NO 11
<211> LENGTH: 125
<212> TYPE: PRT
<213> ORGANISM: Artificial Sequence
<220> FEATURE:
<223> OTHER INFORMATION: Rat Ab 969 VH region

<400> SEQUENCE: 11

Gln Val Thr Leu Lys Glu Ser Gly Pro Gly Ile Leu Gln Pro Ser Gln
1               5                   10                  15

Thr Leu Ser Leu Thr Cys Thr Phe Ser Gly Phe Ser Leu Thr Thr Tyr
            20                  25                  30

Gly Met Gly Val Gly Trp Ile Arg Gln Pro Ser Gly Lys Gly Leu Glu
        35                  40                  45

Trp Leu Ala Asn Ile Trp Trp Asp Asp Lys Tyr Tyr Asn Pro Ser
    50                  55                  60

Leu Lys Asn Arg Leu Thr Ile Ser Lys Asp Thr Ser Asn Asn Gln Ala
65                  70                  75                  80

Phe Leu Lys Leu Thr Asn Val His Thr Ser Asp Ser Ala Thr Tyr Tyr
                85                  90                  95

Cys Ala Arg Ile Gly Pro Ile Lys Tyr Pro Thr Ala Pro Tyr Arg Tyr
            100                 105                 110

Phe Asp Phe Trp Gly Pro Gly Thr Met Val Thr Val Ser
        115                 120                 125

<210> SEQ ID NO 12
<211> LENGTH: 375
<212> TYPE: DNA
<213> ORGANISM: Artificial Sequence
<220> FEATURE:
<223> OTHER INFORMATION: Rat Ab 969 VH region

<400> SEQUENCE: 12
```

```
caggttactc tgaaagagtc tggccctggg atattgcagc cctcccagac cctcagtctg    60
acttgcactt tctctgggtt ttcactgacc acttatggta tgggtgtggg ctggattcgt   120
cagccttcag ggaagggtct ggagtggctg gcaaacattt ggtgggatga tgataagtat   180
tacaatccat ctctgaaaaa ccggctcaca atctccaagg acacctccaa caaccaagca   240
ttcctcaagc tcaccaatgt acacacttca gattctgcca catactactg tgctcggata   300
gggccgatta aatacccgac ggccccctac cggtactttg acttctgggg cccaggaacc   360
atggtcaccg tctcg                                                    375
```

<210> SEQ ID NO 13
<211> LENGTH: 144
<212> TYPE: PRT
<213> ORGANISM: Artificial Sequence
<220> FEATURE:
<223> OTHER INFORMATION: Rat Ab 969 VH region with signal sequence
      underlined and italicized

<400> SEQUENCE: 13

```
Met Asp Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Thr Phe Ser Gly Phe Ser Leu
        35                  40                  45

Thr Thr Tyr Gly Met Gly Val Gly Trp Ile Arg Gln Pro Ser Gly Lys
    50                  55                  60

Gly Leu Glu Trp Leu Ala Asn Ile Trp Trp Asp Asp Asp Lys Tyr Tyr
65                  70                  75                  80

Asn Pro Ser Leu Lys Asn Arg Leu Thr Ile Ser Lys Asp Thr Ser Asn
                85                  90                  95

Asn Gln Ala Phe Leu Lys Leu Thr Asn Val His Thr Ser Asp Ser Ala
            100                 105                 110

Thr Tyr Tyr Cys Ala Arg Ile Gly Pro Ile Lys Tyr Pro Thr Ala Pro
        115                 120                 125

Tyr Arg Tyr Phe Asp Phe Trp Gly Pro Gly Thr Met Val Thr Val Ser
    130                 135                 140
```

<210> SEQ ID NO 14
<211> LENGTH: 432
<212> TYPE: DNA
<213> ORGANISM: Artificial Sequence
<220> FEATURE:
<223> OTHER INFORMATION: Rat Ab 969 VH region with signal sequence
      underlined and italicized

<400> SEQUENCE: 14

```
atggacaggc ttacttcctc attcctactg ctgattgtcc ctgcatatgt cctgtctcag    60
gttactctga aagagtctgg ccctgggata ttgcagccct cccagaccct cagtctgact   120
tgcactttct ctgggttttc actgaccact tatggtatgg gtgtgggctg gattcgtcag   180
ccttcaggga agggtctgga gtggctggca aacatttggt gggatgatga taagtattac   240
aatccatctc tgaaaaaccg gctcacaatc tccaaggaca cctccaacaa ccaagcattc   300
ctcaagctca ccaatgtaca cacttcagat tctgccacat actactgtgc tcggataggg   360
ccgattaaat acccgacggc cccctaccgg tactttgact tctggggccc aggaaccatg   420
gtcaccgtct cg                                                       432
```

<210> SEQ ID NO 15
<211> LENGTH: 107
<212> TYPE: PRT
<213> ORGANISM: Artificial Sequence
<220> FEATURE:
<223> OTHER INFORMATION: 969 gL7 V-region

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Asp Ile Tyr Asp Asn
            20                  25                  30

Leu Ala Trp Tyr Gln Gln Lys Pro Gly Lys Ala Pro Lys Leu Leu Ile
        35                  40                  45

Tyr Tyr Ala Ser Ser Leu Gln Asp Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Asp Ser Glu Tyr Pro Trp
                85                  90                  95

Thr Phe Gly Gly Gly Thr Lys Val Glu Ile Lys
            100                 105

<210> SEQ ID NO 16
<211> LENGTH: 321
<212> TYPE: DNA
<213> ORGANISM: Artificial Sequence
<220> FEATURE:
<223> OTHER INFORMATION: 969 gL7 V-region

<400> SEQUENCE: 16
gacatacaga tgactcagtc accctcaagc ctgagtgcca gtgtgggaga cagggtgaca      60
atcacctgtc tggcctccga ggatatctac gataacctgg catggtatca gcagaaacct     120
ggaaaggctc ccaagctcct gatttattat gcctcctctc tccaagacgg cgttccatct     180
cggttcagcg gaagcggctc cgggacggat tacacactga caattagctc tctgcaaccg     240
gaggattttg ctacttacta ctgcctgcaa gactccgaat accatggac cttcggtggt      300 ggcaccaaag tggaaatcaa g                                                321

<210> SEQ ID NO 17
<211> LENGTH: 127
<212> TYPE: PRT
<213> ORGANISM: Artificial Sequence
<220> FEATURE:
<223> OTHER INFORMATION: 969 gL7 V-region with signal sequence
      underlined and italicized

<400> SEQUENCE: 17

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Leu Ala Ser Glu Asp
        35                  40                  45

Ile Tyr Asp Asn Leu Ala Trp Tyr Gln Gln Lys Pro Gly Lys Ala Pro
    50                  55                  60

Lys Leu Leu Ile Tyr Tyr Ala Ser Ser Leu Gln Asp Gly Val Pro Ser
65                  70                  75                  80

```
Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Leu Gln Asp Ser
            100                 105                 110

Glu Tyr Pro Trp Thr Phe Gly Gly Gly Thr Lys Val Glu Ile Lys
        115                 120                 125

<210> SEQ ID NO 18
<211> LENGTH: 381
<212> TYPE: DNA
<213> ORGANISM: Artificial Sequence
<220> FEATURE:
<223> OTHER INFORMATION: 969 gL7 V-region with signal sequence
      underlined and italicized

<400> SEQUENCE: 18
atgagcgtgc ctactcaagt cttggggctg ctcttgcttt ggcttaccga cgcaagatgc      60
gacatacaga tgactcagtc accctcaagc ctgagtgcca gtgtgggaga cagggtgaca     120
atcacctgtc tggcctccga ggatatctac gataacctgg catggtatca gcagaaacct     180
ggaaaggctc ccaagctcct gatttattat gcctcctctc tccaagacgg cgttccatct     240
cggttcagcg gaagcggctc cgggacggat tacacactga caattagctc tctgcaaccg     300
gaggattttg ctacttacta ctgcctgcaa gactccgaat acccatggac cttcggtggt     360
ggcaccaaag tggaaatcaa g                                               381

<210> SEQ ID NO 19
<211> LENGTH: 214
<212> TYPE: PRT
<213> ORGANISM: Artificial Sequence
<220> FEATURE:
<223> OTHER INFORMATION: 969 gL7 light chain (V + constant)

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Asp Ile Tyr Asp Asn
            20                  25                  30

Leu Ala Trp Tyr Gln Gln Lys Pro Gly Lys Ala Pro Lys Leu Leu Ile
        35                  40                  45

Tyr Tyr Ala Ser Ser Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Asp Ser Glu Tyr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 642
<212> TYPE: DNA
<213> ORGANISM: Artificial Sequence
<220> FEATURE:
<223> OTHER INFORMATION: 969 gL7 light chain (V + constant)

<400> SEQUENCE: 20
gacatacaga tgactcagtc accctcaagc ctgagtgcca gtgtgggaga cagggtgaca      60
atcacctgtc tggcctccga ggatatctac gataacctgg catggtatca gcagaaacct     120
ggaaaggctc ccaagctcct gatttattat gcctcctctc tccaagacgg cgttccatct     180
cggttcagcg gaagcggctc cgggacggat tacacactga caattagctc tctgcaaccg     240
gaggattttg ctacttacta ctgcctgcaa gactccgaat acccatggac cttcggtggt     300
ggcaccaaag tggaaatcaa gcgtacggta gcggccccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga aaacacaaa gtctacgcct gcgaagtcac ccatcagggc      600
ctgagctcgc ccgtcacaaa gagcttcaac aggggagagt gt                        642

<210> SEQ ID NO 21
<211> LENGTH: 234
<212> TYPE: PRT
<213> ORGANISM: Artificial Sequence
<220> FEATURE:
<223> OTHER INFORMATION: 969 gL7 light chain (V + constant) with signal
      sequence underlined and italicized

<400> SEQUENCE: 21

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Leu Ala Ser Glu Asp
        35                  40                  45

Ile Tyr Asp Asn Leu Ala Trp Tyr Gln Gln Lys Pro Gly Lys Ala Pro
    50                  55                  60

Lys Leu Leu Ile Tyr Tyr Ala Ser Ser Leu Gln Asp Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Leu Gln Asp Ser
            100                 105                 110

Glu Tyr Pro Trp Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
            165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 22
<211> LENGTH: 702
<212> TYPE: DNA
<213> ORGANISM: Artificial Sequence
<220> FEATURE:
<223> OTHER INFORMATION: 969 gL7 light chain (V + constant) with signal
      sequence underlined and italicized

<400> SEQUENCE: 22
atgagcgtgc ctactcaagt cttggggctg ctcttgcttt ggcttaccga cgcaagatgc      60
gacatacaga tgactcagtc accctcaagc ctgagtgcca gtgtgggaga cagggtgaca     120
atcacctgtc tggcctccga ggatatctac gataacctgg catggtatca gcagaaacct     180
ggaaaggctc ccaagctcct gatttattat gcctcctctc tccaagacgg cgttccatct     240
cggttcagcg gaagcggctc cgggacggat tacacactga caattagctc tctgcaaccg     300
gaggattttg ctacttacta ctgcctgcaa gactccgaat acccatggac cttcggtggt     360
ggcaccaaag tggaaatcaa gcgtacggta gcggcccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag cacccctgacg    600
ctgagcaaag cagactacga gaaacacaaa gtctacgcct gcgaagtcac ccatcagggc     660
ctgagctcgc ccgtcacaaa gagcttcaac aggggagagt gt                        702

<210> SEQ ID NO 23
<211> LENGTH: 125
<212> TYPE: PRT
<213> ORGANISM: Artificial Sequence
<220> FEATURE:
<223> OTHER INFORMATION: 969 gH2 V-region

<400> SEQUENCE: 23

Glu Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Thr Thr Tyr
            20                  25                  30

Gly Met Gly Val Gly Trp Ile Arg Gln Pro Pro Gly Lys Ala Leu Glu
        35                  40                  45

Trp Leu Ala Asn Ile Trp Trp Asp Asp Asp Lys Tyr Tyr Asn Pro Ser
    50                  55                  60

Leu Lys Asn Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

```
Cys Ala Arg Ile Gly Pro Ile Lys Tyr Pro Thr Ala Pro Arg Tyr
            100                 105                 110

Phe Asp Phe Trp Gly Gln Gly Thr Met Val Thr Val Ser
        115                 120                 125

<210> SEQ ID NO 24
<211> LENGTH: 375
<212> TYPE: DNA
<213> ORGANISM: Artificial Sequence
<220> FEATURE:
<223> OTHER INFORMATION: 969 gH2 V-region

<400> SEQUENCE: 24
gaagtgacac tcaaggagtc tggacccgct ctggtgaaac caacccaaac actcactttg    60
acatgtactt ttagtggctt ctcattgact acctatggaa tgggcgtggg atggatcaga   120
cagccacctg gcaaggctct ggaatggctg gccaacatct ggtgggatga cgacaagtac   180
tataacccgt ccctgaaaaa ccggctgacc attagcaagg atacttctaa aaatcaagtg   240
gtgctgacca tgacaaatat ggatcccgtt gacaccgcaa cctactactg cgcccgcatt   300
ggtcccataa agtaccctac ggcaccttac cgatatttcg acttttgggg ccaagggaca   360
atggttactg tctcg                                                   375

<210> SEQ ID NO 25
<211> LENGTH: 144
<212> TYPE: PRT
<213> ORGANISM: Artificial Sequence
<220> FEATURE:
<223> OTHER INFORMATION: 969 gH2 V-region with signal sequence
      underlined and italicized

<400> SEQUENCE: 25

Met Glu Trp Ser Trp Val Phe Leu Phe Phe Leu Ser Val Thr Thr Gly
1               5                   10                  15

Val His Ser Glu Val Thr Leu Lys Glu Ser Gly Pro Ala Leu Val Lys
            20                  25                  30

Pro Thr Gln Thr Leu Thr Leu Thr Cys Thr Phe Ser Gly Phe Ser Leu
        35                  40                  45

Thr Thr Tyr Gly Met Gly Val Gly Trp Ile Arg Gln Pro Pro Gly Lys
    50                  55                  60

Ala Leu Glu Trp Leu Ala Asn Ile Trp Trp Asp Asp Asp Lys Tyr Tyr
65                  70                  75                  80

Asn Pro Ser Leu Lys Asn Arg Leu Thr Ile Ser Lys Asp Thr Ser Lys
                85                  90                  95

Asn Gln Val Val Leu Thr Met Thr Asn Met Asp Pro Val Asp Thr Ala
            100                 105                 110

Thr Tyr Tyr Cys Ala Arg Ile Gly Pro Ile Lys Tyr Pro Thr Ala Pro
        115                 120                 125

Tyr Arg Tyr Phe Asp Phe Trp Gly Gln Gly Thr Met Val Thr Val Ser
    130                 135                 140

<210> SEQ ID NO 26
<211> LENGTH: 432
<212> TYPE: DNA
<213> ORGANISM: Artificial Sequence
<220> FEATURE:
<223> OTHER INFORMATION: 969 gH2 V-region with signal sequence
      underlined and italicized

<400> SEQUENCE: 26
```

```
atggagtggt cctgggtgtt tctgttcttc ctgagtgtga ccaccggggt ccactccgaa      60
gtgacactca aggagtctgg acccgctctg gtgaaaccaa cccaaacact cactttgaca     120
tgtactttta gtggcttctc attgactacc tatggaatgg gcgtgggatg gatcagacag     180
ccacctggca aggctctgga atggctggcc aacatctggt gggatgacga caagtactat     240
aacccgtccc tgaaaaaccg gctgaccatt agcaaggata cttctaaaaa tcaagtggtg     300
ctgaccatga caaatatgga tcccgttgac accgcaacct actactgcgc ccgcattggt     360
cccataaagt accctacggc accttaccga tatttcgact tttggggcca agggacaatg     420
gttactgtct cg                                                         432
```

```
<210> SEQ ID NO 27
<211> LENGTH: 453
<212> TYPE: PRT
<213> ORGANISM: Artificial Sequence
<220> FEATURE:
<223> OTHER INFORMATION: 969 gH2 heavy chain (V + constant - hu IgG4P)

<400> SEQUENCE: 27
```

| | | | | | | | | | | | | |
|---|---|---|---|---|---|---|---|---|---|---|---|---|
| Glu | Val | Thr | Leu | Lys | Glu | Ser | Gly | Pro | Ala | Leu | Val | Lys | Pro | Thr | Gln |
| 1 | | | | 5 | | | | | 10 | | | | | 15 | |

Glu Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Thr Thr Tyr
                20                  25                  30

Gly Met Gly Val Gly Trp Ile Arg Gln Pro Pro Gly Lys Ala Leu Glu
            35                  40                  45

Trp Leu Ala Asn Ile Trp Trp Asp Asp Asp Lys Tyr Tyr Asn Pro Ser
        50                  55                  60

Leu Lys Asn Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Gly Pro Ile Lys Tyr Pro Thr Ala Pro Tyr Arg Tyr
            100                 105                 110

Phe Asp Phe Trp Gly Gln Gly Thr Met Val Thr Val Ser Ser Ala Ser
        115                 120                 125

Thr Lys Gly Pro Ser Val Phe Pro Leu Ala Pro Cys Ser Arg Ser Thr
130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

```
Glu Val His Asn Ala Lys Thr Lys Pro Arg Glu Glu Gln Phe Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly Lys
    450

<210> SEQ ID NO 28
<211> LENGTH: 1966
<212> TYPE: DNA
<213> ORGANISM: Artificial Sequence
<220> FEATURE:
<223> OTHER INFORMATION: 969 gH2 heavy chain (V + constant - hu IgG4P,
      exons underlined)

<400> SEQUENCE: 28
gaagtgacac tcaaggagtc tggacccgct ctggtgaaac caacccaaac actcactttg      60
acatgtactt ttagtggctt ctcattgact acctatggaa tgggcgtggg atggatcaga     120
cagccacctg gcaaggctct ggaatggctg gccaacatct ggtgggatga cgacaagtac     180
tataacccgt ccctgaaaaa ccggctgacc attagcaagg atacttctaa aaatcaagtg     240
gtgctgacca tgacaaatat ggatcccgtt gacaccgcaa cctactactg cgcccgcatt     300
ggtcccataa agtaccctac ggcaccttac cgatatttcg acttttgggg ccaagggaca     360
atggttactg tctcgagcgc ttctacaaag ggcccatccg tcttccccct ggcgccctgc     420
tccaggagca cctccgagag cacagccgcc ctgggctgcc tggtcaagga ctacttcccc     480
gaaccggtga cggtgtcgtg gaactcaggc gccctgacca gcggcgtgca caccttcccg     540
gctgtcctac agtcctcagg actctactcc ctcagcagcg tggtgaccgt gccctccagc     600
agcttgggca cgaagaccta cacctgcaac gtagatcaca agcccagcaa caccaaggtg     660
gacaagagag ttggtgagag gccagcacag ggagggaggg tgtctgctgg aagccaggct     720
cagcccctcc tgcctggacg caccccggct gcagccccca gcccagggca gcaaggcatg     780
ccccatctgt ctcctcaccc ggaggcctct gaccacccca ctcatgccca gggagagggt     840
cttctggatt tttccaccag gctccgggca gccacaggct ggatgcccct accccaggcc     900
ctgcgcatac aggggcaggt gctgcgctca gacctgccaa gagccatatc cgggaggacc     960
ctgcccctga cctaagccca ccccaaaggc caaactctcc actccctcag ctcagacacc    1020
```

```
ttctctcctc ccagatctga gtaactccca atcttctctc tgcagagtcc aaatatggtc    1080
ccccatgccc accatgccca ggtaagccaa cccaggcctc gccctccagc tcaaggcggg    1140
acaggtgccc tagagtagcc tgcatccagg acaggcccc  agccgggtgc tgacgcatcc    1200
acctccatct cttcctcagc acctgagttc ctgggggac  catcagtctt cctgttcccc    1260
ccaaaaccca aggacactct catgatctcc cggacccctg aggtcacgtg cgtggtggtg    1320
gacgtgagcc aggaagaccc cgaggtccag ttcaactggt acgtggatgg cgtggaggtg    1380
cataatgcca agacaaagcc gcgggaggag cagttcaaca gcacgtaccg tgtggtcagc    1440
gtcctcaccg tcctgcacca ggactggctg aacggcaagg agtacaagtg caaggtctcc    1500
aacaaaggcc tcccgtcctc catcgagaaa accatctcca aagccaaagg tgggacccac    1560
ggggtgcgag ggccacatgg acagaggtca gctcggccca ccctctgccc tgggagtgac    1620
cgctgtgcca acctctgtcc ctacagggca gccccgagag ccacaggtgt acaccctgcc    1680
cccatcccag gaggagatga ccaagaacca ggtcagcctg acctgcctgg tcaaaggctt    1740
ctaccccagc gacatcgccg tggagtggga gagcaatggg cagccggaga caactacaa    1800 gaccacgcct cccgtgctgg actccgacgg ctccttcttc ctctacagca ggctaaccgt    1860
ggacaagagc aggtggcagg aggggaatgt cttctcatgc tccgtgatgc atgaggctct    1920
gcacaaccac tacacacaga agagcctctc cctgtctctg ggtaaa                   1966
```

<210> SEQ ID NO 29
<211> LENGTH: 472
<212> TYPE: PRT
<213> ORGANISM: Artificial Sequence
<220> FEATURE:
<223> OTHER INFORMATION: 969 gH2 heavy chain (V + constant - hu IgG4P)
      with signal sequence underlined and italicized

<400> SEQUENCE: 29

```
Met Glu Trp Ser Trp Val Phe Leu Phe Phe Leu Ser Val Thr Thr Gly
1               5                   10                  15

Val His Ser Glu Val Thr Leu Lys Glu Ser Gly Pro Ala Leu Val Lys
            20                  25                  30

Pro Thr Gln Thr Leu Thr Leu Thr Cys Thr Phe Ser Gly Phe Ser Leu
        35                  40                  45

Thr Thr Tyr Gly Met Gly Val Gly Trp Ile Arg Gln Pro Pro Gly Lys
    50                  55                  60

Ala Leu Glu Trp Leu Ala Asn Ile Trp Trp Asp Asp Lys Tyr Tyr
65                  70                  75                  80

Asn Pro Ser Leu Lys Asn Arg Leu Thr Ile Ser Lys Asp Thr Ser Lys
                85                  90                  95

Asn Gln Val Val Leu Thr Met Thr Asn Met Asp Pro Val Asp Thr Ala
            100                 105                 110

Thr Tyr Tyr Cys Ala Arg Ile Gly Pro Ile Lys Tyr Pro Thr Ala Pro
        115                 120                 125

Tyr Arg Tyr Phe Asp Phe Trp Gly Gln Gly Thr Met Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190
```

Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Lys
        210                 215                 220

Thr Tyr Thr Cys Asn Val Asp His Lys Pro Ser Asn Thr Lys Val Asp
225                 230                 235                 240

Lys Arg Val Glu Ser Lys Tyr Gly Pro Pro Cys Pro Pro Cys Pro Ala
                245                 250                 255

Pro Glu Phe Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser Gln Glu Asp Pro Glu Val Gln Phe Asn Trp Tyr Val
290                 295                 300

Asp Gly Val Glu Val His Asn Ala Lys Thr Lys Pro Arg Glu Glu Gln
305                 310                 315                 320

Phe Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Gly
            340                 345                 350

Leu Pro Ser Ser Ile Glu Lys Thr Ile Ser Lys Ala Lys Gly Gln Pro
        355                 360                 365

Arg Glu Pro Gln Val Tyr Thr Leu Pro Pro Ser Gln Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Arg Leu Thr Val Asp Lys Ser Arg Trp Gln Glu Gly Asn Val Phe
        435                 440                 445

Ser Cys Ser Val Met His Glu Ala Leu His Asn His Tyr Thr Gln Lys
450                 455                 460

Ser Leu Ser Leu Ser Leu Gly Lys
465                 470

<210> SEQ ID NO 30
<211> LENGTH: 2023
<212> TYPE: DNA
<213> ORGANISM: Artificial Sequence
<220> FEATURE:
<223> OTHER INFORMATION: 969 gH2 heavy chain (V + constant - hu IgG4P,
      exons underlined) with signal sequence underlined and italicized

<400> SEQUENCE: 30
atggagtggt cctgggtgtt tctgttcttc ctgagtgtga ccaccggggt ccactccgaa    60
gtgacactca aggagtctgg acccgctctg gtgaaaccaa cccaaacact cactttgaca   120
tgtactttta gtggcttctc attgactacc tatggaatgg gcgtgggatg gatcagacag   180
ccacctggca aggctctgga atggctggcc aacatctggt gggatgacga caagtactat   240
aacccgtccc tgaaaaaccg gctgaccatt agcaaggata cttctaaaaa tcaagtggtg   300
ctgaccatga caaatatgga tcccgttgac accgcaacct actactgcgc ccgcattggt   360
cccataaagt acccctacgg caccttaccg atatttcgact tttggggcca aggacaatg   420

```
gttactgtct cgagcgcttc tacaaagggc ccatccgtct tccccctggc gccctgctcc    480
aggagcacct ccgagagcac agccgccctg ggctgcctgg tcaaggacta cttccccgaa    540
ccggtgacgg tgtcgtggaa ctcaggcgcc ctgaccagcg gcgtgcacac cttcccggct    600
gtcctacagt cctcaggact ctactccctc agcagcgtgg tgaccgtgcc ctccagcagc    660
ttgggcacga agacctacac ctgcaacgta gatcacaagc ccagcaacac caaggtggac    720
aagagagttg gtgagaggcc agcacaggga gggagggtgt ctgctggaag ccaggctcag    780
ccctcctgcc tggacgcacc ccggctgtgc agccccagcc cagggcagca aggcatgccc    840
catctgtctc ctcacccgga ggcctctgac caccccactc atgcccaggg agagggtctt    900
ctggattttt ccaccaggct ccgggcagcc acaggctgga tgcccctacc ccaggccctg    960
cgcatacagg ggcaggtgct cgcgtcagac ctgccaagag ccatatccgg gaggaccctg   1020
cccctgacct aagcccaccc caaaggccaa actctccact ccctcagctc agacaccttc   1080
tctcctccca gatctgagta actcccaatc ttctctctgc agagtccaaa tatggtcccc   1140
catgcccacc atgcccaggt aagccaaccc aggcctcgcc ctccagctca aggcgggaca   1200
ggtgccctag agtagcctgc atccaggac aggccccagc cgggtgctga cgcatccacc   1260
tccatctctt cctcagcacc tgagttcctg ggggaccat cagtcttcct gttcccccca   1320
aaacccaagg acactctcat gatctcccgg acccctgagg tcacgtgcgt ggtggtggac   1380
gtgagccagg aagaccccga ggtccagttc aactggtacg tggatggcgt ggaggtgcat   1440
aatgccaaga caaagccgcg ggaggagcag ttcaacagca cgtaccgtgt ggtcagcgtc   1500
ctcaccgtcc tgcaccagga ctggctgaac ggcaaggagt acaagtgcaa ggtctccaac   1560
aaaggcctcc cgtcctccat cgagaaaacc atctccaaag ccaaaggtgg acccacgggg   1620
gtgcgagggc cacatggaca gaggtcagct cggcccaccc tctgccctgg gagtgaccgc   1680
tgtgccaacc tctgtcccta cagggcagcc ccgagagcca caggtgtaca ccctgccccc   1740
atcccaggag gagatgacca agaaccaggt cagcctgacc tgcctggtca aaggcttcta   1800
ccccagcgac atcgccgtgg agtgggagag caatgggcag ccggagaaca actacaagac   1860
cacgcctccc gtgctggact ccgacggctc cttcttcctc tacagcaggc taaccgtgga   1920
caagagcagg tggcaggagg ggaatgtctt ctcatgctcc gtgatgcatg aggctctgca   1980
caaccactac acacagaaga gcctctccct gtctctgggt aaa                     2023
```

<210> SEQ ID NO 31
<211> LENGTH: 107
<212> TYPE: PRT
<213> ORGANISM: Artificial Sequence
<220> FEATURE:
<223> OTHER INFORMATION: Human VK1 2-1-(1) O12 JK4 acceptor framework

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 32
<211> LENGTH: 321
<212> TYPE: DNA
<213> ORGANISM: Artificial Sequence
<220> FEATURE:
<223> OTHER INFORMATION: Human VK1 2-1-(1) O12 JK4 acceptor framework

<400> SEQUENCE: 32
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta cccctctcac tttcggcgga     300
gggaccaagg tggagatcaa a                                               321

<210> SEQ ID NO 33
<211> LENGTH: 114
<212> TYPE: PRT
<213> ORGANISM: Artificial Sequence
<220> FEATURE:
<223> OTHER INFORMATION: Human VH2 3-1 2-70 JH3 acceptor framework

<400> SEQUENCE: 33

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Arg Val Ser Trp Ile Arg Gln Pro Pro Gly Lys Ala Leu Glu
        35                  40                  45

Trp Leu Ala Arg Ile Asp Trp Asp Asp Asp Lys Phe Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Ala Phe Asp Ile Trp Gly Gln Gly Thr Met Val Thr
            100                 105                 110

Val Ser

<210> SEQ ID NO 34
<211> LENGTH: 342
<212> TYPE: DNA
<213> ORGANISM: Artificial Sequence
<220> FEATURE:
<223> OTHER INFORMATION: Human VH2 3-1 2-70 JH3 acceptor framework

<400> SEQUENCE: 34
caggtcacct tgaaggagtc tggtcctgcg ctggtgaaac ccacacagac cctcacactg      60
acctgcacct tctctgggtt ctcactcagc actagtggaa tgcgtgtgag ctggatccgt     120
cagcccccag ggaaggccct ggagtggctt gcacgcattg attgggatga tgataaattc     180
tacagcacat ctctgaagac caggctcacc atctccaagg acacctccaa aaaccaggtg     240
```

```
gtccttacaa tgaccaacat ggaccctgtg acacagcca cgtattactg tgcacggata      300
gcttttgata tctggggcca agggacaatg gtcaccgtct ct                        342
```

<210> SEQ ID NO 35
<211> LENGTH: 972
<212> TYPE: PRT
<213> ORGANISM: Artificial Sequence
<220> FEATURE:
<223> OTHER INFORMATION: Amino acid sequence for CSF-1R

<400> SEQUENCE: 35

```
Met Gly Pro Gly Val Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
        50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asn Leu Ser
    290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350
```

-continued

```
Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
    450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
            500                 505                 510

Phe Leu Phe Thr Pro Val Val Val Ala Cys Met Ser Ile Met Ala Leu
        515                 520                 525

Leu Leu Leu Leu Leu Leu Leu Leu Tyr Lys Tyr Lys Gln Lys Pro
    530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
        595                 600                 605

Ala Val Leu Lys Val Ala Val Lys Met Leu Lys Ser Thr Ala His Ala
    610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
        675                 680                 685

Pro Gly Gln Asp Pro Glu Gly Gly Val Asp Tyr Lys Asn Ile His Leu
    690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
            740                 745                 750

Arg Asp Leu Leu His Phe Ser Ser Gln Val Ala Gln Gly Met Ala Phe
        755                 760                 765
```

```
Leu Ala Ser Lys Asn Cys Ile His Arg Asp Val Ala Arg Asn Val
        770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
                835                 840                 845

Phe Ser Leu Gly Leu Asn Pro Tyr Pro Gly Ile Leu Val Asn Ser Lys
850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
                915                 920                 925

Ser Ser Arg Ser Gly Gly Ser Gly Ser Ser Ser Glu Leu Glu Glu
930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
            965                 970

<210> SEQ ID NO 36
<211> LENGTH: 277
<212> TYPE: PRT
<213> ORGANISM: Artificial Sequence
<220> FEATURE:
<223> OTHER INFORMATION: Amino acid sequence for CSF-1R

<400> SEQUENCE: 36

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
                20                  25                  30

Gly Pro Pro Ser Pro His Trp Thr Leu Tyr Ser Asp Gly Ser Ser Ser
            35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
                100                 105                 110

Pro Val Leu Glu Ala Gly Val Ser Leu Val Arg Val Arg Gly Arg Pro
            115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160
```

```
Leu Met Gly Gly Arg Lys Val Met Ser Ile Ser Ile Arg Leu Lys Val
            165                 170                 175

Gln Lys Val Ile Pro Gly Pro Pro Ala Leu Thr Leu Val Pro Ala Glu
        180                 185                 190

Leu Val Arg Ile Arg Gly Glu Ala Ala Gln Ile Val Cys Ser Ala Ser
            195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val
            275

<210> SEQ ID NO 37
<211> LENGTH: 49
<212> TYPE: PRT
<213> ORGANISM: Artificial Sequence
<220> FEATURE:
<223> OTHER INFORMATION: Amino acid sequence for CSF-1R

<400> SEQUENCE: 37

Met Arg His Thr Asn Tyr Ser Phe Ser Pro Trp His Gly Phe Thr Ile
1               5                   10                  15

His Arg Ala Lys Phe Ile Gln Ser Gln Asp Tyr Gln Cys Ser Ala Leu
            20                  25                  30

Met Gly Gly Arg Lys Val Met Ser Ile Ser Ile Arg Leu Lys Val Gln
        35                  40                  45

Lys

<210> SEQ ID NO 38
<211> LENGTH: 493
<212> TYPE: PRT
<213> ORGANISM: Artificial Sequence
<220> FEATURE:
<223> OTHER INFORMATION: Amino acid sequence for CSF-1R (SNP V32G,
      A245S, H247P, V279M, position underlined)

<400> SEQUENCE: 38

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125
```

Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
210                 215                 220

Leu Ala Ile His Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
        355                 360                 365

Gly Trp Arg Ala Leu Thr Phe Glu Leu Thr Leu Arg Tyr Pro Pro Glu
370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
        435                 440                 445

Val Gln Ser Leu Leu Thr Val Glu Thr Leu Glu His Asn Gln Thr Tyr
450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu
                485                 490

<210> SEQ ID NO 39
<211> LENGTH: 512
<212> TYPE: PRT
<213> ORGANISM: Artificial Sequence
<220> FEATURE:
<223> OTHER INFORMATION: sequence of human CSF-1R extracellular domain

<400> SEQUENCE: 39

```
Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
50                      55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
                100                 105                 110

Gln Glu Val Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
                180                 185                 190

Leu Lys Val Gln Lys Val Ile Pro Gly Pro Pro Ala Leu Thr Leu Val
            195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
    275                 280                 285

Thr Ser Met Phe Phe Arg Val Val Glu Ser Ala Tyr Leu Asn Leu Ser
290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
    355                 360                 365

Pro Arg Leu Lys Pro Ser Glu Ala Gly Arg Tyr Ser Phe Leu Ala Arg
370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415
```

-continued

```
Leu Leu Cys Ala Ala Ser Gly Tyr Pro Gln Pro Asn Val Thr Trp Leu
            420             425             430

Gln Cys Ser Gly His Thr Asp Arg Cys Asp Glu Ala Gln Val Leu Gln
        435             440             445

Val Trp Asp Asp Pro Tyr Pro Glu Val Leu Ser Gln Glu Pro Phe His
    450             455             460

Lys Val Thr Val Gln Ser Leu Leu Thr Val Glu Thr Leu Glu His Asn
465             470             475             480

Gln Thr Tyr Glu Cys Arg Ala His Asn Ser Val Gly Ser Gly Ser Trp
                485             490             495

Ala Phe Ile Pro Ile Ser Ala Gly Ala His Thr His Pro Pro Asp Glu
            500             505             510
```